United States Patent
Yang et al.

(10) Patent No.: US 10,980,601 B2
(45) Date of Patent: *Apr. 20, 2021

(54) SYSTEM AND METHODS FOR INTRAOPERATIVE GUIDANCE FEEDBACK

(71) Applicant: RYERSON UNIVERSITY, Toronto (CA)

(72) Inventors: Victor Xiao Dong Yang, North York (CA); Beau Anthony Standish, Toronto (CA); Adrian Linus Dinesh Mariampillai, Toronto (CA); Michael Ka Kit Leung, Markham (CA)

(73) Assignee: RYERSON UNIVERSITY, Toronto (CA)

( * ) Notice: Subject to any disclaimer, the term of this patent is extended or adjusted under 35 U.S.C. 154(b) by 511 days.

This patent is subject to a terminal disclaimer.

(21) Appl. No.: 15/883,446

(22) Filed: Jan. 30, 2018

(65) Prior Publication Data

US 2018/0153626 A1 Jun. 7, 2018

Related U.S. Application Data

(63) Continuation of application No. 15/340,077, filed on Nov. 1, 2016, now Pat. No. 9,901,409, which is a
(Continued)

(51) Int. Cl.
*A61B 5/00* (2006.01)
*A61B 34/20* (2016.01)
(Continued)

(52) U.S. Cl.
CPC .............. *A61B 34/20* (2016.02); *A61B 5/055* (2013.01); *A61B 6/032* (2013.01); *A61B 90/30* (2016.02);
(Continued)

(58) Field of Classification Search
CPC ......... A61B 34/20; A61B 90/39; A61B 6/032; A61B 90/30; A61B 5/055;
(Continued)

(56) References Cited

U.S. PATENT DOCUMENTS 9,119,670 B2 * 9/2015 Yang ...................... A61B 5/055
9,510,914 B2 * 12/2016 Yang ...................... A61B 5/055

* cited by examiner

*Primary Examiner* — Joel Lamprecht
(74) *Attorney, Agent, or Firm* — Hill & Schumacher

(57) ABSTRACT

Systems and methods for surgical guidance and image registration are provided, in which three-dimensional image data associated with an object or patient is registered to topological image data obtained using a surface topology imaging device. The surface topology imaging device may be rigidly attached to an optical position measurement system that also tracks fiducial markers on a movable instrument. The instrument may be registered to the topological image data, such that the topological image data and the movable instrument are registered to the three-dimensional image data. The three-dimensional image data may be CT or MRI data associated with a patient. The system may also co-register images pertaining to a surgical plan with the three-dimensional image data. In another aspect, the surface topology imaging device may be configured to directly track fiducial markers on a movable instrument. The fiducial markers may be tracked according to surface texture.

21 Claims, 38 Drawing Sheets

Related U.S. Application Data continuation of application No. 14/816,292, filed on Aug. 3, 2015, now Pat. No. 9,510,914, which is a continuation of application No. 13/664,613, filed on Oct. 31, 2012, now Pat. No. 9,119,670, which is a continuation-in-part of application No. PCT/CA2011/050257, filed on Apr. 28, 2011.

(60) Provisional application No. 61/328,679, filed on Apr. 28, 2010.

(51) Int. Cl.
    *A61B 90/30*    (2016.01)
    *A61B 5/055*    (2006.01)
    *G01B 11/24*    (2006.01)
    *G01B 11/245*    (2006.01)
    *A61B 90/00*    (2016.01)
    *A61B 6/03*    (2006.01)
    *G01B 11/25*    (2006.01)
    *A61B 6/00*    (2006.01)
    *A61B 8/08*    (2006.01)
    *A61B 17/00*    (2006.01)
    *A61B 34/10*    (2016.01)

(52) U.S. Cl.
CPC .............. *A61B 90/39* (2016.02); *G01B 11/24* (2013.01); *G01B 11/245* (2013.01); *G01B 11/25* (2013.01); *A61B 6/5229* (2013.01); *A61B 6/5247* (2013.01); *A61B 8/5238* (2013.01); *A61B 90/361* (2016.02); *A61B 2017/00203* (2013.01); *A61B 2034/105* (2016.02); *A61B 2034/107* (2016.02); *A61B 2034/2055* (2016.02); *A61B 2034/2057* (2016.02); *A61B 2034/2065* (2016.02); *A61B 2090/363* (2016.02); *A61B 2090/364* (2016.02); *A61B 2090/365* (2016.02); *A61B 2090/366* (2016.02); *A61B 2090/371* (2016.02); *A61B 2090/373* (2016.02); *A61B 2090/397* (2016.02); *A61B 2090/3945* (2016.02); *A61B 2090/3979* (2016.02); *A61B 2090/3983* (2016.02); *A61B 2560/0475* (2013.01); *A61B 2576/02* (2013.01)

(58) Field of Classification Search
CPC .......... A61B 2090/397; A61B 2576/02; A61B 2090/3983; A61B 2034/2057; A61B 2034/2065; A61B 2090/363; A61B 2090/365; A61B 2090/3945; A61B 2090/3979; A61B 2090/364; A61B 90/361; A61B 2034/105; A61B 2034/107; A61B 2090/371; A61B 2090/373; A61B 2034/2055; A61B 2090/366; A61B 2560/0475; A61B 6/5229; A61B 6/5247; A61B 8/5238; A61B 2017/00203; G01B 11/25; G01B 11/24; G01B 11/245
See application file for complete search history.

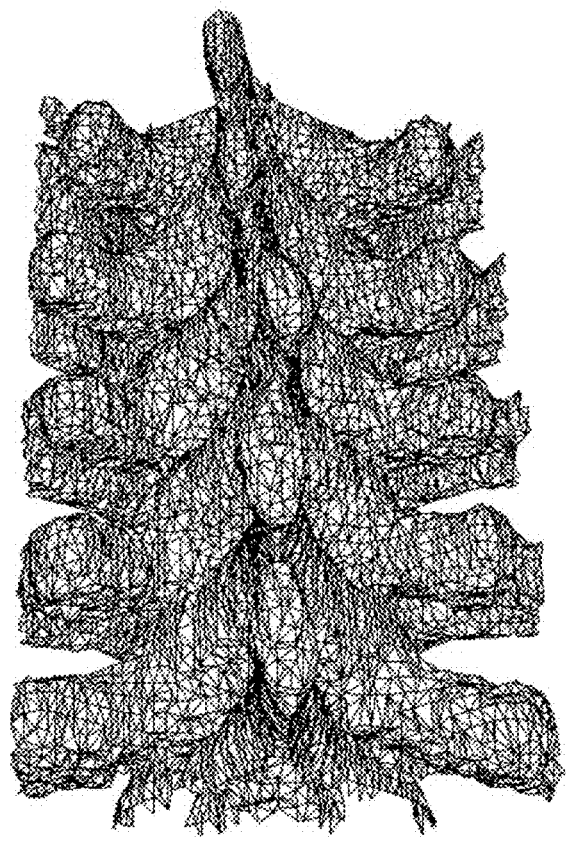
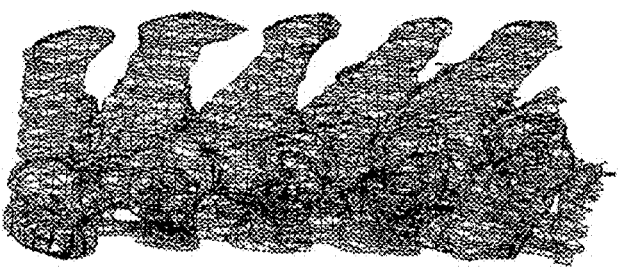
FIG. 3C
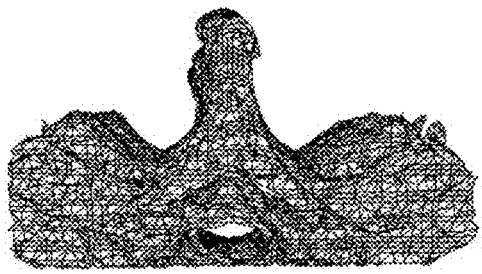
FIG. 3B
FIG. 3D

SYSTEM AND METHODS FOR INTRAOPERATIVE GUIDANCE FEEDBACK

CROSS-REFERENCE TO RELATED APPLICATION

This application is a continuation of U.S. patent application Ser. No. 14/816,292, titled "SYSTEM AND METHODS FOR INTRAOPERATIVE GUIDANCE FEEDBACK" filed on Aug. 3, 2015, the entire contents of which are incorporated herein by reference, which is a continuation of U.S. patent application Ser. No. 13/664,613, titled "SYSTEM AND METHODS FOR INTRAOPERATIVE GUIDANCE FEEDBACK" filed on Oct. 31, 2012, the entire contents of which are incorporated herein by reference, which claims priority to PCT Patent Application No. PCT/CA2011/050257, titled "SYSTEM AND METHODS FOR INTRAOPERATIVE GUIDANCE FEEDBACK" and filed on Apr. 28, 2011, the entire contents of which are incorporated herein by reference, which claims priority to U.S. Provisional Application No. 61/328,679, titled "SYSTEM AND METHODS FOR INTRAOPERATIVE GUIDANCE FEEDBACK" and filed on Apr. 28, 2010, the entire contents of which are incorporated herein by reference.

BACKGROUND

The present disclosure relates generally to surgical guidance.

Image-guided target tracking and surgical guidance is a method for locating a specific target within three-dimensional (3D) space. This technique is routinely used in medical procedures to locate an object in the human body, such as the spine, brain or other organ structures, during surgery.

One approach to a guided surgical intervention includes the use of fiducial markers that are attached to the body with a clamp, an adhesive, or through other means. Generally, these fiducial markers are aligned to a 3D representation of the body, which may be acquired by different imaging modalities. This 3D representation, usually acquired before surgery, may include a specific region, such as a vertebral column, to a scan of the entire body. Within this 3D representation, areas of interest are located and matched to the fiducial markers in the real surgical space. This results in a coordinate system transform that maps the relative position of the region of interest to the location of the fiducial markers to provide visual feedback to the clinician during surgery. The surgeon can then use this information to facilitate guidance to a specific location in the body that is related to the region of interest in the image.

Optical-based surgical navigation has been used for the past decade to guide spinal surgeries and, in particular, placement of screws in the spine. These systems are based on two cameras that detect light that is either emitted (mounted with LEDs) as disclosed in U.S. Pat. No. 5,921,992, or passively reflected from surgical tools and probes as disclosed in U.S. Pat. No. 6,061,644. Using the signal detected by the cameras combined with the knowledge of the dimensions of the navigation probes, a computer workstation is able to precisely determine where the tip of the surgical instrument lies.

U.S. Pat. Nos. 5,531,520 and 5,999,840 provide a system that utilizes a plane of laser light and a video camera to obtain three-dimensional measurements of the patient's skin, where the system employs the "structured light" method of obtaining the desired measurements for registration of 3D pre-operative image data. Prior to a surgical procedure, pre-operative MRI or CT data is first obtained. Subsequently, in an operative setting, the patient is scanned by a laser range scanner. The pre-operative MRI or CT scan is automatically registered to patient skin surface obtained by the laser range scanner, providing a transformation from MRI/CT to patient. The position and orientation of a video camera relative to the patient is determined by matching video images of the laser points on an object to the actual 3D laser data. This provides a transformation from patient to video camera. The registered anatomy data is displayed in enhanced visualization to "see" inside the patient.

The registration process taught by U.S. Pat. No. 5,999,840 also discloses the tracking of surgical instruments and probes. A probe is tracked by a separate probe tracking system, in which dedicated probe tracking cameras are employed to track a probe. The tracked probe data is then registered to the three-dimensional skin surface data using a calibration process. Thereafter, the data registration between the probe and the skin surface is used to provide visualization information to the surgeon.

In order to track the probe, a calibration procedure is needed to register the reference frame of the probe tracking system to that of the optical surface measurement system. This calibration process involves the measurement of a calibration object. The process requires that the probe tracking reference frame be fixed relative to the optical surface measurement system to maintain calibration, such that the optical surface measurement system cannot be moved relative to the probe tracking reference frame intraoperatively. This requirement can constrain surgical workflow and cause a need for inter-operative re-calibration of the system.

SUMMARY

Three-dimensional image data associated with an object or patient is registered to topological image data obtained using a surface topology imaging device. The surface topology imaging device may be rigidly attached to an optical position measurement system that also tracks fiducial markers on a movable instrument. The instrument may be registered to the topological image data, such that the topological image data and the movable instrument are registered to the three-dimensional image data. The three-dimensional image data may be CT or MRI data associated with a patient. The system may also co-register images pertaining to a surgical plan with the three-dimensional image data. In another aspect, the surface topology imaging device may be configured to directly track fiducial markers on a movable instrument. The fiducial markers may be tracked according to surface texture. Example implementations described herein provide a system for providing surgical guidance feedback during a surgical procedure.

Accordingly, in one aspect, there is provided surgical guidance system comprising: a storage medium for storing pre-operative image data associated with a patient; an integrated surface topology imaging and optical position measurement device comprising: an optical projection device for projecting optical radiation onto an exposed surface of the patient, such that backscattered optical radiation is suitable for optical surface topology detection; an optical source having a wavelength selected to illuminate a set of fiducial markers provided on a movable instrument; two or more cameras, wherein at least one of said two or more cameras is configured for imaging the backscattered optical radiation, and wherein at least two of said two or more cameras are configured for imaging the set of fiducial markers when illuminated; a surgical guidance controller operatively connected to said integrated surface topology imaging and optical position measurement device and said storage medium, wherein said surgical guidance controller includes a processor configured to: control said optical projection device to illuminate the exposed surface and obtain, from said at least one camera, topological image data associated with the exposed surface; and control said optical source to illuminate the set of fiducial markers and obtain, from said two or more cameras, positional image data associated with said set of fiducial markers; determine a position and an orientation of said movable instrument relative to said exposed surface; and register said topological image data, and said position and orientation of said movable instrument to said pre-operative image data; wherein said optical projection device, said optical source, and said two or more cameras are rigidly mounted on a frame, thereby maintaining a fixed calibration of said system without requiring inter-operative recalibration.

In another aspect, there is provided a method of registering surface topological image data to preoperative image data using an integrated system comprising a surface topology imaging device and an optical position measurement device; the surface topology imaging device comprising: an optical projection device for projecting optical radiation onto an exposed surface of a patient, such that backscattered optical radiation is suitable for optical surface topology detection; and one or more first cameras configured for imaging the backscattered optical radiation wherein the optical projection device; the optical position measurement device comprising: an optical source having a wavelength selected to illuminate a set of fiducial markers provided on a movable instrument; two or more second cameras for imaging the set of fiducial markers when illuminated; wherein the surface topology imaging device and the optical position measurement device are rigidly mounted on a frame; the method comprising: obtaining pre-operative image data associated with a patient; obtaining pre-determined calibration data for relating the coordinate system of the optical position measurement device and the coordinate system of the surface topology imaging device; optically scanning the exposed surface of the patient with the optical projection device and obtaining, from the one or more first cameras, topological image data associated with the exposed surface; illuminating the set of fiducial markers by powering the optical source and obtaining, from the second cameras, optical images of the set of fiducial markers; processing the optical images to determine a position and orientation of the movable instrument relative to the exposed surface, based on the pre-determined calibration data; and registering the topological image data, and the position and orientation of the movable instrument, to the pre-operative image data.

In another aspect, there is provided a surgical guidance system comprising a storage medium for storing pre-operative image data associated with a patient; a surface topology imaging device comprising: an optical projection device for projecting optical radiation onto an exposed surface of the patient and onto a set of fiducial markers provided on a movable instrument, such that backscattered optical radiation is suitable for optical surface topology detection; one or more cameras configured for imaging the backscattered optical radiation; a surgical guidance controller operatively connected to said surface topology imaging device and said storage medium, wherein said surgical guidance controller includes a processor configured to: control said optical projection device to illuminate the exposed surface and the set of fiducial markers and to obtain, from said one or more cameras, topological image data associated with the exposed surface and the set of fiducial markers; and determine a position and an orientation of said movable instrument relative to said exposed surface; and register said topological image data, and said position and orientation of said movable instrument to said pre-operative image data; wherein said optical projection device and said one or more cameras are rigidly mounted on a frame, thereby maintaining a fixed calibration of said system without requiring inter-operative recalibration.

In another aspect, there is provided a method of registering a topological image data to pre-operative image data for surgical guidance, wherein the topological image data is obtained by a surface topology imaging device, the method comprising the steps of: storing the pre-operative image data associated with a patient; controlling the surface topology imaging device to optically scan an exposed surface of the patient and to optically scan a set of surface texture based fiducial markers provided on a movable instrument; recording topological image data associated with the exposed surface and the fiducial markers; processing the topological image data to determine a position and orientation of the movable instrument relative to the exposed surface; and registering the topological image data, and the position and orientation of the movable instrument, to the pre-operative image data.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 3(b) is a schematic of an example surface topology reconstruction of a spine and corresponding vertebrae segmented from a CT image dataset in a posterior orientation.

FIG. 3(c) is a schematic of the surface topology reconstruction of FIG. 3b in a lateral orientation.

FIG. 3(d) is a schematic of the surface topology reconstruction of FIG. 3b in a cross-sectional orientation.

DETAILED DESCRIPTION

Figure 1A:
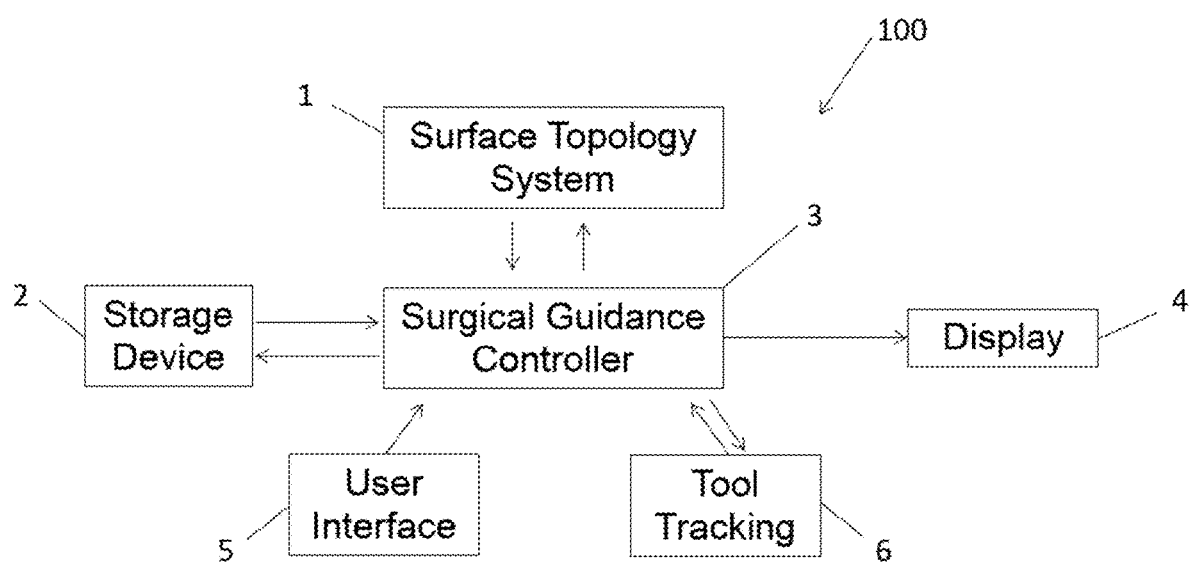
FIG. 1a is a block diagram illustrating an example implementation of components in an image-based surgical guidance feedback system, demonstrating flows of system information.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

The following terms used in this description have the following meanings:

As used herein, "registration" refers to a process of matching data points or sets of data points from various datasets to the same coordinate system under a set of constraints. Various image datasets from a target image space are aligned to a reference image space. For example, a set of points in $R^3$ (three-dimensional space) acquired by sampling an object at different time points and/or using different techniques (for example, MRI, CT, positron emission tomography (PET), ultrasound, and back scattered radiation) provide datasets in different coordinate systems.

As used herein, "transformation" refers to a process of generating a map to instruct how to scale, translate, and rotate all points in an object such that the object remains aligned to one of another object and the object itself, at a different time point and/or imaged with a different technique. A subset of transformations known as "affine transformations" maps points from $R^3 \rightarrow R^3$. Such affine transformations can be represented by matrices and are the outputs from the registration.

As used herein, "translation" refers to a shift of a point or set of points in $R^3$ by a fixed distance in the same direction. Translation is one component of transformation.

As used herein, "rotation" refers to a circular motion of a point or set of points around a fixed axis in $R^3$ termed an axis of rotation. Rotation is another component of transformation.

As used herein, "scaling" refers to the enlarging or shrinking the dimension of an object. For uniform scaling, the scale factor is the same in all directions. Scaling is another component of transformation.

As used herein, "location" refers to the position of a point or an object in physical space $R^3$ relative to an object (for example, bone, camera, surface structure) in a general area.

As used herein, "orientation" refers to any one of a number of angular positions relative to a set of reference axes in $R^3$, where one point is held in a fixed position and around which the object may be rotated.

As used herein, "backscattered radiation" refers to the deflection of radiation through angles greater than 90° to the initial direction of travel. Example principles of backscattered radiation for obtaining surface topology information include, but are not limited to, structured light, phase-modulated light, laser triangulation, laser range finding, photogrammetry, and stereoscopy. Backscattered radiation further includes electromagnetic non-ionizing radiation in either the visible or invisible range (i.e. infrared or ultraviolet).

As used herein, "texture" refers to the characteristics of a surface, which include its representation in color and/or roughness. Specifically, the color texture of a surface is characterized by how its individual parts are spectrally perceived by an image capture system, such as a camera. Roughness refers to how individual parts of a surface belonging to a predefined region deviate from the mean of that region.

System Overview

Referring now to FIG. 1(a), an example image-based surgical guidance feedback system 100 is schematically illustrated. System 100 includes: a surface topology backscattered radiation image acquisition system 1, for example, a structured light illumination, laser range scanning, or laser triangulation surface topology imaging system; a surgical guidance controller 3 in communication with the surface topology image acquisition system 1; a storage device 2 in communication with the surgical guidance controller 3, for example, magnetic or solid state media, for storing image data and processed data; a display 4, such as a computer monitor, in communication with the surgical guidance controller 3; and a tool tracking subsystem 6, in communication with the surgical guidance controller 3.

As will be further described below, surgical guidance controller 3 registers acquired image data from the surface topology backscattered radiation image acquisition system 1 to additional, for example, pre-operative, image data from the storage device 2. The registered data are then provided on the display 4 in an output format including image data and additional text-based data such as the registration error, and distance measurements that indicate the proximity of a surgical tool to a target defined in the surgical plan. In one example, after co-registration, the backscattered image data may be displayed together with the registered additional image data as a single image. Guidance feedback can be provided in part through other output user interfaces such as, for example, speakers or other audible output devices, and light beams projected directly on the patient showing desired position of an interventional device to be inserted or attached, such as a pedicle screw, or a combination thereof. The system 100 is particularly advantageous for surgeries involving orthopedic structures, including spine, hip, skull, and knee. The system may, for example, be employed to provide intraoperative guidance for orthopaedic, neurosurgical, head and neck, and otolaryngological surgical procedures.

The forthcoming description describes example implementations of methods and systems primarily with illustrative reference to applications for guidance feedback in spinal surgery, particularly the insertion of pedicle screws. The insertion of pedicle screws is used for illustration, because a demanding aspect of pedicle screw insertion is the identification of the entry to the pedicle canal and the determination of the angle of the pedicle canal relative to the surgically exposed surface of the vertebrae without direct visualization of the pedicle canal and the vertebrae. Typically, a surgeon exposes only a portion of the posterior of the vertebral bone through which the pedicle is entered. Failure to enter the pedicle on a proper trajectory can, for example, result in violation of the walls of the pedicle or the anterior cortex of the vertebrae.

Surgical guidance controller 3 can be, for example, a processing unit and associated memory containing one or more computer programs to control the operation of the system, the processing unit in communication with a user interface unit 5 and the display 4. In one example, surgical guidance controller 3 may be a computing system such as a personal computer or other computing device, for example in the form of a computer workstation, incorporating a hardware processor and memory, where computations are performed by the processor in accordance with computer programs stored in the memory to carry out the methods described herein. For example, the processor can be a central processing unit or a combination of a central processing unit and a graphical processing unit.

Surgical guidance controller 3 records and processes backscattered radiation from the surface topology of the rigid surgical structure of interest and, utilizing the preoperative image inputs above, operates, for example, to provide real-space spatial relationships of the surgical target to the preoperative 3D image dataset and an optional surgical plan that reflects current intraoperative geometry. Example methods of processing acquired surface topology data to register the surface topology data to pre-operative 3D image data are described in further detail below. Surgical guidance controller 3 may also optionally determine the real-space spatial relationship of a surgical tool in relation to the intraoperative geometry of the target rigid surgical structure of interest, as described in more detail below.

In one embodiment, system 100 includes a general purpose computer or any other hardware equivalents. Thus, the system may include at least one processor (CPU/microprocessor), a memory, which may include random access memory (RAM), one or more storage devices (e.g., a tape drive, a floppy drive, a hard disk drive or a compact disk drive), and/or read only memory (ROM), and various input/output devices (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, 6-degree input device based on the position tracking of a handheld device, and the like, and/or a microphone for capturing speech commands, etc.). In one embodiment, surgical guidance controller 3 is implemented as a set of instructions which when executed in the processor causes the system to perform one or more methods described in the disclosure.

Surgical guidance controller 3 may also be implemented as one or more physical devices that are coupled to the CPU through a communication channel. For example, surgical guidance controller 3 can be implemented using application specific integrated circuits (ASIC). Alternatively, surgical guidance controller 3 can be implemented as a combination of hardware and software, where the software is loaded into the processor from the memory or over a network connection. In one embodiment, surgical guidance controller 3 (including associated data structures) of the present disclosure can be stored on a computer readable medium, e.g., RAM memory, magnetic or optical drive or diskette and the like.

While some embodiments have been described in the context of fully functioning computers and computer systems, those skilled in the art will appreciate that various embodiments are capable of being distributed as a program product in a variety of forms and are capable of being applied regardless of the particular type of machine or computer-readable media used to actually effect the distribution.

Examples of computer-readable media include but are not limited to recordable and non-recordable type media such as volatile and non-volatile memory devices, read-only memory (ROM), random access memory (RAM), flash memory devices, floppy and other removable disks, magnetic disk storage media, optical storage media (e.g., Compact Disk Read-Only Memory (CD ROMS), Digital Versatile Disks, (DVDs), etc.), among others. The instructions can be embodied in digital and analog communication links for electrical, optical, acoustical or other forms of propagated signals, such as carrier waves, infrared signals, digital signals, etc.

A machine-readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version.

Alternatively, the logic to perform the processes as discussed above could be implemented in additional computer and/or machine-readable media, such as discrete hardware components including large-scale integrated circuits (LSIs), application-specific integrated circuits (ASICs), or firmware such as electrically erasable programmable read-only memory (EEPROMs).

The controller can further include a clutter identification module to identify clutter in the acquired backscattered image data.

The controller can further include a confidence criteria module to determine if registration is occurring within a pre-set confidence criteria, and if not, intervention may be sought to provide additional data to be used in intraoperatively registering.

Figure 1B:
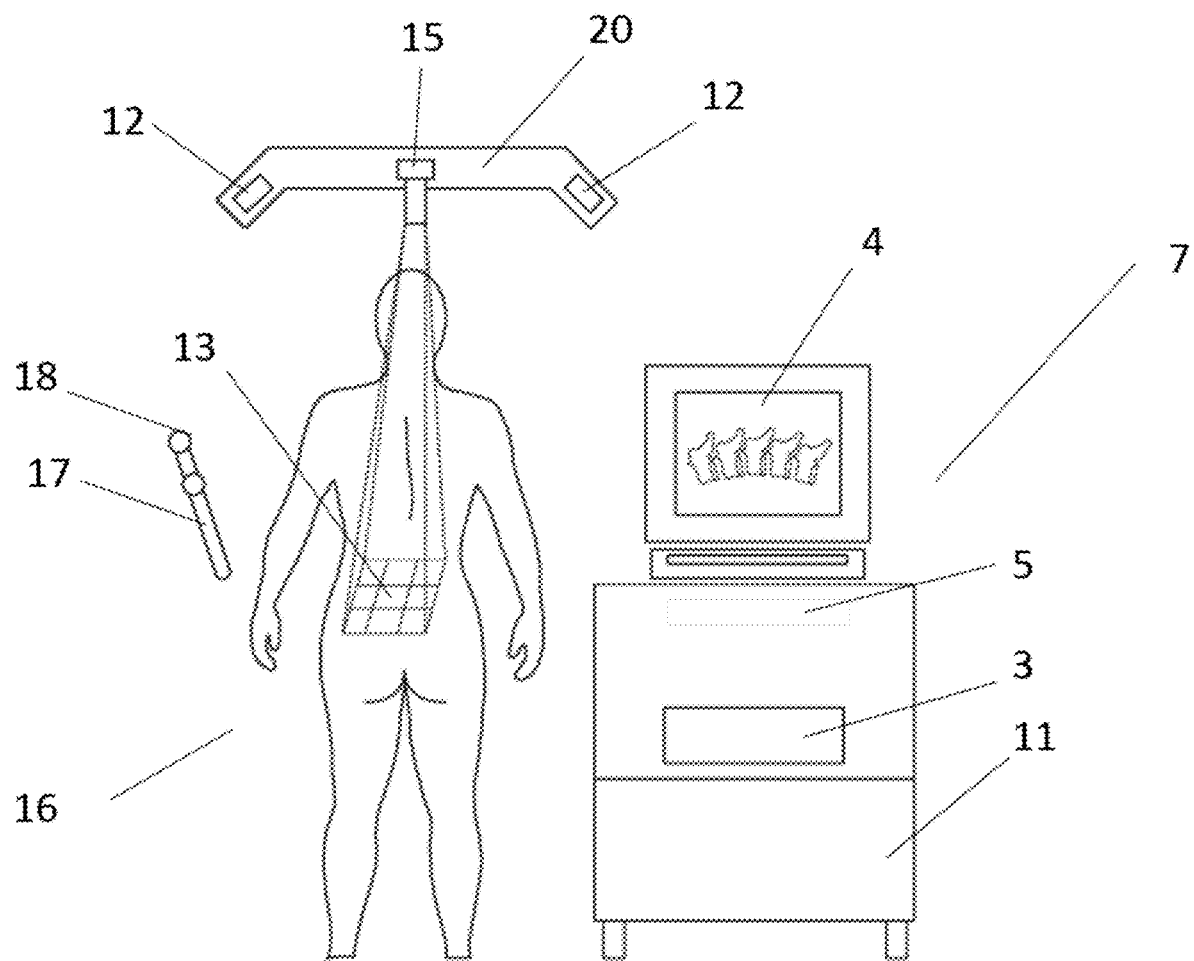
FIG. 1b is an example schematic of an image-guided surgical guidance system in use during spinal surgery.
Figure 6A:
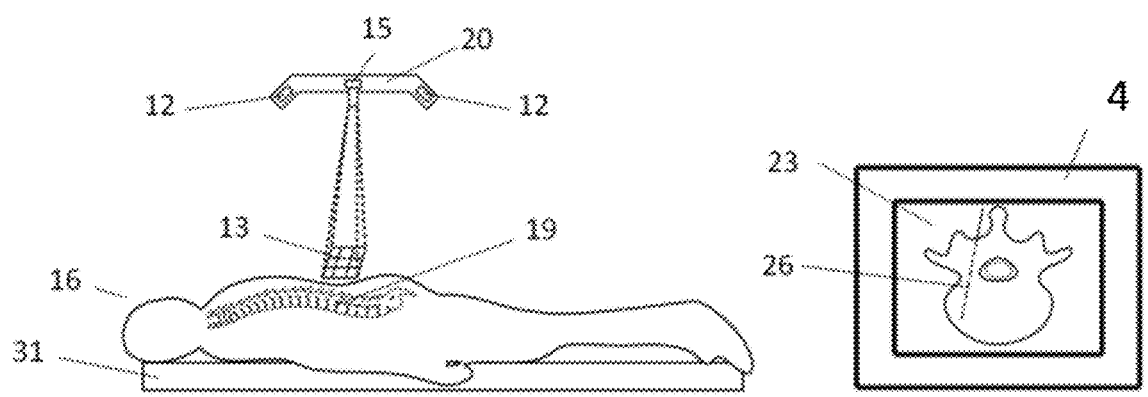
FIG. 6(a) illustrates an example implementation of pre-operative image acquisition of a spine of a subject and output including a predetermined principle axis demarcating an implantation trajectory of a surgical interventional device.

Referring to FIG. 1(b), an example implementation of an image-guided spinal surgical procedure using the image-based surgical guidance feedback system 100 is provided. System 100 may include, for example, a user workstation 7, incorporating surgical guidance controller 3 and the memory storage device 2 to carry out the methods described herein. User workstation 7 may consist of display 4, such as a high definition monitor, the surgical guidance controller 3, and user interface 5, such as a keyboard, for inputting instructions into the system 100. All components can be installed into a single unit, such as a medical grade cart 11. In this implementation, the system further comprises two cameras 12 for detecting the structured light grid pattern 13 emitted from the digital projector 15, which is incident on the subject 16. FIG. 6(a) illustrates a specific example in which a portion of an exposed spine is imaged using a structured light pattern to determine and record the three-dimensional surface profile for co-registration with pre-operative 3D image data.

A tool 17 (for example, a surgical tool, probe, surgical instrument, or other freely movable item), having fiducial markers 18 adhered thereto, may also be integrated with system 100, in order to co-register the position of tool 17 with 3D pre-operative image data. As further described below, the position and orientation of tool 17 may be determined using an additional global position sensor, or alternatively may be determined using measurements obtained from surface topology backscattered radiation image acquisition system 1.

Referring now to FIG. 1(*b*), an example implementation of an image-guided spinal surgical procedure using the image-based surgical guidance feedback system 100 is provided. The image-based surgical guidance system 100 can be implemented using, for example, a backscattered radiation surface topology imaging device, at least one registration algorithm, and a software module to provide intraoperative high-speed feedback information to the clinician for planning and executing the surgical procedure. Optionally, color textures of objects within a field of view can be captured either simultaneously by the backscattered radiation imaging device, or separately by a second imaging device, for improving the accuracy and speed of the registration. The surface topology information can be registered to the 3D preoperative imaging dataset to provide structural information about the surgical structure of interest that is not visible to the clinician. While system 100 can be used with a set of fiducial markers placed on the structure of interest for tracking during imaging, it is an advantage of the present system that fiducial markers are not required for surgical guidance.

System 100 may include, for example, a user workstation 7, incorporating the surgical guidance controller 3 and the memory storage device 2 to carry out the methods described herein. User workstation 7 may consist of display 4, such as a high definition monitor, the surgical guidance controller 3, and user interface 5, such as a keyboard, for inputting instructions into the system 100. All components can be installed into a single unit, such as a medical grade cart 11. In this example implementation, the system further comprises two cameras 12 for detecting the structured light grid pattern 13 emitted from the digital projector 15, which is incident on the subject 16.

As shown in FIG. 1(*b*), the surface topology backscattered radiation image acquisition system 1 may include at least one camera 12, and preferably two cameras 12. While the system 1 is operable with a single camera 12, the inclusion of two cameras 12 can increase the field of view and surface coverage (with fewer blind spots). Using multiple cameras can also enable spectroscopic imaging via the inclusion of filters. Imaging frame 20 may be optionally provided to house both topology imaging system 1 (for example, a digital projector 15 where a structured light source is used) and the one or more cameras 12. The surface topology information acquired by this system is registered to the 3D preoperative imaging dataset to provide information relating to sub-surface structure and composition that would be otherwise hidden from the operator's view.

Backscattered Radiation Topology Systems

According to example methods provided herein, backscattered radiation topology and texture-based surgical tracking and navigation can be enabled during surgery, for example, for feedback guidance in the placement of the surgical interventional device to the surgical structure of interest (e.g. attachment of fixation devices to the spine during spinal surgery). Backscattered radiation, including electromagnetic non-ionizing radiation in either the visible or invisible range, can be utilized for acquisition of surface topology image data. The use of light outside the visible range (i.e. infrared or ultraviolet) may be beneficial so the field of view of a surgeon is not distracted. Appropriate safety precautions may be required when using invisible light. Using a 3D backscattered imaging device, topology maps of real-space surgical surfaces can be created for exposed regions of interest. Correspondingly, by image registration, structural information beneath the surface that is hidden from the surgeon's view is provided.

The 3D backscattered radiation surface topology imaging devices may employ, but are not limited to, structured light illumination, laser triangulation, laser range finding, time-of-flight/phase modulation, photogrammetry, and stereoscopic methods. Some further example details of such example methods include:

i) Photogrammetric devices: Multiple images of a region of interest are acquired from different angles by either moving a single camera or by using multiple fixed cameras. Based on acquired images, a surface topography map of a region can be generated.

ii) Laser triangulation devices: A collimated laser beam can be used to illuminate a point on a target surface of interest. A portion of the light is reflected from the surface and is detected using for example, a charge-coupled device (CCD) camera. The position of the detected light on the CCD camera can be used to determine the distance to that point on the object. Scanning the laser beam across the surface using a device such as a galvo scanner will yield a surface topography map.

iii) Time of flight/phase modulation devices: A laser can be passed through a phase modulation device and then split into two arms of an interferometer. One arm of the interferometer contains a mirror (reference arm) and the other can be sent to the object surface being scanned (sample arm). Sample arm optics collimate/focus the laser to a point on the surface and galvo scanners can be used to scan the region of interest. The reflected light from the sample and reference arm beams can be recombined and measured by a photodetector. The relative displacement of target in sample arm to the mirror in reference arm leads to a phase shift in the measured signal relative to the modulation frequency of the phase modulator. This phase shift map can then be directly converted to a surface topography map.

iv) Structured light photography devices: A region of interest is illuminated with one or multiple patterns either by using a fringe (sinusoidal) pattern or binary pattern generated, for example, by interference of two laser beams or using a digital projector. Using one or multiple camera(s), images can be acquired to record the projected pattern that appears on the object. Using knowledge of how the pattern appears on a flat surface and known orientations of the camera(s) and projector, deformations in the pattern allows a surface topography map of the target to be generated, as further described below. Such devices will be known to those skilled in the art, and are described in Salvi (J. Salvi, "Pattern Codification Strategies in Structured Light Systems", Pattern Recognition (37), pg. 827-849, April 2004) and Zhang (S. Zhang, "High-Resolution, Real-Time Three-Dimensional Shape Measurement", Optical Engineering 45(12), 123601, December 2006).

Colour Filters for Spectral Processing

Optionally, color textures of objects within the field of view, captured either simultaneously by the topology system 1 or separately by another camera, can serve as additional features that can be extracted to improve accuracy and speed of registration.

Figure 2:
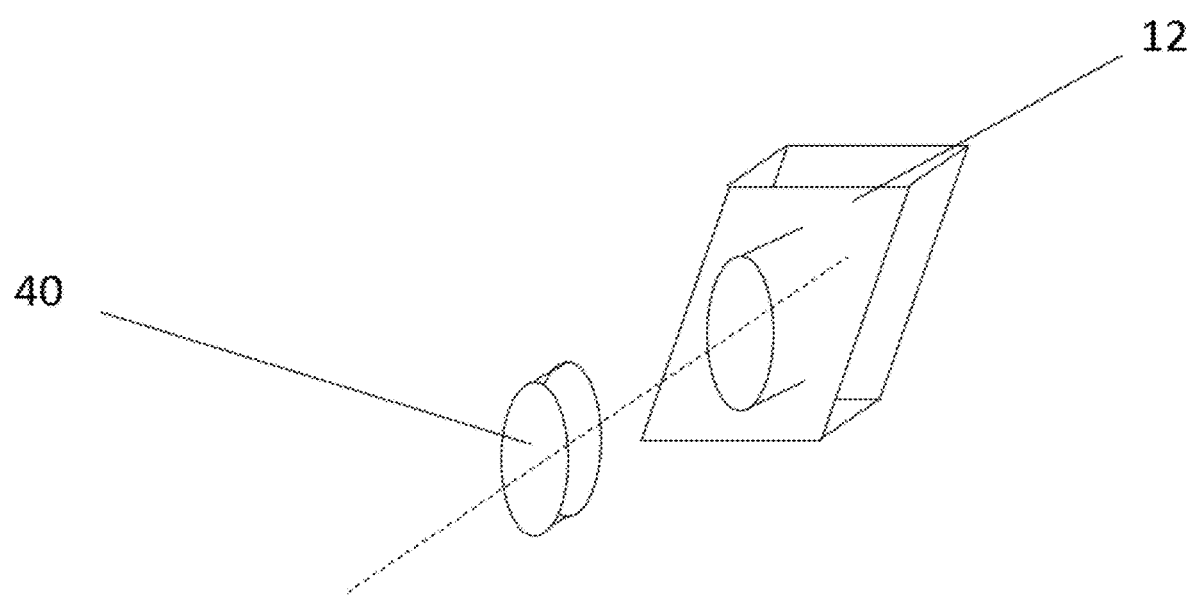
FIG. 2 illustrates an example implementation of an optical filter with a camera to limit specific wavelengths detected for topology imaging.

Referring to FIG. 2, to improve surface identification, a filter 40 can be integrated into the cameras 12 to preferentially accept only certain bands of the electromagnetic spectrum. The filters 40 can be optimized to achieve maximum contrast between different materials and thus improve the clutter identification process, as further described below. For example, bands that are common to backscattered radiation from typical clutter items, the surgical structure of interest, and the surgical tool(s) can be filtered out such that backscattered radiation of high contrast between clutter items, surgical structure and surgical tools can be acquired.

A filter 40 may be fixed in front of a given camera 12, or may be movable. For example, a filter 40 may be slidably movable into and out of the optical path of camera 12, manually or in an automated fashion (such as driven by a motor or a solenoid). In another example, multiple filters may be periodically positioned in front of a given camera in order to acquire spectrally resolved images with different spectral ranges at different instants in time, thereby providing time dependent spectral multiplexing. Such an embodiment may be achieved, for example, by positioning a plurality of filters in a filter wheel that is controllably rotated to bring each filter in the filter wheel into the optical path of the camera at different moments in time.

3D Image Dataset

Image dataset provided to system 100 can include any of the following non-limiting examples: preoperative 3D image data of a surgical structure of interest, such as the spine, in a subject acquired, for example, using any one of PET, CT, MRI, or ultrasound imaging techniques; a preoperative surgical plan developed by a clinical practitioner (for example, a surgeon), and a surface topology image dataset, optionally including texture data, of the rigid surgical structure of interest.

Figure 3A:
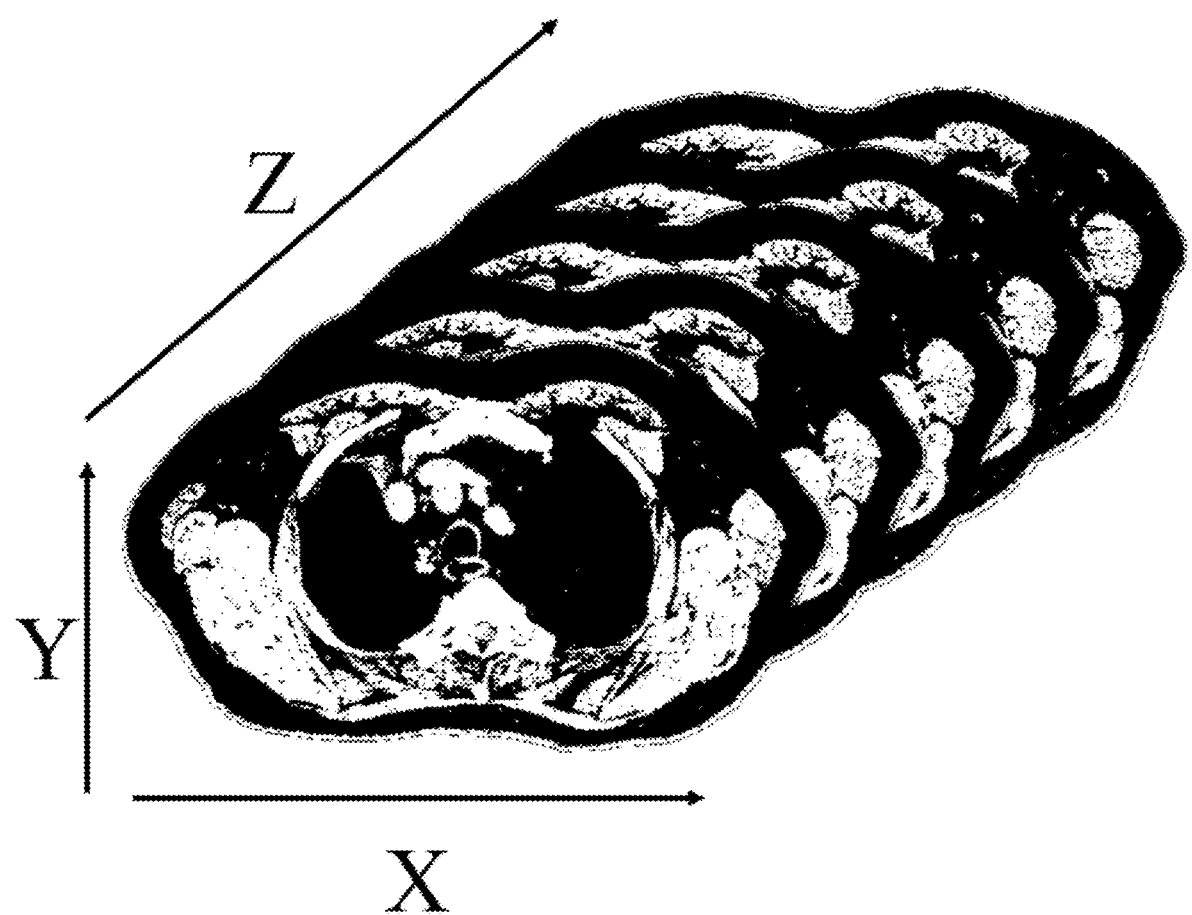
FIG. 3(a) is a sample 3D CT image dataset of a torso, preoperatively acquired from a subject, with X, Y and Z axes indicated.

In an example implementation, intraoperative CT imaging is used to acquire the preoperative image dataset. FIG. 3(*a*) illustrates exemplary CT image slices of the torso. Imaging modalities such as MRI, ultrasound, and other 3D imaging methods are also applicable for acquisition of preoperative image datasets. These image datasets can be used to develop a surgical plan for implantation of the surgical interventional device (e.g. a spinal cage or pedicle screw) into a desired position in the surgical structure of interest, and also serve as a reference dataset of a subject's anatomy.

The image data for the surgical structure of interest, for example, the spine, may be segmented before surgery and reconstructed as an image dataset for a rigid surgical structure. In several non-limiting examples, the structure can be a bone structure, such as a spinal column, a skull, a hip bone, a foot bone, and a patella. For example, FIG. 3(*b*) is a schematic of a posterior orientation of a segmented spine; FIG. 3(*c*) is a schematic of a lateral orientation of the segmented spine; and FIG. 3(*d*) is a schematic of a cross-sectional orientation of the segmented spine. The segmented surgical structure of interest image data serve as a template for registration with backscattered radiation topology data acquired intraoperatively. Example methods for segmentation are described in further detail below.

Incorporation of Surgical Plan

An example implementation of surgical guidance through the use of backscattered radiation topology imaging can include, for example, acquiring preoperative imaging data and developing a surgical plan, performing intraoperative imaging, and, in combination with the preoperative image data, generating useful information to guide surgery in the form of co-registered images, and displaying or otherwise communicating this surgical guidance information to a surgeon or operator. A preoperative plan can be developed, for example, by a clinician using the preoperative image data, and made available for use in the system. This example implementation enables repetition of intraoperative imaging and generating guidance feedback.

A preoperative surgical plan may consist of, for example, the desired position and orientation of pedicle screws defined with respect to a preoperative image data (e.g. CT, MRI) of the patient. The plan would be developed by a surgeon before a surgery, by analyzing the geometry of the vertebrae of interest, and selecting screws with the correct dimensions (e.g. length and radius) in accordance with the volume of the pedicle. The choice of screws and their positions would take into consideration the surrounding tissues to avoid damaging critical nerves and blood vessels or to make sure the screw does not breach the vertebral wall and enter the surrounding tissue. During surgery, the preoperative plan is updated to reflect the intraoperative geometry of a patient's spine with the optimal trajectory and a cone of acceptance, described below, as a guide to assist a surgeon during pedicle screw insertion.

System 100 may provide, through a display and/or user interface, guidance to assist in the placement of a surgical interventional device by providing intraoperative image feedback of changes in an orientation of a surgical structure of interest during the surgical procedure. By way of example and referring to FIG. 4, one example parameter, a cone of acceptance 25, can be used to improve accuracy of implantation of a pedicle screw into a vertebrae 23. The cone of acceptance 25 is defined by a range of trajectories relative to the vertebrae 23, along which the pedicle screw can be securely implanted into the pedicle canal without damaging the spinal cord 24, sparing the surrounding peripheral nerves and blood vessels, and does not protrude out of the bone. The range of available trajectories has limited lateral and angular freedom in light of the narrow middle section of the pedicle canal. Taken together, the trajectories collectively define a frustum conical shape with a wider end at an entry surface of the vertebral arch.

The range 28 of available trajectories relative to a vertebra 23 is dependent on: (1) the dimensions of the vertebra; (2) the orientation of the vertebra 23; and (3) the size of the pedicle screw. The cone of acceptance 25 incorporates the narrowest section of the pedicle canal, along a principle axis 26, for defining the optimal surgical implantation site for safe and secure pedicle screw insertion.

Figure 4:
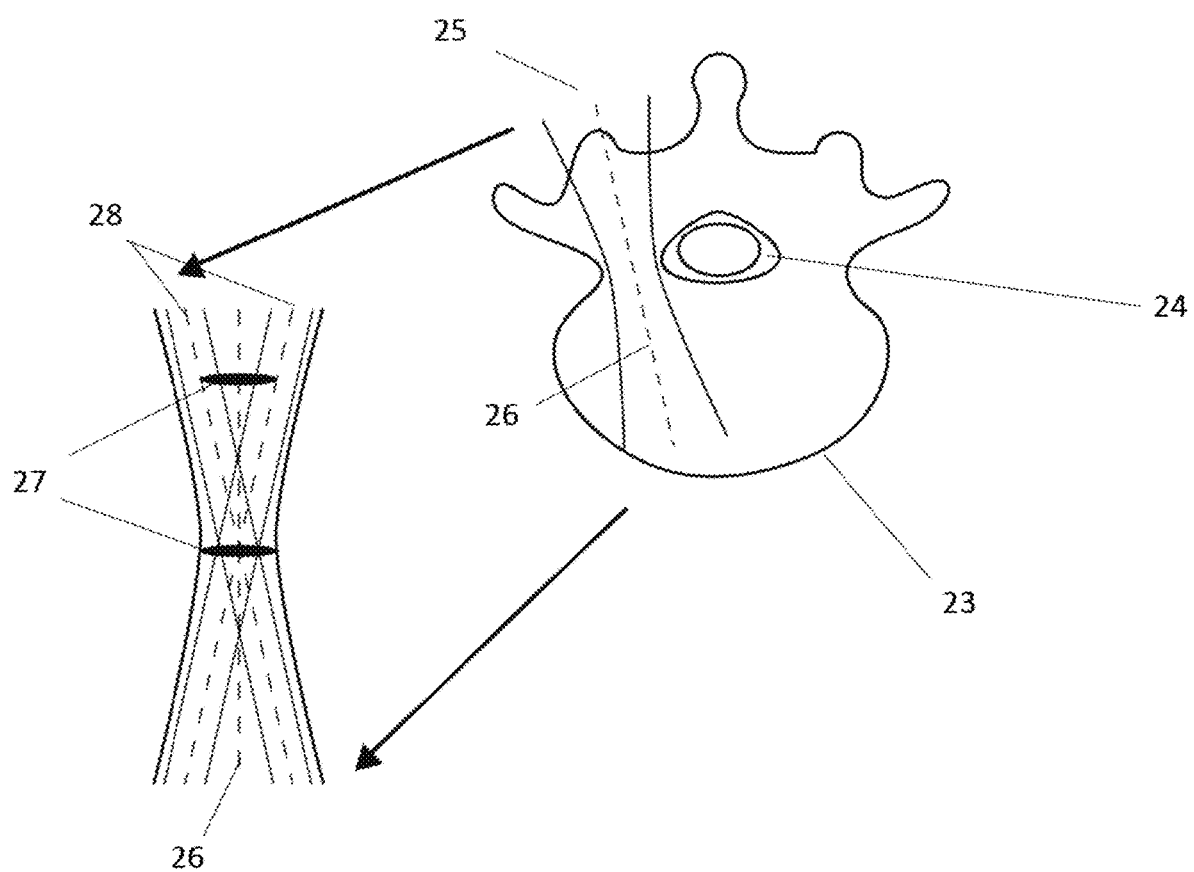
FIG. 4 illustrates an example implementation of a cone of acceptance provided in an example implementation of the image-guided surgical guidance system of FIG. 1A, and the location of the cone of acceptance relative to a vertebrae as an example surgical target for implantation of an interventional device.

The cone of acceptance 25 is typically determined as part of a preoperative surgical plan. Methods for incorporating the surgical plan into the intraoperative guidance system are addressed below. The system 100 monitors the orientation of the vertebra 23, which changes during surgery by a number of means, such as during drilling of the vertebra and depression of the spine by the surgeons, and generates guidance feedback, such as an update and display of the cone of acceptance 25, providing an example of motion correction. This example display of guidance feedback with motion correction is illustrated in FIG. 4. The center of the cone of acceptance is represented by a single trajectory referred to as the principle axis 26.

Figure 5:
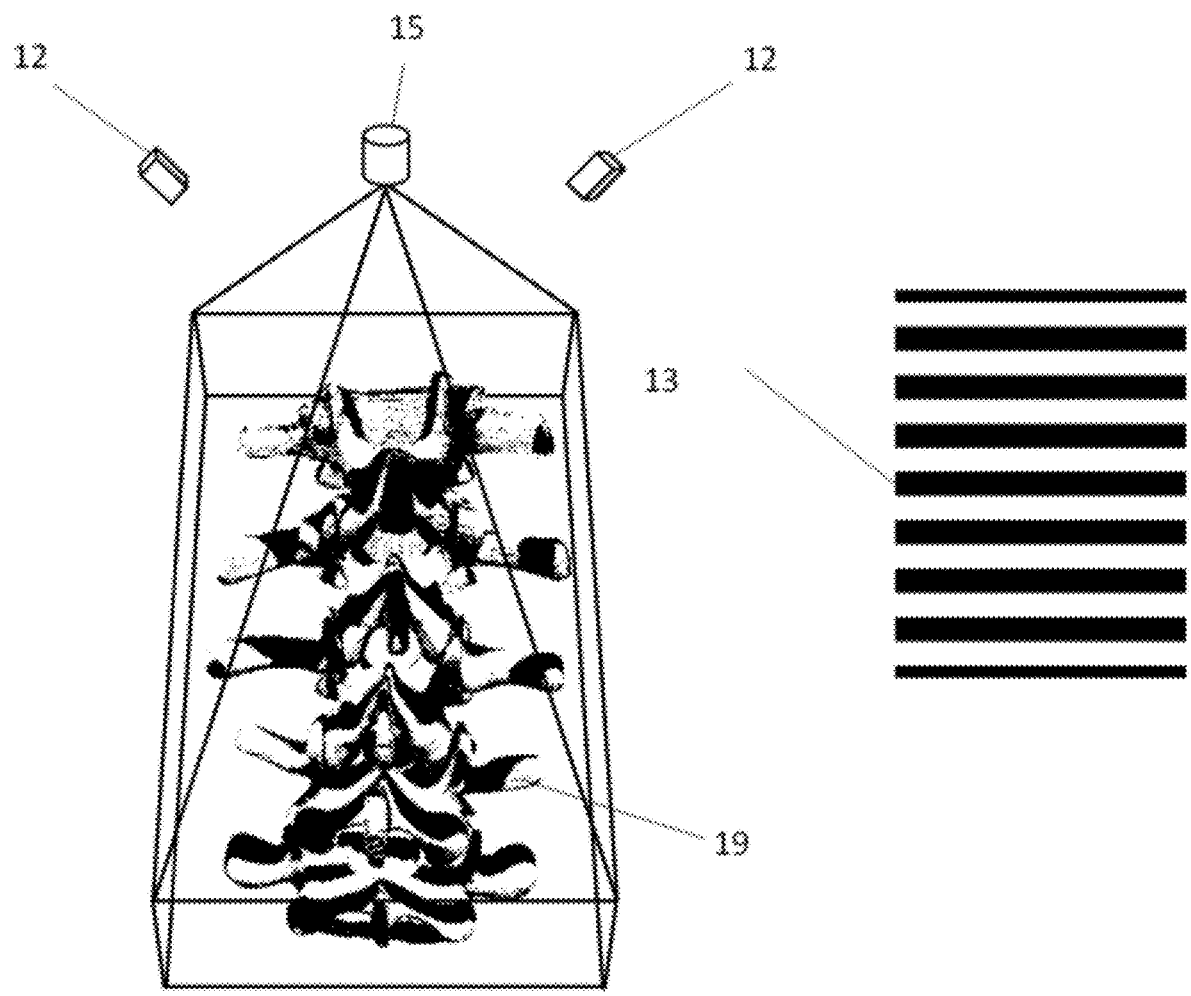
FIG. 5 is a schematic of the perspective view of an exposed spine onto which an example implementation of a binary stripe pattern is projected by a digital projector for structured light imaging.

FIGS. 5, 6(*a*) and 6(*b*) illustrate a schematic of acquisition of a topology map of the exposed spine 19 through illumination with a structured light grid pattern 13, via the digital projector 15 and two cameras 12. Imaging frame 20 houses digital projector 15 and the cameras 12. The use of a backscattered radiation topology system (in this example, using structured light) enables the dynamic tracking of the surface of interest, and optionally, the dynamic updating of a surgical plan, without requiring the use of a physical coordinate frame or fiducial markers being rigidly attached to the surface. It is to be understood that the structured light system need not include two cameras, and may be provided with a single camera.

The non-contact, fiducial-free detection of the surface of interest enables the dynamic tracking of the surface in an intraoperative environment. For example, referring to FIG. 6(b), the position of the vertebra 23 can shift to a new position 23' relative to the preoperatively determined position due to effects from surgical intervention (for example, pressure applied to the vertebra 23 as a finger of hand 29 is applied to the surface; such pressure could be provided or released by many other examples, such as a drill, not shown). An updated position of the vertebra 23' can be determined and outputted by the system 100 on the display 4. There is a concurrent shift in the principle axis 26 to an updated principle axis position 26' and also in the position of the spine 19 to an updated spinal column position 19'.

Figure 7:
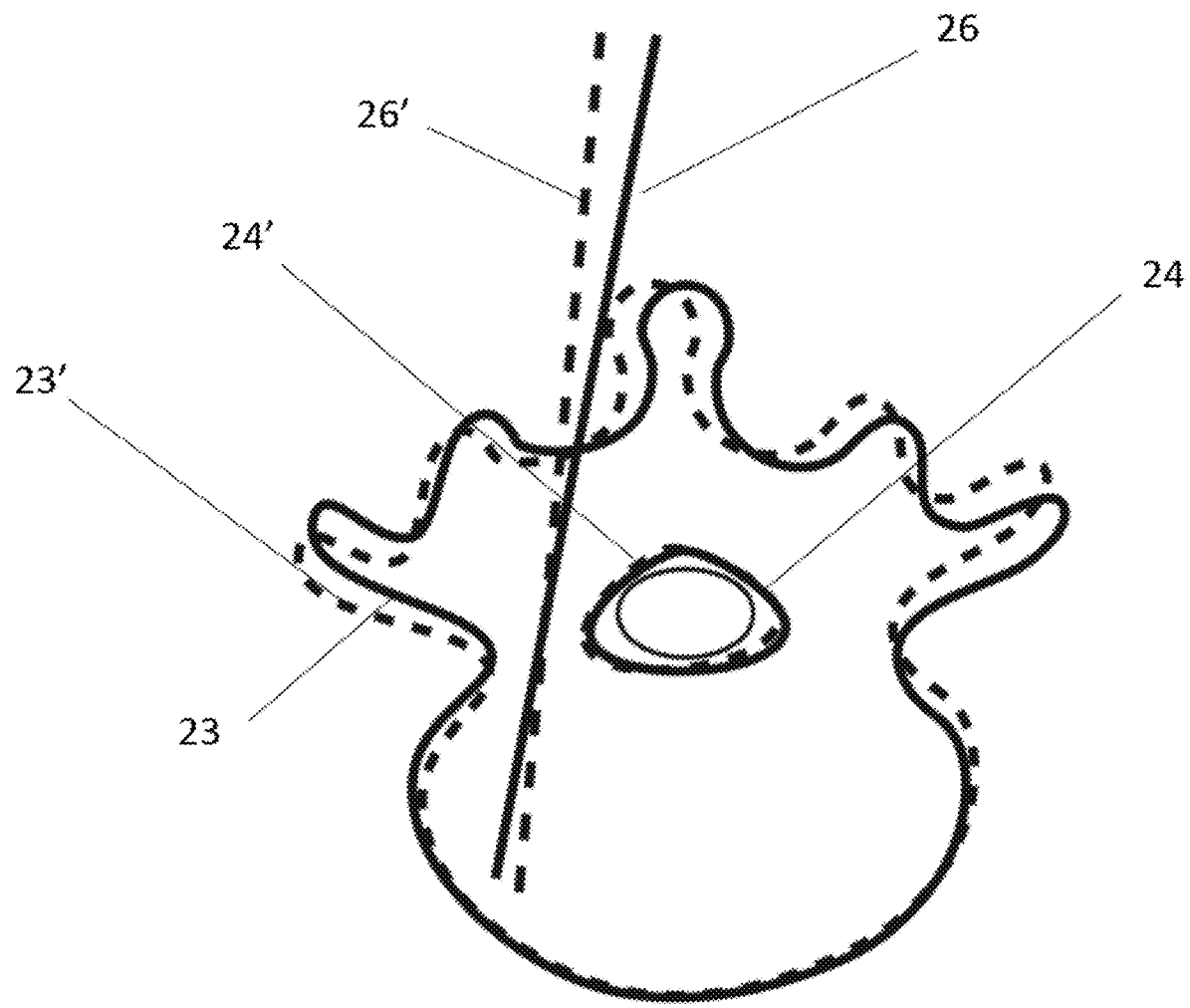
FIG. 7 illustrates an example implementation of correction of the principle axis of the interventional device due to physical displacement of a position (dashed line) of the vertebrae from the position determined in a preoperative plan (solid line).

Referring now to FIG. 7, an example shift in the position of the vertebra 23 from a preoperative position 23 to an intraoperative position 23' is illustrated. The vertebrae 23 preoperative position is used to develop the surgical plan. In developing the surgical plan, the principle axis 26 is determined to ensure avoidance of the spinal cord 24. The preoperative positions of the structures are indicated with solid lines. During surgery, positions can shift due to, for example, surgical intervention and change in subject position, as noted above. The updated locations of the target vertebrae 23', principle axis 26', and spinal cord 24' are determined by the system 100 and outputted on the display 4. Accordingly, system 100 provides a dynamically updated surgical plan that is registered to the patient anatomy in real-time.

Intraoperative image updates of the vertebrae 23 can be provided continuously or discretely according to input into the system 100 by, for example, a surgeon. In the situation where updates are provided continuously, the system 100 can operate autonomously obviating the need for the surgeon to input any additional data. In the situation where updates are provided discretely, for example updates provided at single time points, the surgeon can request an image data update by inputting a request into the system 100. The updated plan is provided on the display device 4 on command without any other user interface. The updated image data and related updated intraoperative surgical plan enable a surgeon to accurately implant, for example, a pedicle screw into a vertebra 23.

In one example, the surgical plan may include surgical criteria that can be displayed on the co-registered image. Examples of criteria that the surgeon may input into system 100, as part of a surgical plan, include, but are not limited to: the accepted accuracy of screw placement; the coordinates of the point of entry into the vertebra 23 that define the principle axis 26; the accepted angle of screw placement; and the depth of screw placement.

Referring to FIG. 4, these criteria can be used to calculate a plane of smallest diameter (for example the narrowest section of the pedicle canal), through which the principle axis 26 runs centrally. Due to the spatial registration between the surface of interest and the projector, the calculated plane 27 can then be projected onto the surface of the vertebrae via the projector to provide a desired solution for pedicle screw placement 28. The cone of acceptance 25 coordinates can then be overlaid onto the vertebrae and provided on the display 4. The system 100 can remain in "standby mode" until the structure of interest is surgically exposed.

Surface Detection and Image Registration for Intraoperative Guidance

Figure 8:
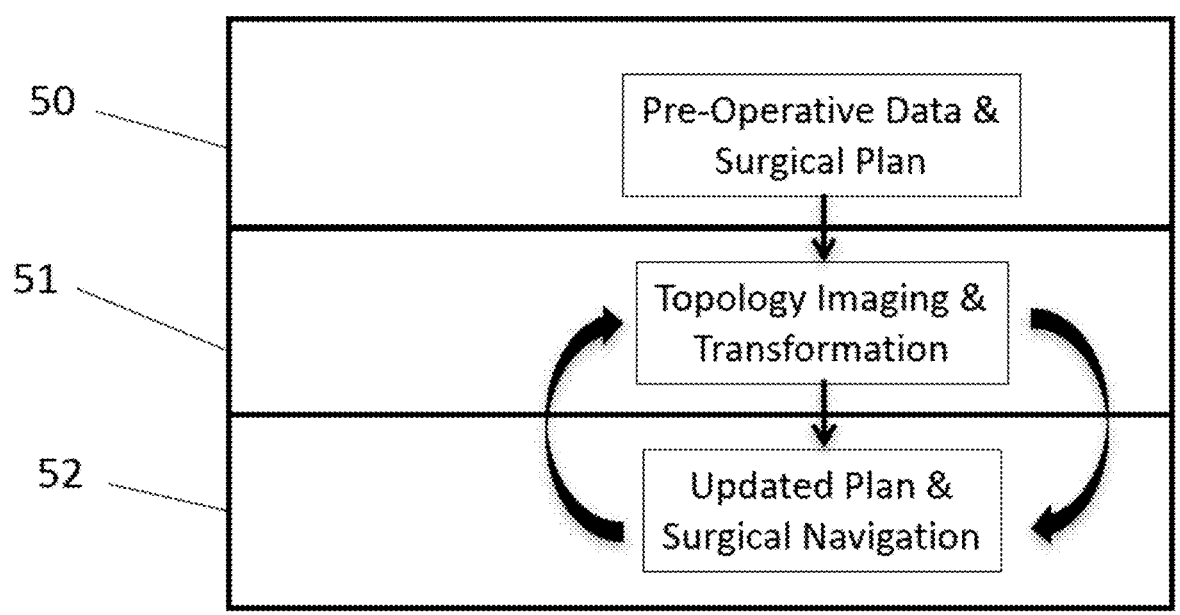
FIG. 8 is a flow diagram illustrating an example implementation of a method of intraoperative surgical guidance.

Referring now to FIG. 8, an example method performing image registration and guidance using a backscattered radiation surface guidance system is illustrated. As described above, optical topology imaging and surface topology image data processing algorithms are employed to track the location and orientation of a rigid structure of interest during a surgical procedure. While the examples below relate to orthopaedic surgical procedures, it is to be understood that the methods may be applied to a wide range of surgical procedures and other applications.

As shown at step 50 in FIG. 8, the method initially involves obtaining preoperative image data acquired by any one of a number of imaging modalities, and optionally developing a preoperative surgical plan. Intraoperative topology imaging data is then acquired in step 51 and registered to the pre-operative image data for providing guidance feedback to guide the surgical procedure intraoperatively. In step 52, a surgical plan may be updated based on a shift in the position of the structure of interest as detected by system 100. Steps 51 and 52 are repeated as necessary during a surgical procedure. This method is described in further detail below, with reference to FIGS. 9 to 17.

(i) Preoperative Image Acquisition and Surgical Planning Module

Figure 9:
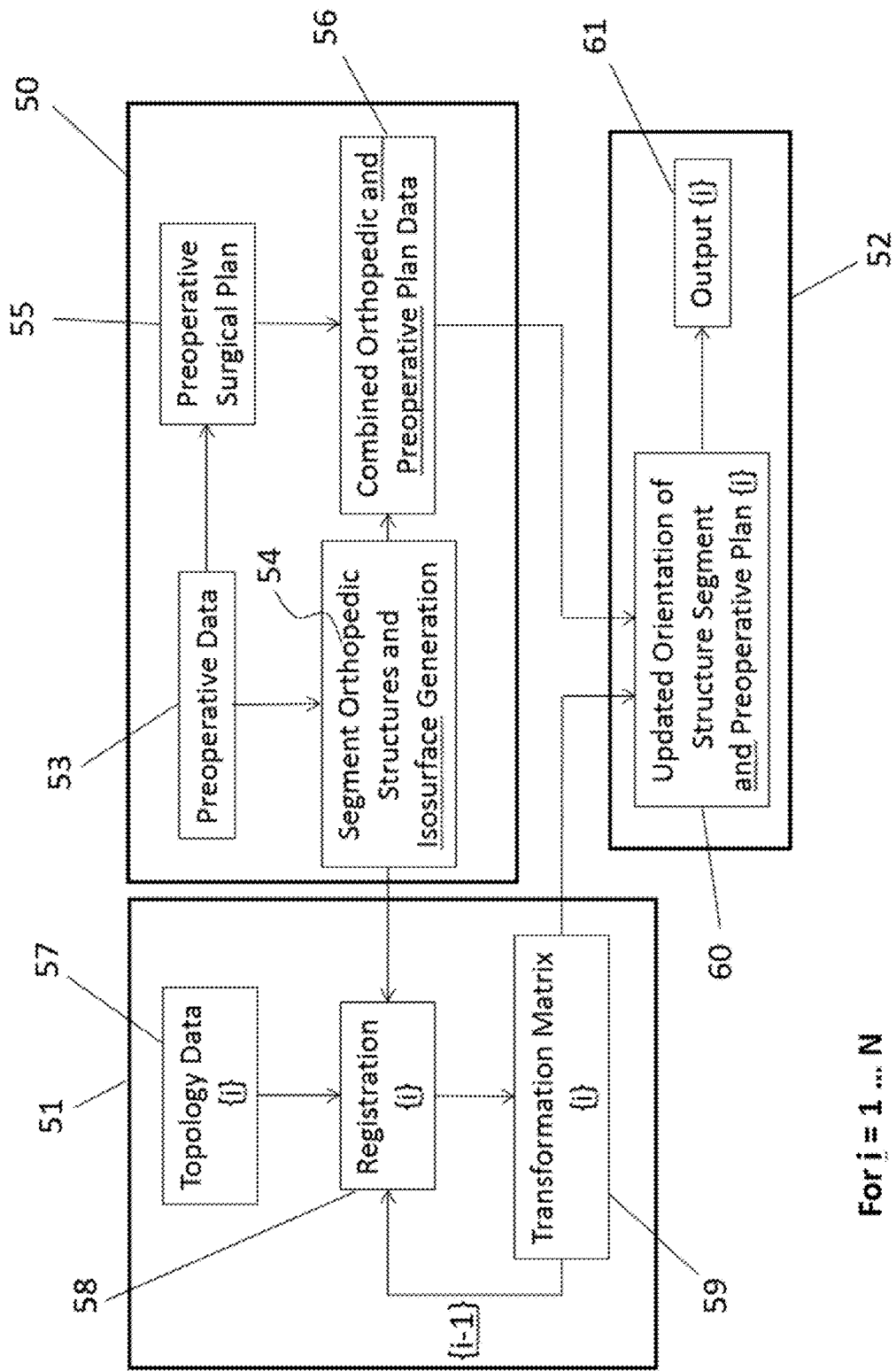
FIG. 9 is a detailed flow diagram of a method of intraoperative surgical guidance.

Referring to block 50 of FIG. 9, a 3D image dataset is acquired preoperatively to locate an anatomical region of interest by any one of a number of 3D imaging modalities, including, but not limited to, MRI, CT, and ultrasound. Certain imaging modalities may be more suitable for a given surgical context depending on the primary target of interest. For example, CT imaging is suitable when the primary target of interest is the spine. The spine is segmented from the 3D images for intraoperative image registration. The individual vertebrae are segmented, which can include labeling, either automatically or manually, with the correct anatomical location. Individual vertebrae parts (e.g. the laminar or pedicle) may be further segmented for implantation device (e.g. pedicle screw) placement planning. These steps of segmenting the individual vertebra are further described below.

In step 53 of the example method shown in FIG. 9, the preoperative image data of the orthopaedic structures of interest is acquired (for example, a CT scan of the patient's spine). The CT image dataset is processed to generate image data of one or more surfaces, such as an isosurface. The processing results in preoperative image data that can be, for example, a polygonal mesh output data of the spine (sometimes referred to herein as CT_MESH_FULL). Isosurface generation can, for example, use a predefined threshold parameter distinguishing differential based tissue density, such as bone, compared to soft tissue density.

A preoperative plan is then developed in step 55 and made available to system 100, using the preoperative surface image data (CT_MESH_FULL) to determine and record the planned location and orientation of a surgical intervention device. The preoperative plan can, for example, also specify acceptable error associated with each intervention.

The preoperative image data for the orthopaedic structure is then, in step 54, segmented (manually or automatically) into structure segments that have rotational and translational degrees of freedom with respect to one another (e.g. individual vertebrae). Segmentation can be performed manually, for example, by a radiologist, or with the aid of semi-automatic tools. Regardless of the segmentation method, the output of this step provides a given number, N, of preoperative surface image data segments (sometimes referred to herein as CT_MESH_OB_1 . . . CT_MESH_OB_N). The segmented image data are made available to the system.

The segmented preoperative image data can then be registered to the preoperative plan in step 56. Each segment is registered to the associated aspect of the plan. It is to be recognized that multiple aspects of plans could be registered against one segment (for example, two pedicle screw holes in a vertebrae) and still further aspects of plans could be registered against multiple segments (two pedicle screw holes registered on one segment, and two screw holes on another segment). Surgical guidance feedback could be provided on the various aspects independently as needed, or simultaneously. For example, the surgical intervention for the plan can include an entire device and attachment points. As a further example, the surgical intervention can include planned attachment points or principle axis only, such as one or more drill holes or cut lines.

The combined orthopaedic and preoperative plan data, as described above, thus includes the segmented preoperative image of an orthopaedic structure and a preoperative plan allowing this combined representation to be rotated and translated as desired.

(ii) Topology Data Acquisition and Dataset Manipulation Module

Backscattered radiation surface topology data of the exposed structure is obtained in step 57 of FIG. 9. The topology data can be captured continuously or on demand. Each of the preoperative image data orthopaedic segments can be registered to the backscattered radiation topology scan in step 58.

Figure 10:
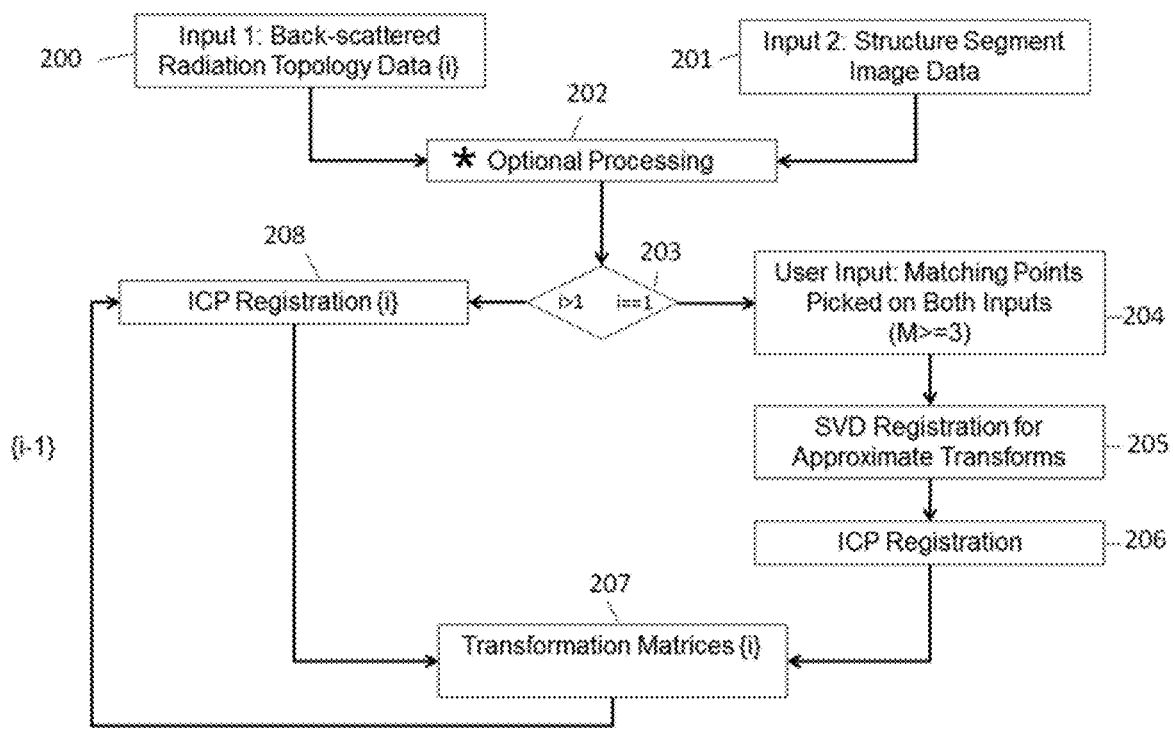
FIG. 10 is a flow diagram of an example implementation of a method algorithm for generating a transformation matrix for use in image dataset registration

One particular example method for the registration, as shown in the flow chart provided in FIG. 10, is based on iterative closest point (ICP) registration, which is one of the most commonly used surface registration techniques. ICP registration technique requires two inputs: backscattered radiation topology data 200 and structure segment image data 201. Dependent on the imaging scenario, these data can initially go through an optional processing 202 step to remove clutter or to identify specific components. This clutter removal step is described further below. Other suitable methods of surface registration are described in Chen and Medioni (Y. Chen and G. Medioni, "Object Modeling by Registration of Muliple Range Images", Proc. IEEE Conf. on Robotics and Automation, 1991) and Besl and McKay (P. Besl and N. McKay, "A Method for Registration of 3D Shapes", IEEE Trans. Pattern Analysis and Machine Intelligence 14 (1992), 239).

ICP is suitable for relatively small transformations when using complex point clouds. Thus, a coarse estimate of the transformation must be made initially on the first pass through the algorithm $\{i==1\}$ 203. For this purpose an interactive point-based approach can, for example, be used to derive the initial transformation T_initial in steps 204 and 205. For example, M (where M>=3) representative points are selected from each of the segmented isosurface image datasets (CT_MESH_OB_1 . . . CT_MESH_OB_N), where these matched points serve as virtual fiducial markers in both the CT isosurface and backscattered radiation surface topology datasets 204. Using a singular value decomposition algorithm 205, the M points can be brought into alignment providing an initial transformation for a more precise registration using the high-resolution dataset, for example, as described in Salvi (J. Salvi, "A Review of Recent Range Image Registration Methods with Accuracy Evaluation", Image and Vision Computing 25 (2007) 578-596). Alternatively, this initial alignment can be performed using the method described in Berthold K. P. Horn (1987), "Closed-form solution of absolute orientation using unit quaternions". Next, each of the vertebrae 23 meshes (CT_MESH_OB_1 . . . CT_MESH_OB_N) is registered to the backscattered radiation datasets using ICP in parallel with T_initial as an initial condition for the transformation 206.

Although T_initial, the initial transformation, can be derived for each iteration, a possible implementation includes obtaining T_initial only once. For each new backscattered radiation dataset $\{i>1\}$ 203 that is acquired, the last transformation matrix $\{i-1\}$ calculated 207 for the vertebrae 23 of interest can be used as the starting point for the new registration 208, rather than the original registration as the starting point, saving memory, computation time, and reducing overall algorithm complexity.

Figure 14:
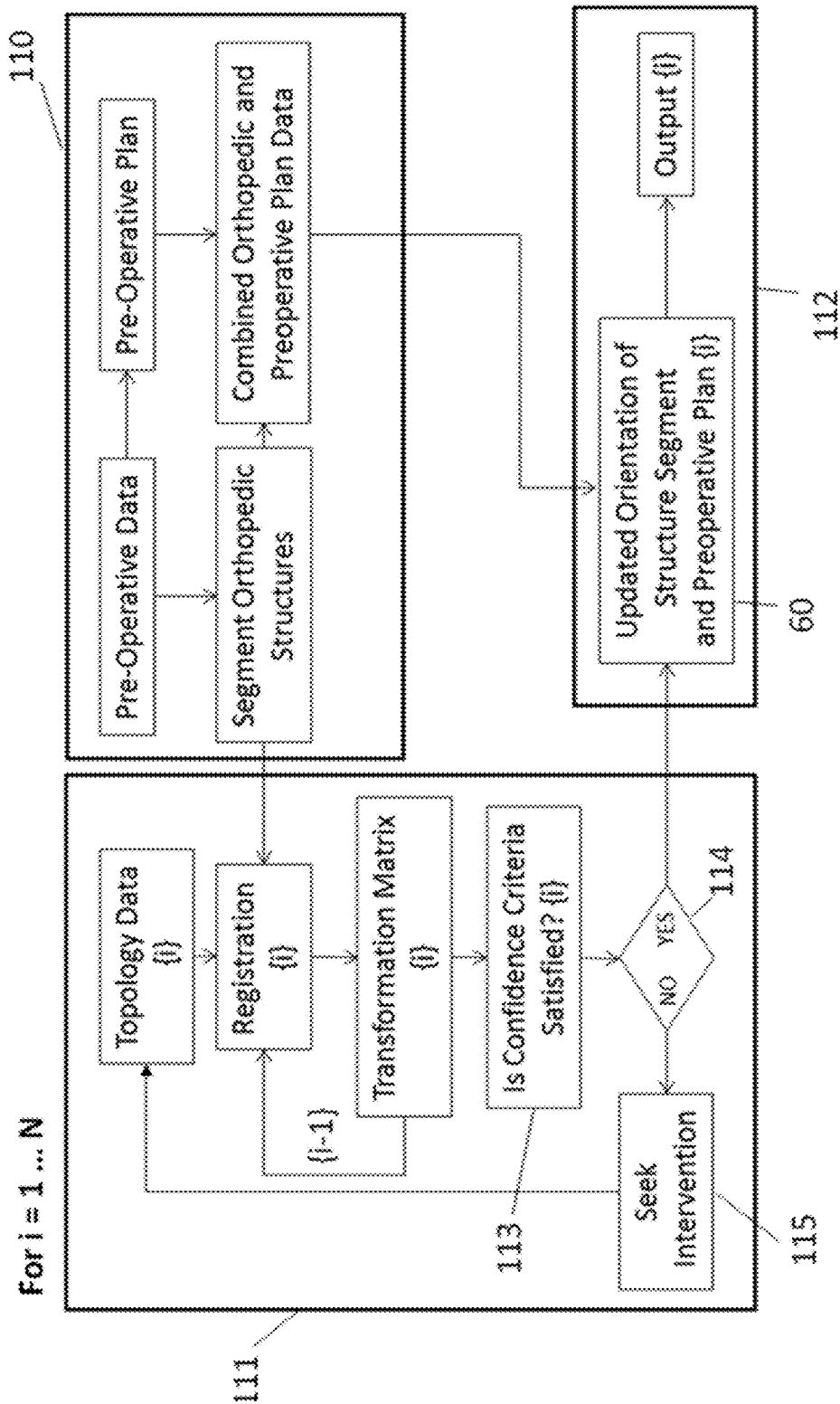
FIG. 14 is a flow diagram of an example implementation of a method of intraoperative surgical feedback guidance, including error checking and corrective intervention.
Figure 15:
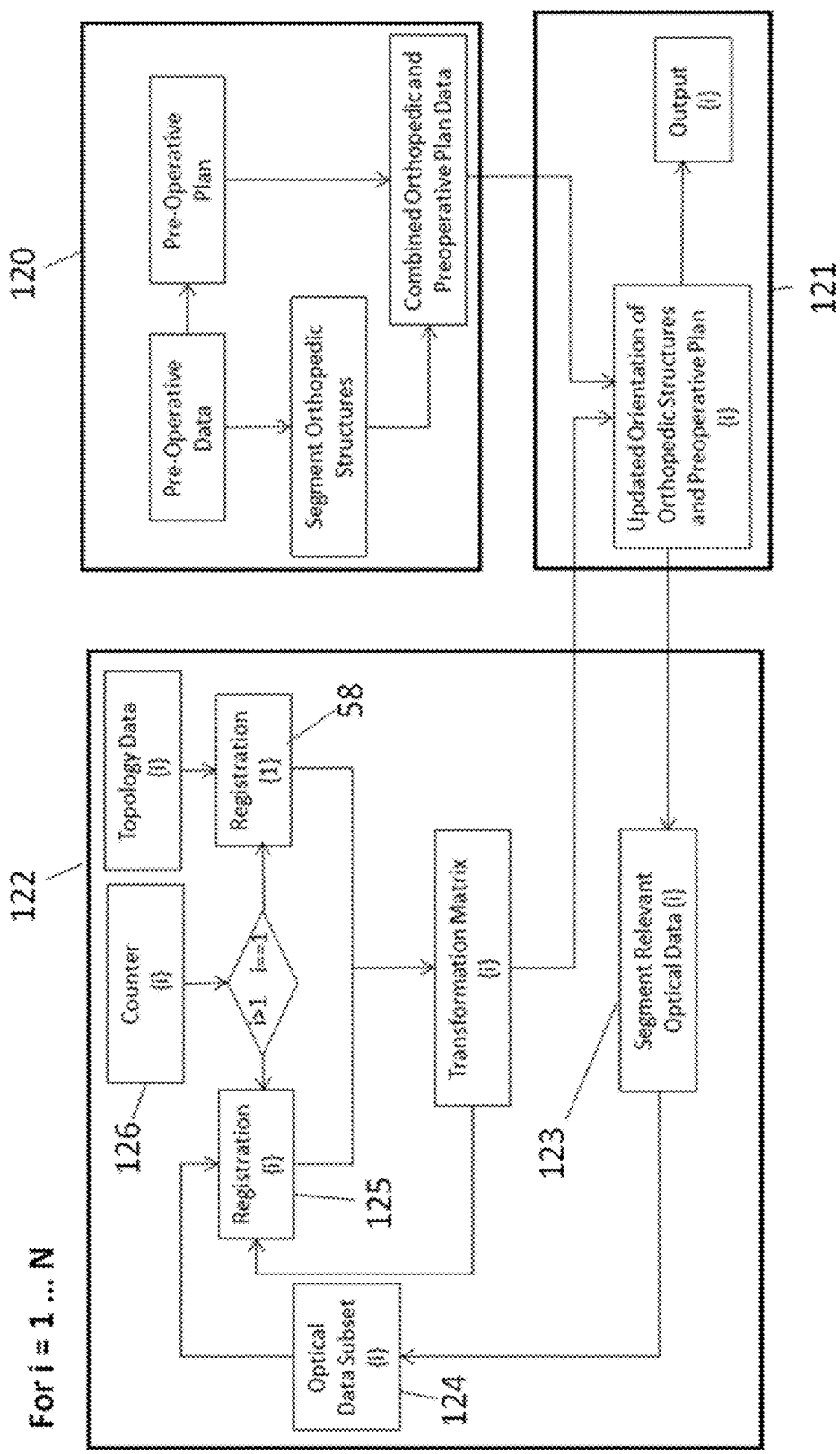
FIG. 15 is a flow diagram of an example implementation of a method of intraoperative surgical feedback guidance including registration using a subset of points of captured image data.

An example implementation to improve processing speed during intraoperative guidance involves utilizing a subset of points from the image data instead of the complete point cloud (complete image dataset) for image registration, as shown in FIGS. 14 and 15. These points may be selected automatically by analyzing the topology map for unique features that best represent a target structure of the body. For instance, surfaces greater than a predefined curvature may be used (i.e. pointed surfaces).

The method of sub-sampling is further described as follows. Let $P=\{p_1, p_2, \ldots, p_m\}$ and $Q=\{q_1, q_2, \ldots, q_n\}$ be the two surfaces to be registered, with m and n points respectively. For this example, the surface P will be aligned towards Q. Finding matching points between these 2 surfaces requires that for each point in P, a corresponding closest point is located in Q. In the simplest case, all the points in P are matched to a point in Q. However, due to the density of points available in the surfaces, practically, only a subset of the points in P is needed for point matching without significantly affecting the accuracy of the registration. The main advantage of sub-sampling the data is a decrease in the time required for computing the registration. Furthermore, it can also act as a step to select relevant features from the surfaces, as further described below, and as described by Rusinkiewicz and Levoy (Efficient Variants of the ICP Algorithm (3DIM 2001):145-152, Quebec City, Canada, (May 2001)).

According to one example method, the points on a given surface may be selected randomly until a minimum number of points are reached.

Figure 20:
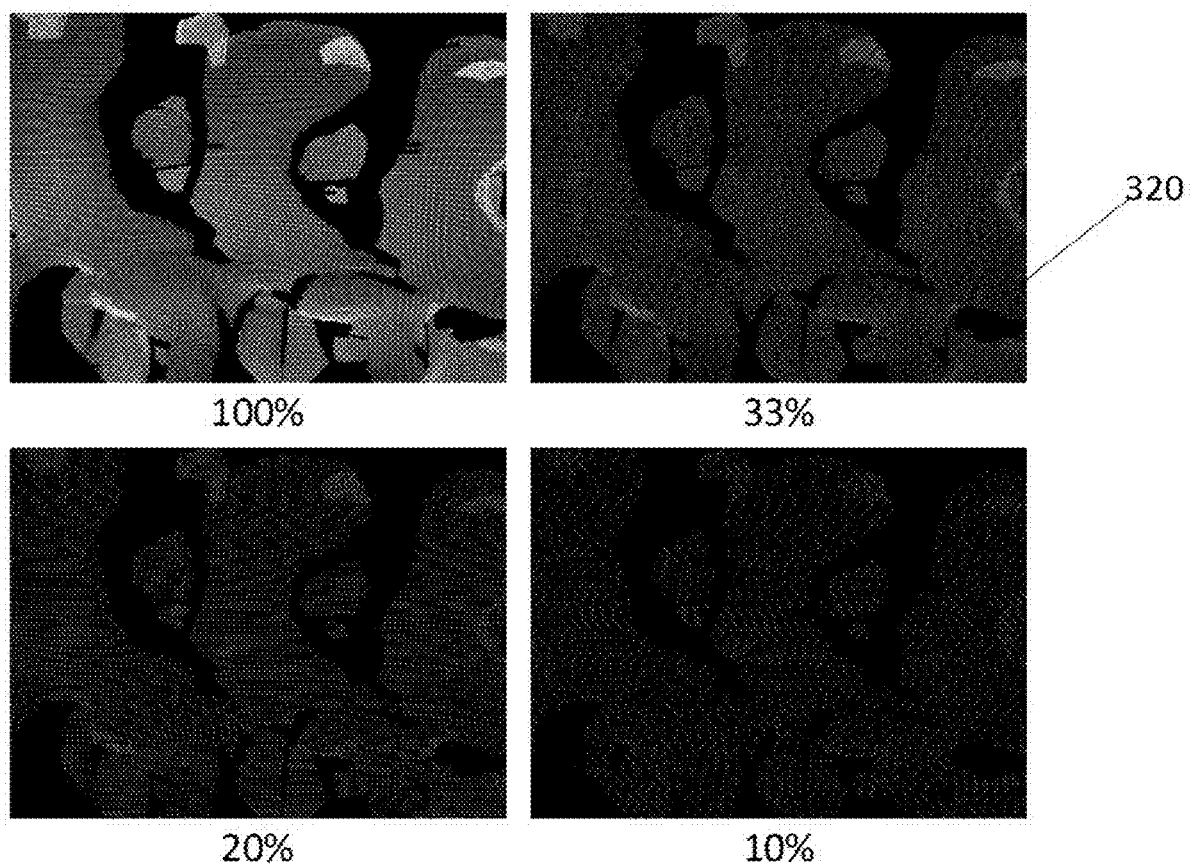
FIG. 20 displays the points, which make up the surface of a spine phantom acquired through optical topology, where these points are uniformly down sampled by spatial position.

Following another example, given the three-dimensional (3D) position of the points (the x, y, z coordinates), the subset of points may be selected so that they are uniformly sampled in space. FIG. 20 demonstrates an example of this uniform down sampling by spatial position, where the percentage (100%, 33%, 20%, 10%) 320, represents the remaining points post-down sampling. In the Figure, the points which make up the surface of a phantom spine acquired through optical topology are down sampled uniformly by spatial position.

Figure 21:
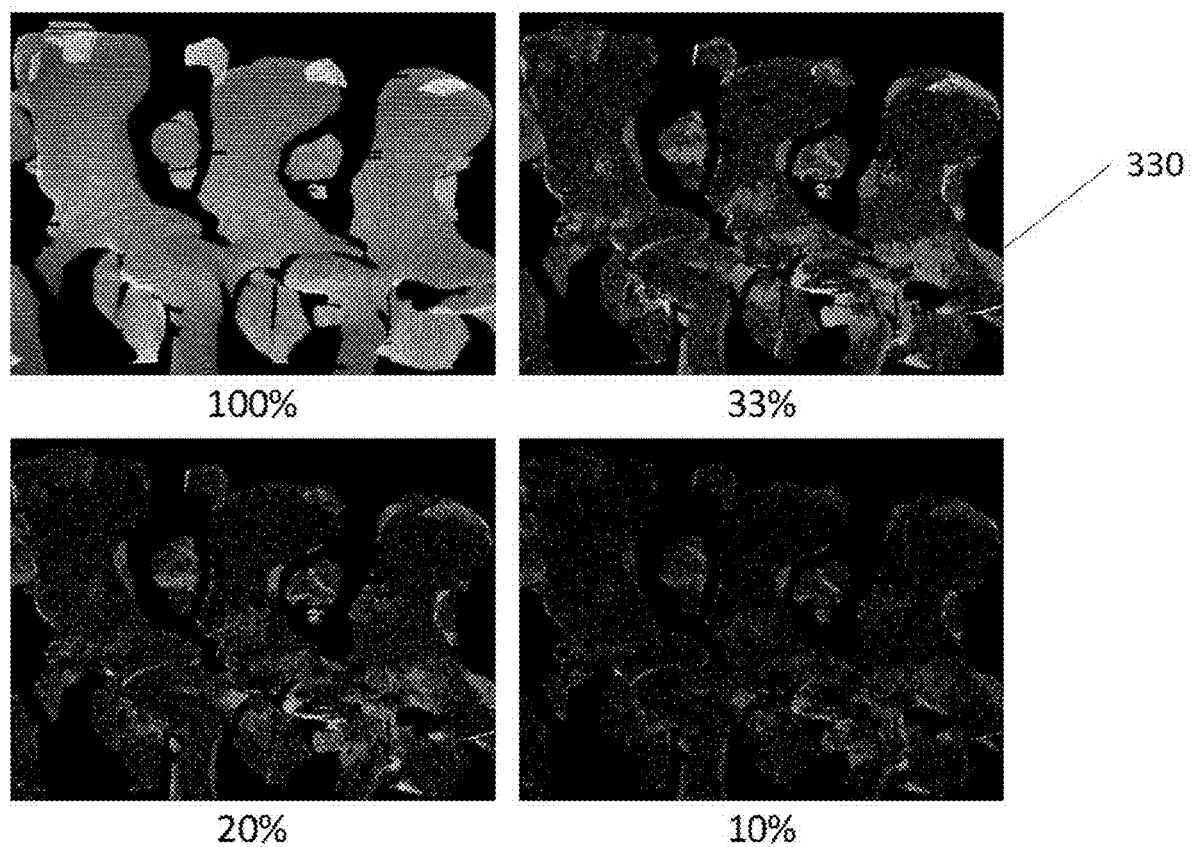
FIG. 21 displays the points, which make up the surface of a spine phantom acquired through optical topology, where these points are uniformly down sampled by normal vectors of the corresponding points.

In a third example method, each point in the surface has a corresponding normal. The normal is a vector that is perpendicular to the tangent plane of the surface at that point. Instead of using the spatial location (as in the preceding example), sampling can be performed based on the distribution of the normal vectors. FIG. 21 shows an example of this uniform down sampling using normal vectors of corresponding points, where the percentage (100%, 33%, 20%, 10%) 330, represents the remaining points post down sampling. As demonstrated in FIG. 21, the surface of a phantom spine, acquired through optical topology, is down sampled uniformly by normal vectors of the corresponding points. In this case when the surface topology is relatively slowly varying (i.e. smooth), this method can assign more points to prominent surface features. Therefore, it can improve the accuracy of registering surfaces that are mostly smooth with sparse features.

The output from the registration process can be a transformation matrix including translation and rotation identities, such as, for example roll, pitch and yaw, for each of the segmented structures. For example, translation identities can be present on an x, y, z coordinate system with rotation represented by roll, pitch, and yaw identities. It is recognized that different transformation matrices can be based on alternative coordinate systems.

The transformation matrices derived can be applied to the combined segmented orthopaedic structures and corresponding registered preoperative plan to update and to match the orthopaedic structures to the preoperative plan. This updated structure and plan can then be output in the form of images, with optional text, for example, descriptive text relating to relative distances and/or orientations. The output can be on a hardware display, such as a monitor or a head mounted display. Images can be displayed, for example, as slices in two dimensions or in a three-dimensional perspective view to provide guidance feedback. Such surgical guidance feedback can be used, for example, by a surgeon intraoperatively to assist in guiding an orthopaedic procedure. An example includes the presentation of motion correction to the surgeon as a pedicle screw is inserted into a vertebra (as shown in FIG. 7).

Example Implementation of Guidance System for Spinal Surgical Procedure

An example implementation of the surgical guidance system 100, including image registration, will now be described. This operational description is based on a structured light example for implantation of a pedicle screw in a vertebra of the spine. If other techniques are used, the operation can vary as individual components of surface topology acquisition of backscattered radiation are different. For instance, if topology is acquired via a laser range device, the projector 15 can be replaced by a laser range finder. This operational description is by no way limiting, and serves as an example as to how an example guidance system can operate.

Figure 12:
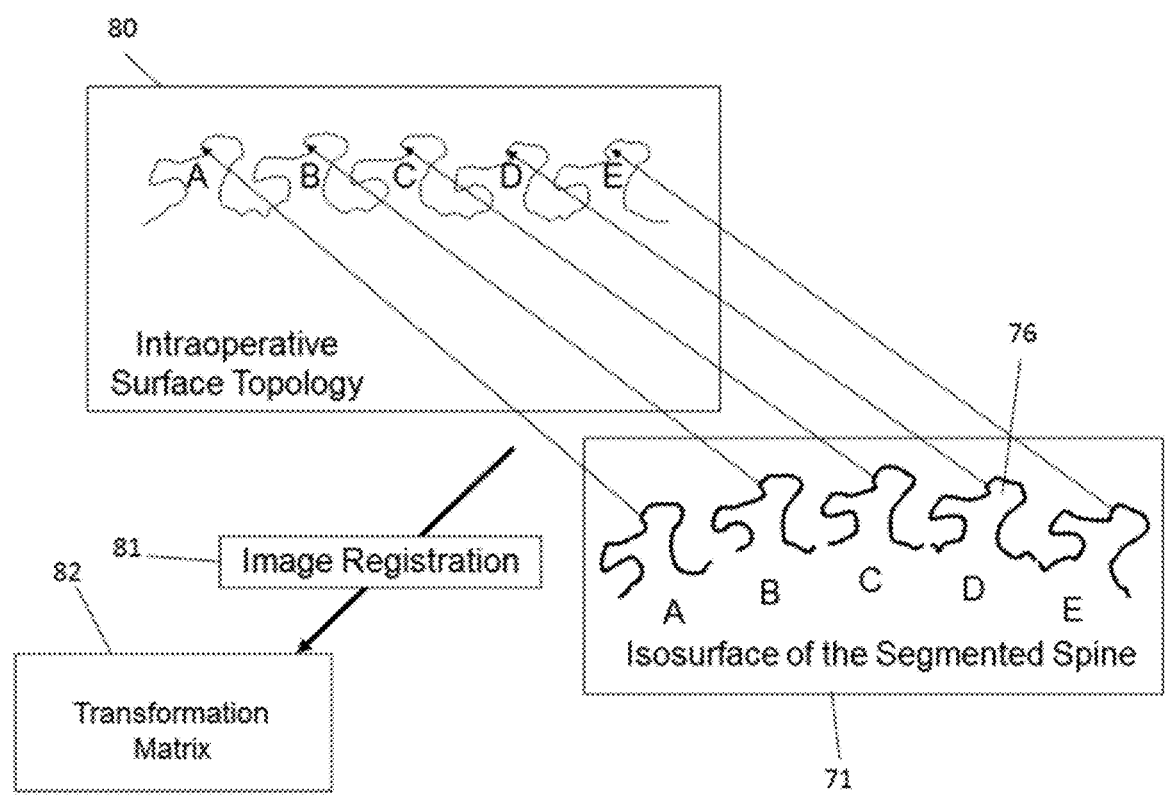
FIG. 12 illustrates an example implementation of updating of a preoperative surgical plan for use in a method of intraoperative surgical guidance.

Prior to surgery, the preoperative image dataset of the spine is acquired via an imaging modality such as CT. The surgical plan is developed by the surgeon based on the preoperative image data, which are inputted into the operator workstation 7 via the user interface 5. A sample preoperative image dataset 72 is illustrated in FIG. 12. These data are segmented and labeled preoperatively 70.

The surgical guidance controller 3 receives and inputs backscattered radiation image datasets acquired via the digital projector 15. A sample surface topology image dataset 71 is illustrated in FIG. 12. As will be described below, the preoperative image dataset is processed by the surgical guidance controller 3 to provide, for example, real-space spatial relationships between the surgical structure of interest and the preoperative 3D image dataset and preoperatively developed surgical plan 73 to provide current (e.g. real time) intraoperative data with respect to the vertebrae 23.

The surgical plan data may be inputted manually by a surgeon or other operator and uploaded by the system 100. Data regarding the segmentation of the structure of interest (e.g. a portion of the spine 19) can be manipulated by the system 100 upon user instruction via the user interface 5, such as a keyboard, and subsequently processed by the surgical guidance controller 3. Such segmentation methods are known to those skilled in the art. The system 100 can process this data to output posterior, lateral, and cross-sectional views of the spine region to the operator on the display 4. Alternatively, the surgical plan can be developed by a surgeon using a computing device, such as a personal computer, in advance of the surgical procedure, and the surgical plan can be uploaded to the user workstation 7 prior to surgery. The user workstation 7 is provided in the operating room during the surgical procedure.

The system 100 may then be employed to segment the spine 19 to focus on the target vertebra 23 into which the pedicle screw will be implanted. Example methods for performing this step are provided below. In the present non-limiting example in which the surgical plan involves the placement of a pedicle screw, the preoperative surgical plan is provided in order to identify an entry point of the pedicle screw into the vertebra 23. The physical dimensions of the pedicle screw (i.e. size, thread count, etc.) are taken into consideration by the surgeon to avoid surrounding organs and tissues (i.e. spinal column 24 and/or bone exit). The calculated surgical coordinates may be inputted into the system manually by the user via the user interface 10 and then processed by the surgical guidance controller 9 to output the "cone of acceptance" 25 coordinates.

Once the vertebrae are surgically exposed and the field of view clear, the process of surface topology image acquisition of the vertebrae is initiated, for example, by user input. Referring to FIG. 1(b), projector 15 emits light onto the exposed spine 19 in the form of the structured light grid pattern 13. The cameras 12 acquire the surface topology image as part of surface topology system 1. The preoperative plan and surface topology image dataset for the vertebrae along with the planned pedicle screw orientation are then displayed on display 4, as shown in FIG. 6(a). The surgeon can then proceed to begin the surgical procedure based on the information displayed.

Figure 6B:
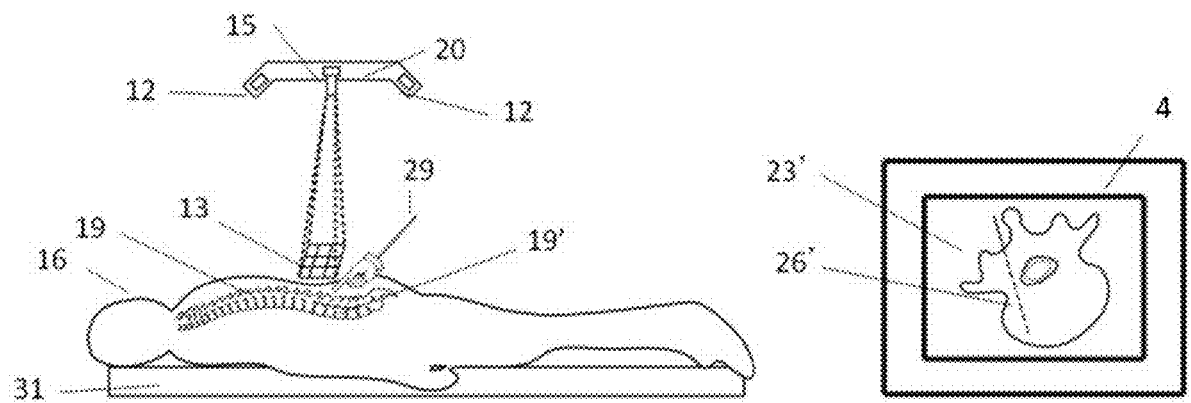
FIG. 6(b) illustrates an example implementation of intraoperative image acquisition of a spine of a subject and output including an updated principle axis identified by the surgical guidance feedback system.

System 100 may acquire surface topology information pre-operatively as well as intraoperatively. FIG. 12 illustrates a combined surgical plan 73 that integrates the preoperative image data 72 with the intraoperative surface topology data 71. In performing the surgical procedure, a surgeon can apply pressure to the vertebrae, causing the preoperatively determined position of the vertebrae to be physically displaced to a new position. Other external factors that can cause a shift in the vertebrae during the surgical procedure include movement of the subject or change in position of the spine relative to the position determined from the preoperative CT scan data. The shift in position of the vertebrae results in a physical displacement of the principle axis 26, which is used to guide pedicle screw placement during the surgical procedure. There is an inherent potential for error in the position of pedicle due to such a shift, and the error can result in pedicle screw exit from the bone or infiltration of the pedicle screw into the spinal cord. The registration and transformation methods disclosed herein support updating intraoperative image data and, optionally, a surgical plan, to compensate for the induced displacement, as shown in FIG. 6(b).

Referring now to FIG. 9, once a preoperative imaging dataset is acquired in block 53, the orthopaedic structures (e.g. individual vertebrae) are segmented in block 54 from the preoperatively acquired CT image dataset. Suitable segmentation algorithms are known to those skilled in the art. For example, a suitable segmentation algorithm is as described by Yiebin Kim and Dongsung Kim (Computerized Medical Imaging and Graphics 33(5):343-352 (2009)). The segmentation algorithm may extract information about the vertebrae 23 from the spine in four main processing modules: (1) pre-processing, (2) inter-vertebral disc search, (3) 3D fence generation, and (4) fence-limited labeling, as further described below.

In the first processing module, namely the pre-processing module, features such as 3D valleys are detected and valley-emphasized Gaussian images are outputted. Gradients may be used, however, valleys can provide better features than gradients in separating two closely separated objects because they appear in the middle of two adjacent objects, while the gradients are detected at the boundaries of every object. The steps involved in the pre-processing module include: i) detection of a 3D morphological valley, ii) generation of a valley emphasized dataset, iii) generation of an intensity based threshold, and iv) generation of x a 3D Gaussian filter, as described in Kim and Kim (Kim and Kim, (2009) Computerized Medical Imaging and Graphics 33(5): 343-352).

An inter-vertebral disc search module automatically may be employed to extract the spinal cord and detect inter-vertebral discs along the center line of the spinal cord. The steps of the inter-vertebral disc search module include: i) extraction of the spinal cord using an iterative sphere growing algorithm; and ii) extraction of the intervertebral discs by determining the center of each sphere, which consists of the extracted spinal cord defining the center line C(t) of the cord, and the intensity profile in the plane, which is normal to the center line, as described by Kim and Kim (Kim and Kim (2009) Computerized Medical Imaging and Graphics 33(5):343-352).

The 3D fence generation module generates boundary surfaces, used to separate one vertebra from another. In generating the 3D fence, an erroneous curve that is derived from a local minimum in the optimization process is detected with an evaluation method and then corrected by a minimum cost path finding method, which can then find the global minimum. The steps in 3D fence generation include: i) generation of a 2D intervertebral segmentation curve; ii) propagation of the 2D curve into a 3D surface; and iii) detection and correction of any erroneously propagated curves, as described by Kim and Kim (Kim and Kim (2009) Computerized Medical Imaging and Graphics 33(5):343-352). The results of automated segmentation can be reviewed by a surgeon prior to being inputted into the system.

Figure 11:
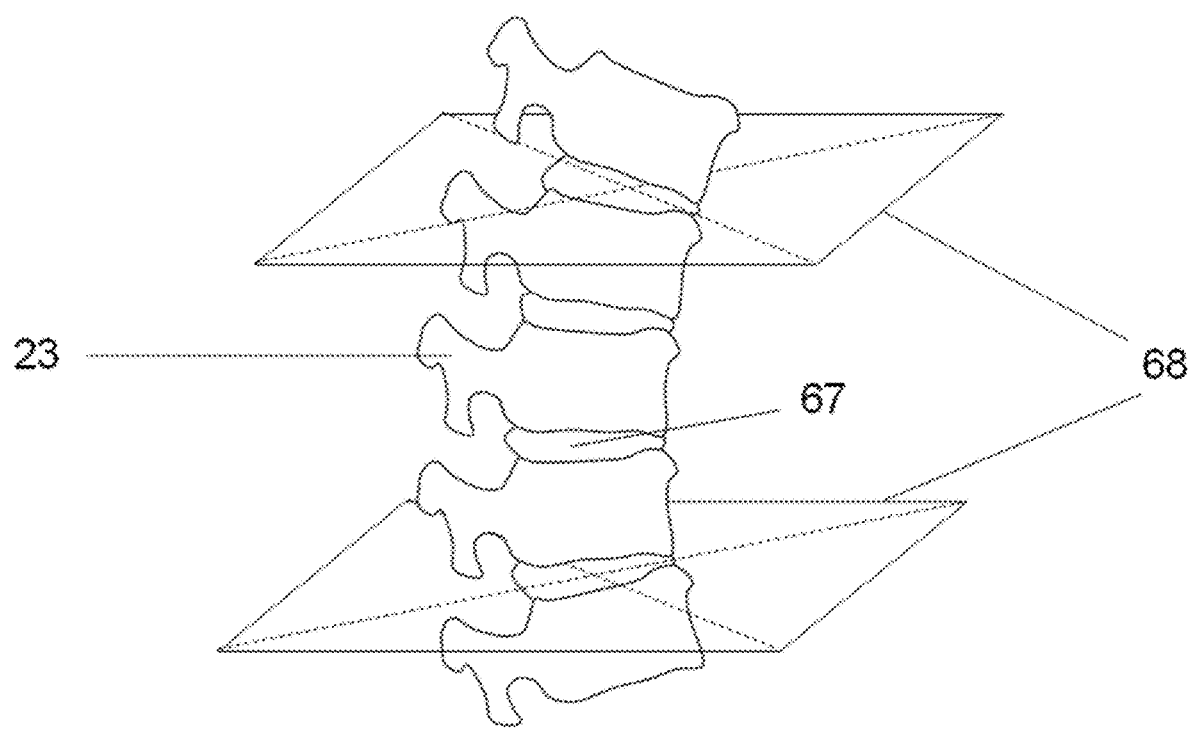
FIG. 11 illustrates an example implementation of a method of using fences to segment individual vertebrae from the spine.

In another example method, a user may perform segmentation of relevant vertebrae manually. FIG. 11 illustrates a sample manual segmentation of a portion of the spine. Manual segmentation is achieved by the user drawing fences 68 manually to separate each vertebra 23 at the adjacent vertebral disc(s) 67. This manual separation can occur at the immediate vertebral disc 67 or multiple vertebral discs away, dependent on the requirements of surgery. A fence limited seed region growing module can be used to extract the vertebrae 23 from the fence bounded region.

A fence-limited labeling module can be employed to label each vertebral volume using a fence-limited seed region growing (SRG) method. The volume is repeatedly expanded from a seed point until a growing point reaches a 3D fence and its gray value is within homogeneous volume thresholds, as described by Kim and Kim (Kim and Kim (2009) Computerized Medical Imaging and Graphics 33(5):343-352). Use of this module is based on whether the starting planes were inputted manually or are automatically generated.

The preoperative surgical plan and segmented preoperative imaging dataset can then be combined. FIG. 11 illustrates a sample output updated surgical plan using the system 100. The illustrated segmented and labeled preoperative image dataset 70 includes five vertebrae 23 that have been segmented from the preoperative CT dataset and labeled A-E, and also corresponding inter-vertebral discs 75. Following segmentation, an isosurface image of the segmented spine 71 can be generated.

To extract an isosurface dataset for each vertebra 23 from the corresponding segmented vertebrae dataset, a user can specify a contrast level for the vertebrae by entering the information into the system. The contrast level would typically lie between 1100-1200 Hounsfield units. A marching cubes algorithm (as described in U.S. Pat. No. 4,710,876) can, for example, be used to extract the isosurface image data output 71. A marching cubes algorithm generates a polygonal mesh of vertices and normals that define an outer surface of each vertebra 23.

A sample preoperative surgical plan 72 indicates two different principle axes 26 selected according to the system 100. The cone of acceptance 25 can also be included in the preoperative surgical plan output 72. The coordinates of the vertebrae data and principle axes 26 are known, since they are generated from the same preoperative CT dataset. These data are merged to generate a combined surgical plan output 73. The combined surgical plan 73 has known 3D coordinates which establish the spatial relationships between the preoperative CT dataset, the segmented isosurfaces of the individual or multiple (select) vertebra 23, and the principle axes 26 of the pedicle screw insertion site(s).

Referring to FIG. 9, a polygonal mesh representing the surface of a surgical field is acquired by the digital projector 15 to output surface topology data of the structure of interest, which is acquired in block 57.

Figure 13A:
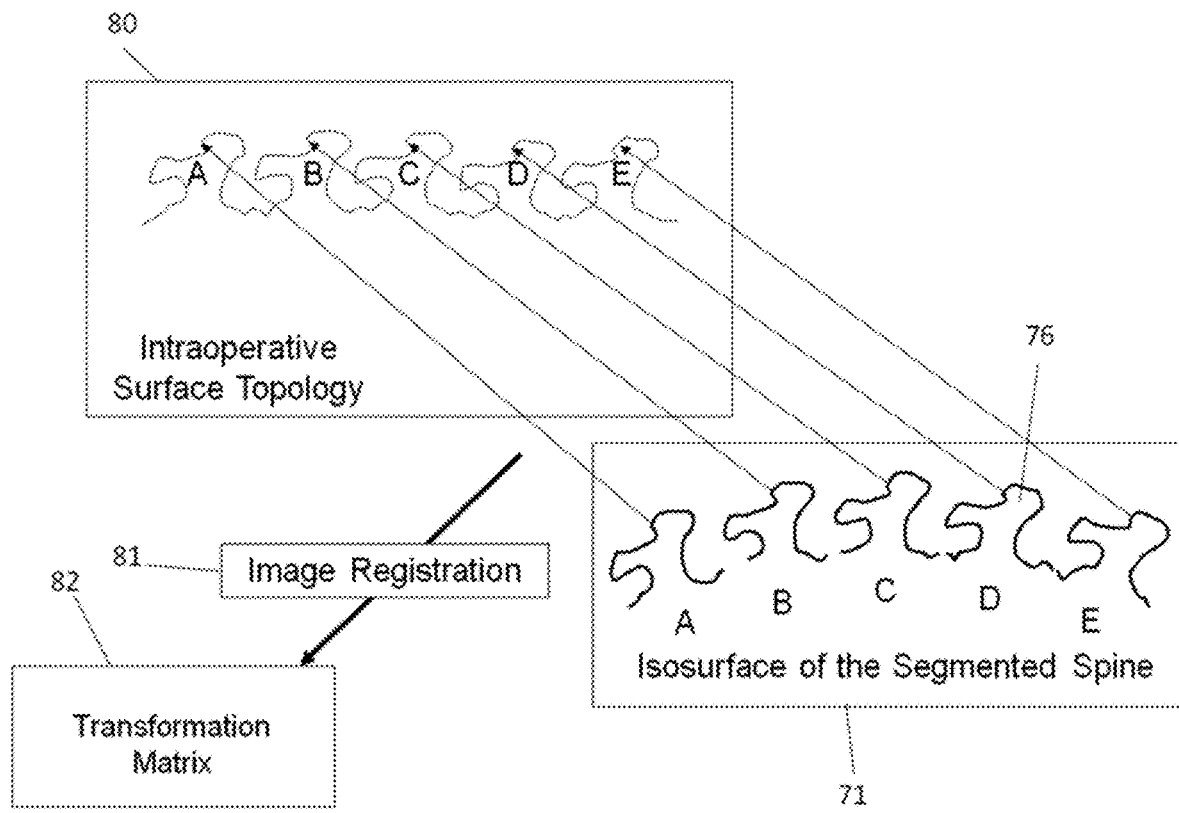
FIG. 13(a) illustrates an example implementation of correlating an isosurface topology image dataset of a segmented spine to an acquired intraoperative surface topology for registering the image datasets, in which a transformation matrix is derived.

As shown in FIG. 9, registration is then performed in block 58, wherein each of the vertebrae from the preoperative image dataset is registered to the backscattered radiation topology data acquired in block 57. A schematic of a sample registration process is illustrated in FIG. 13(*a*). Surface topology data 80 corresponding to vertebrae 23 of interest are acquired. The segmented isosurface data 71 are used as input data for registration. Data for each vertebra 23 of interest from the preoperative image dataset 76 are registered in block 81 to corresponding data from the intraoperative topology image dataset 57 individually.

As illustrated in FIG. 10, a particular example method that can be implemented for the registration process 58 is based on iterative closest point (ICP), one of the most commonly used surface registration techniques. ICP is useful for relatively small transformations when using complex point clouds. To speed up and reduce the chance of finding a local minimum during the registration process, a rough initial transformation (T_initial) can, for example, be used. Similarly, an interactive point-based approach can, for example, be used to derive the initial transformation.

For example, M (where M<5) representative points can be selected from each of the segmented isosurface image data (CT_MESH_OB_1 . . . CT_MESH_OB_N) (where N is the number of elements segmented from the structure and in this example, the number of vertebrae) to serve as virtual fiducial markers in both the CT isosurface and backscattered radiation surface topology datasets. Using a singular value decomposition algorithm, the M points can be brought into alignment providing an initial transformation for a more precise registration using the high resolution dataset.

Next, each of the segmented vertebrae 23 meshes noted above (CT_MESH_OB_1 . . . CT_MESH_OB_N) is registered to the backscattered radiation datasets using ICP in parallel with T_initial as an initial condition for the transformation. The derived transformation matrices 59 can be applied to the combined segmented isosurface data and corresponding registered preoperative surgical plan to update the surgical plan and orient the surgeon to match the structure of interest and the preoperative plan.

Figure 13B:
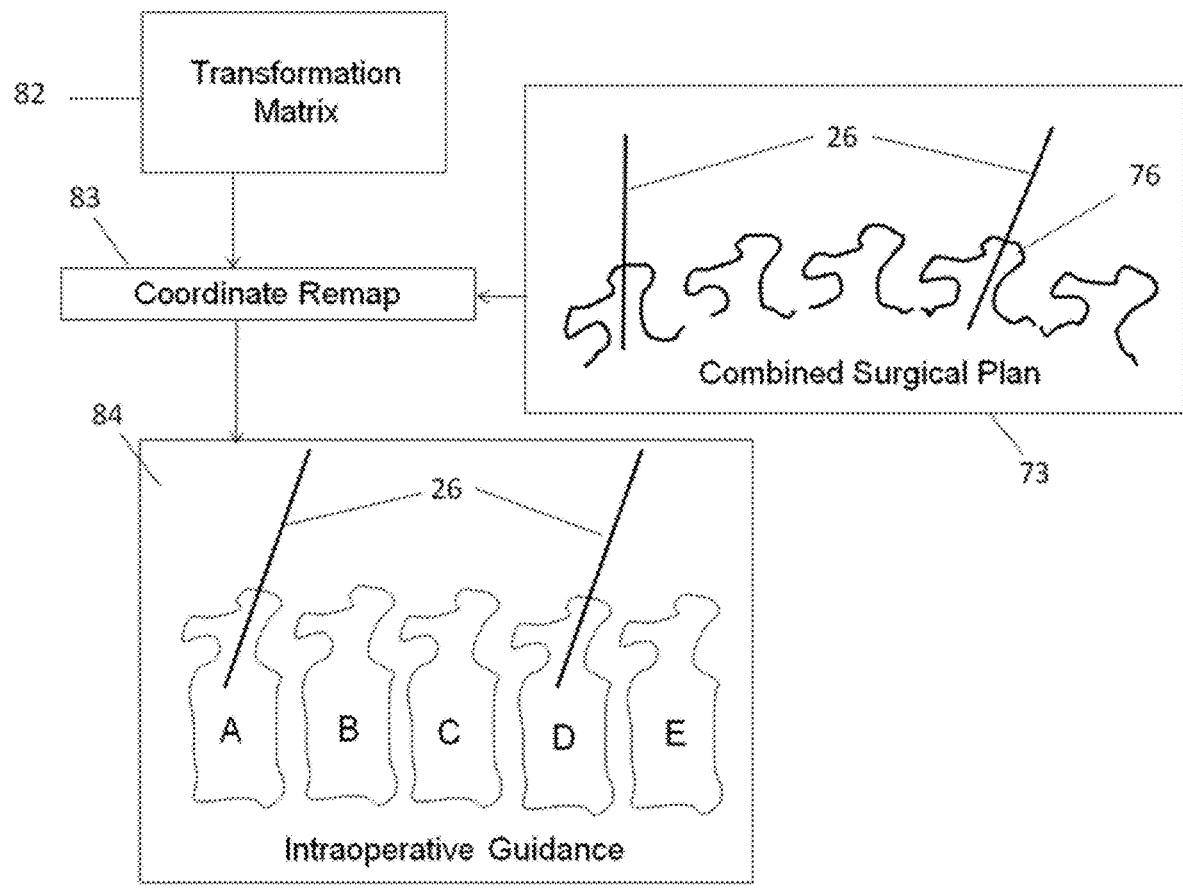
FIG. 13(b) illustrates an example implementation of combining a surgical plan (block 73) and transforming an image dataset (block 82) for remapping coordinates and updating the surgical plan for implantation of a surgical interventional device.

FIG. 13(b) illustrates updating the orientation of the surgical structure of interest and preoperative plan and the corresponding output by the system 84. The transformation matrix in block 82 provides data to enable coordinate remapping in block 83 for updating a combined surgical plan in block 73, corresponding to the immediate intraoperative location and orientation of a surgical structure of interest. An example output 84 is illustrated in FIG. 13(b). The output provides updated principle axis 26 identifying the ideal location of a surgical interventional device. Furthermore, since the preoperative topology image data are derived from the segmented image data of the preoperative CT scan, the entire target vertebrae from the preoperative CT may be displayed by the system 100.

Figure 16:
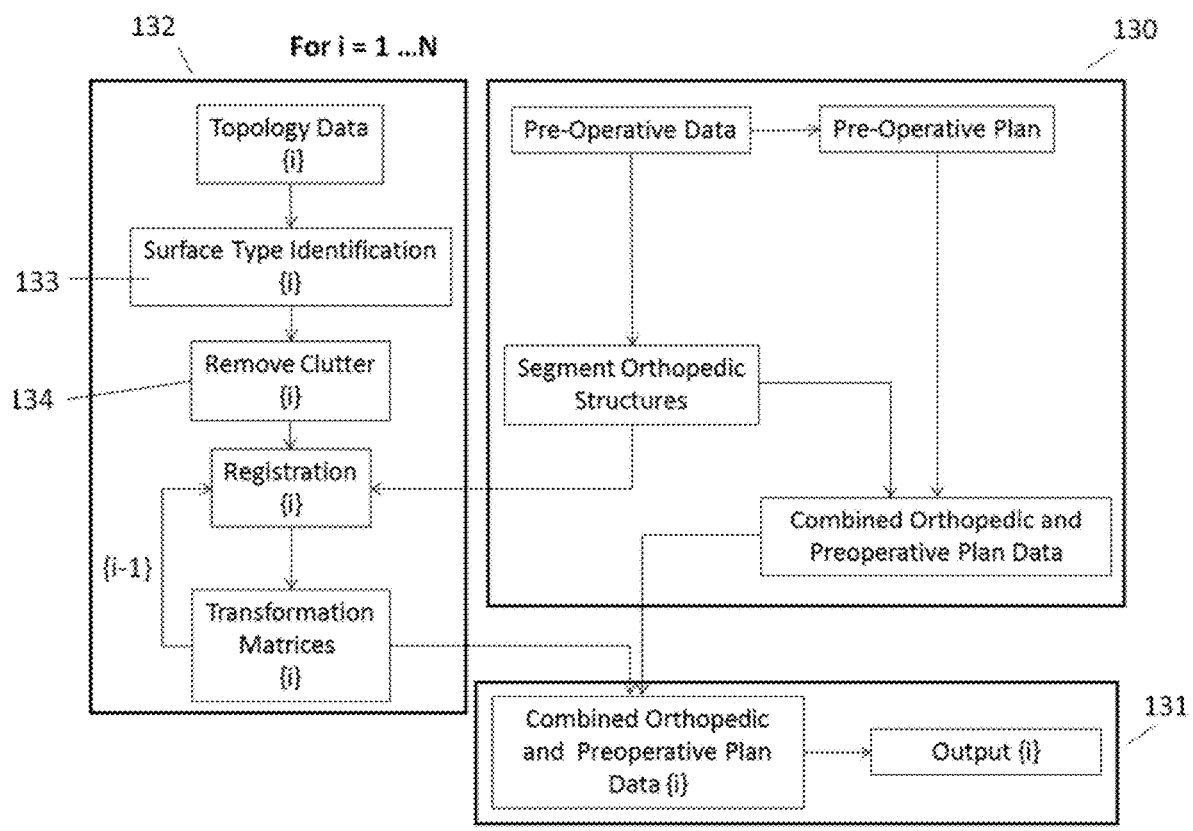
FIG. 16 is a flow diagram of an example implementation of a method of intraoperative surgical guidance feedback including surface type identification and clutter rejection.

To account for surgical field of view disruption during surgery, the system 100 can, for example, perform surface type identification to identify clutter (as described below with reference to FIG. 16). In cases where there is insufficient data for registration, guidance feedback pauses and resumes when there is a clearer field of view. Surface textures, or significant changes in elevation of the backscattered radiation image data, acquired by backscattered radiation imaging can be used to identify the blockage of field of view as clutter. Similarly, the placement of the surgical tool and/or the surgical interventional device within the surgical field of view can be located and identified as non-clutter items and compensated for. If items of clutter exist in the surgical field of view, the system 100 can, for example, inform the user, for example through display 4, to remove the clutter from the line of sight. With the surface type identified and clutter removed, each of the segmented orthopaedic structures can be registered to the backscattered radiation topology scan.

Use of Confidence Criteria During Registration

Intraoperatively registering the three-dimensional surface topology image data to additional image data of the structured segment may further include determining if registration is occurring within a pre-set confidence criteria. If the criteria are not met, then seeking intervention to provide additional data to be used in intraoperatively registering. Intraoperatively registering the three-dimensional surface topology image data to additional image data of the structured segment further can include registering unique features in a subset of points from the image data.

Accordingly, as a part of topology imaging and transformation, the system 100 can incorporate a confidence criteria component into the registration or transformation process. FIG. 14 illustrates a method of surgical guidance with error checking and corrective intervention. An error checking module 113 and a corrective intervention module 114 can be used to either reduce the system error, via additional input 115, or update the orthopedic structure and preoperative plan 60. Steps 110, 111, and 112 are otherwise similar to the corresponding steps 50, 51, and 52 of FIG. 8. If the system 100 cannot resolve ambiguities to within the defined confidence criteria during the registration or transformation, then the system 100 will require additional actions to resolve the ambiguity and can seek intervention 115. A prompt may be provided to a user, for example audibly, such as a beep, or visually, by text or flashing icon on a display 4.

The confidence criteria can, for example, be a fixed registration error threshold or variable registration error threshold that can be set, for example, by the surgeon preoperatively or inter-operatively. If the confidence criteria is not met, the surgeon may be asked to clear the field of view (for example, move away objects situated between the cameras and the surgical field), remove debris (for example, blood and tissue resting on top of the surface of interest), adjustment of the angle of the camera 12 or other methods to increase exposure of the bony surface of the vertebrae. As an alternative, the surgeon may be asked to identify certain features on the acquired surface topology image data, such as the spinous and transverse processes of a vertebrae, which can act as landmarks to correct and/or improve the registration results.

For example, a registration error can be calculated as the root mean square (RMS) of all matched point pairs used for alignment. As an example, let $P=\{p_1, p_2, \ldots, p_m\}$ and $Q=\{q_1, q_2, \ldots, q_n\}$ be the two surfaces to be registered, with m and n points respectively. In the context of a spinal surgery procedure, P may be the surface of the vertebrae acquired from CT, and Q may be the most recent intraoperative optical topology of the target of interest, or a previously acquired optical topology. A matched point pair is then found by locating the closest point in P to a point in Q, along with pre-defined criteria such as: (1) the normal vectors of the points must differ by less than 45 degrees, (2) neither of the points is along the edge of the surface, and (3) is within a maximum allowed distance. Therefore, the closest pair point matching results in the point sets $P' \in P$ and $Q' \in Q$ of length $r \leq (m|n)$:

$$P'=\{p'_1, p'_2, \ldots, p'_r\} \text{ and } Q'=\{q'_1, q'_2, \ldots, q'_r\}$$

Where $p'_i$ and $q'_i$ are the matched point pairs in the respective surfaces. The squared distance sd between two matched points $p'_i$ and $q'_i$ can then be defined as:

$$sd_{p'_i,q'_i}=(p'_{i,x}-q'_{i,x})^2+(p'_{i,y}-q'_{i,y})^2+(p'_{i,z}-q'_{i,z})^2$$

Then the RMS error of registration $E_{RMS}$ for the r point pairs is defined as:

$$E_{RMS} = \sqrt{\frac{sd_{p,q_1} + sd_{p,q_2} + \ldots + sd_{p,q_r}}{r}}$$

P' and Q' are used by the registration algorithm (for example, the aforementioned ICP algorithm) to determine a coordinate transform that rigidly moves P towards Q. Then, with the updated coordinates, a new set of matched point pairs can be calculated for the next registration iteration.

The error correction method can continue iteratively until sufficient convergence has been achieved. For example, in each iteration, the registration error is calculated. The $i^{th}$ RMS error is labeled as $E_{RMS_i}$. The registration algorithm then iterates until the change in RMS registration $\Delta E_{RMS}$ is less than a threshold $E_{thres}$, such as 0.1 mm.

$$\Delta E_{RMS}=|E_{RMS_i}-E_{RMS_{i-1}}|<E_{thres}$$

The final registration error may then be displayed to the surgeon, where his/her approval may be requested to proceed with navigation.

Figure 18:
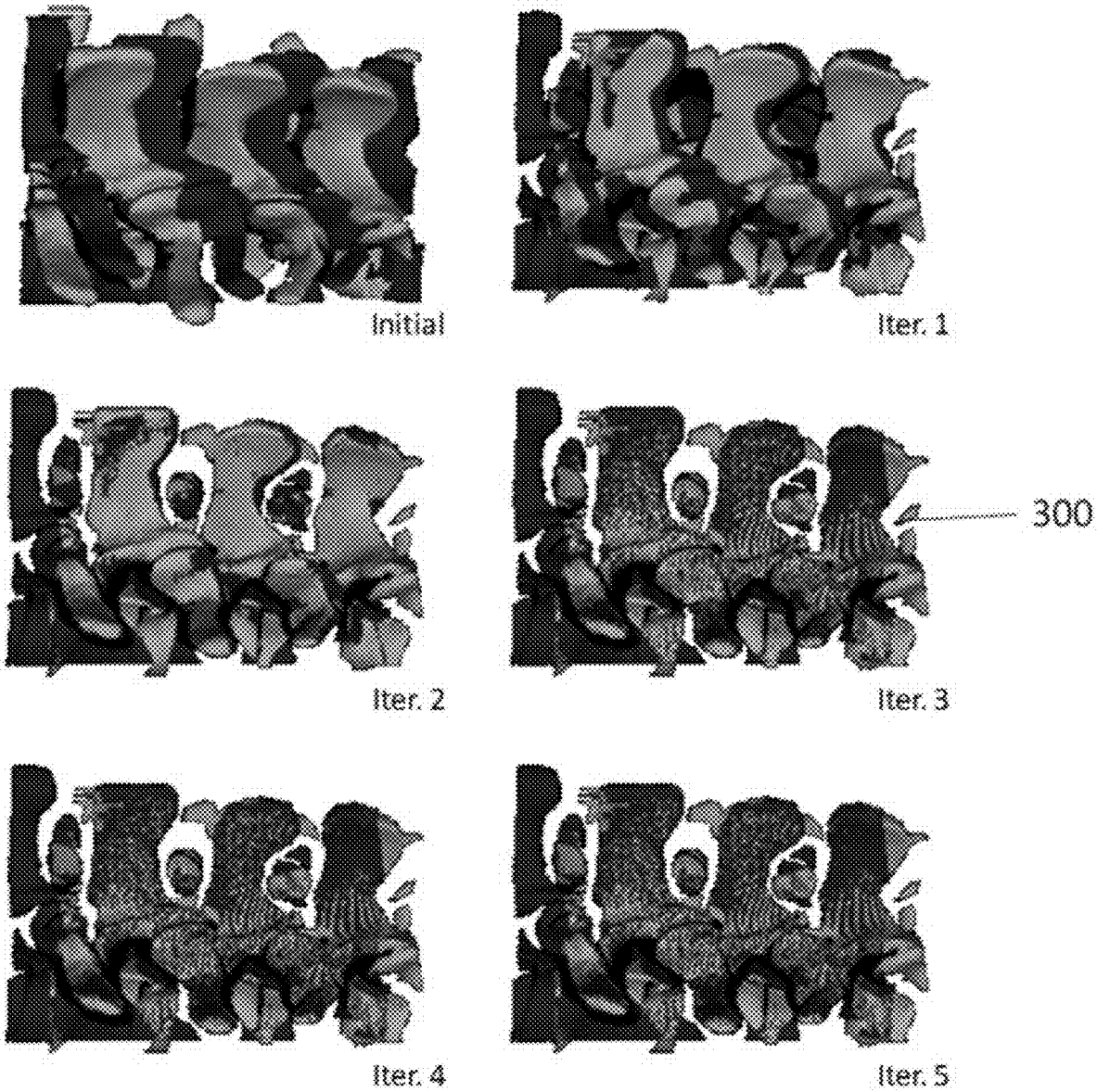
FIG. 18 displays grayscale plots showing typical example results of the iterative registration error process with the convergence of one registered optical topology dataset to a subsequent optical topology dataset.

FIGS. 18 (a)-(c) illustrate typical results 300 of this example method, demonstrating the iterative registration error process with the convergence of one registered optical topology dataset to a subsequent optical topology dataset, with the user selecting a confidence criteria of $E_{thres}$=0.1 mm. The resultant $E_{RMS}$ and $\Delta E_{RMS}$ values are depicted in Table 1 below:

TABLE 1

Example results of registration error calculation, topology to topology, representing quantitative results from the example registration error calculation shown in FIG. 18.

| Iterations | 1 | 2 | 3 | 4 | 5 |
|---|---|---|---|---|---|
| $E_{RMS_i}$ (mm) | 5.67721 | 2.46665 | 0.344543 | 0.11417 | 0.113973 |
| $\Delta E_{RMS}$ (mm) | — | 3.21056 | 2.122107 | 0.230373 | 0.000197 |

Figure 19:
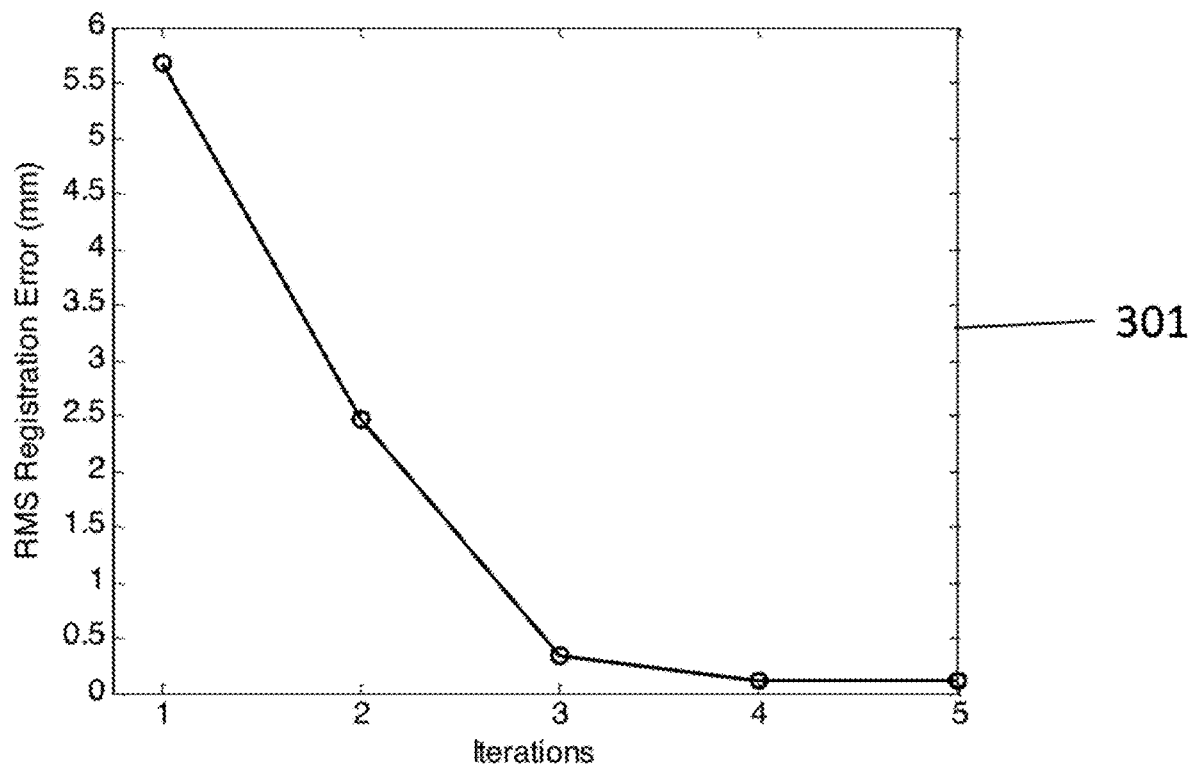
FIG. 19 demonstrates an iterative registration error as it convergences to the pre-defined confidence criteria of one optical topology dataset to a CT surface registration dataset.

Furthermore, FIG. 19 demonstrates that this iterative registration error converges to the pre-defined confidence criteria of one optical topology dataset to CT surface registration, with the user selecting a confidence criteria of $E_{thres}$=0.1 mm. The resultant $E_{RMS}$ and $\Delta E_{RMS}$ values are depicted in Table 2.

TABLE 2

Example results of registration error calculation, topology to CT, representing quantitative results from the example registration error calculation shown in FIG. 19.

| Iterations | 1 | 2 | 3 | 4 | 5 | 6 |
|---|---|---|---|---|---|---|
| $E_{RMS_i}$ (mm) | 3.70133 | 3.53156 | 3.06149 | 1.47036 | 0.823002 | 0.776784 |
| $\Delta E_{RMS}$ (mm) | — | 0.16977 | 2.16997 | 1.59113 | 0.647358 | 0.046218 |

Referring now to FIG. 15, an example method is shown in which only backscattered radiation image data previously registered to the preoperative image data is registered. The previously registered topology data is segmented in step 123, where clutter items may be removed, as they do not contribute to the registration of desirable bony surfaces. This produces a segmented optical data subset in step 124. In this method, for example, when counter 126 i==1, the registration 58 proceeds as in FIG. 8. After the initial registration 125 (with the counter 126 i>1), each of the preoperative image data structure segments (CT_MESH_OB_1 . . . CT_MESH_OB_N) is registered to the backscattered radiation topology dataset, and only the registered surfaces are retained in the backscattered radiation topology dataset. Again, steps 120, 121, and 122 are otherwise similar to steps 50, 51, and 52 of FIG. 8.

This process generates a segmented backscattered radiation topology dataset comprising the exposed structures of interest (OT_MESH_OB_1 . . . OT_MESH_OB_N) and excludes non-relevant targets, such as surgical drapes. This dataset is then used in the next registration iteration as a proxy for the segmented orthopaedic structures dataset. As the registration is limited to only the relevant exposed surfaces, the backscattered radiation image dataset can be reduced in size so that registration can be faster.

In one example method, the initial registration can be performed when the structure is sufficiently exposed to the camera 12 and all obstructions are removed between the exposed structure and the camera 12. The initial registration can be repeated if there is a change to the region of interest intraoperatively, for instance, the field of view is changed to a different vertebra, or there are changes in the anatomy due to surgical intervention, Texture-Based Surface Identification for Clutter Rejection In one embodiment, the system performs surface type identification to identify and remove clutter. This step can be useful in detecting, accounting for, and optionally correcting field of view disruption. Such field of view disruptions can occur during operation due to movements by the surgeon or other personnel. In cases where there is insufficient data for registration, guidance feedback pauses and resumes when there is a clearer field of view. Referring to FIG. 16, an example embodiment of surgical guidance with surface identification 133 and a clutter removal processing step 134 in block 102 is illustrated. Blocks 130, 131, and 132 of FIG. 16 are otherwise similar to blocks 50, 51, and 52 of FIG. 8.

In one example, surface textures, or significant changes in the center of mass of the backscattered radiation image data, acquired by backscattered radiation imaging, can be used to identify the blockage of field of view as clutter. Similarly, the placement of surgical tools and implants within the field of view can be located and identified as non-clutter items and compensated for. If items of clutter exist in the field of view, implementations of the system 100 can, for example, inform the user to remove the clutter from the line of sight.

In addition, color textures acquired by the camera 12 can be employed to differentiate structures within the backscattered radiation image data of the operative region of interest to provide additional information for improving the speed and accuracy of the registration/transformation. For example, and as further described below, non-clutter, non-structure surface can be ignored during registration and transformation of backscattered radiation image structure surface.

Spectral rejection of clutter can be employed by recognizing that different materials in the field of view scatter more or less of some portions of the electromagnetic spectrum. A potential way to improve surface identification is through the use of the filter(s) 40 integrated with the camera 12 to preferentially accept only certain bands of the electromagnetic spectrum. Such filters can be optimized to achieve maximum contrast between different materials and thus improve the clutter identification process. For example, those bands that are common to backscattered radiation from typical clutter items, the structure, and surgical tools can be filtered out such that high-contrast backscattered radiation is acquired.

In orthopaedic applications where it is usually the case that the bony surfaces from the topology image sets are to be registered to the preoperative CT or MRI data, it may be effective to first remove non-bony-surfaces such as soft tissue, surgical drapes, and other irrelevant surface that are commonly observed during a surgical procedure. A number of methods could be used independently, or in conjunction with each other, to achieve this goal. The following paragraphs describe specific implementations and examples of potential clutter rejection algorithms based on spectral-based rejection, color-based rejection and surface roughness-based rejection.

Spectral-Based Clutter Rejection

Structured light illumination is typically performed with white light. However, if one or more specific spectral bands are employed to perform the structured light illumination, certain spectral regions can be rejected. This in turn can be employed to eliminate certain surfaces from the acquired image data due to the specific absorption and scattering properties of various materials. For example, high absorption and or low scattering within the implemented spectral band will limit the visibility of the low scattering region to the camera(s).

Figure 22:
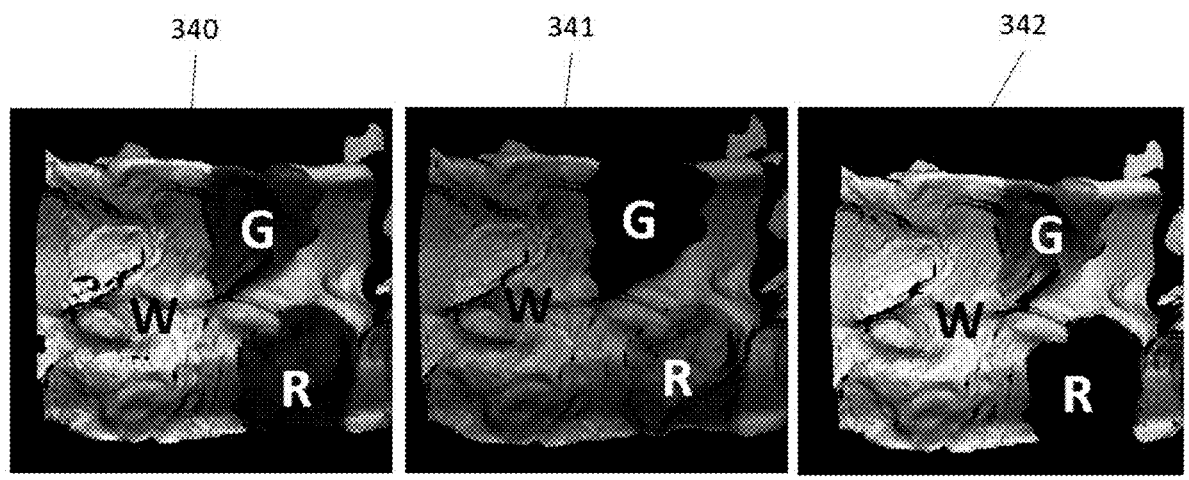
FIG. 22 is an example demonstration of spectral based clutter rejection.

FIG. 22 demonstrates an example implementation of this method, where image 340 is obtained according to structured light reconstruction using white light illumination, 341 is obtained according to structured light reconstruction using red light illumination, and 342 is obtained according to structured light reconstruction using green light illumination. The majority of the surface is white (W) in color with two small regions of red (R) and green (G). Under white light illumination all three regions are captured and reconstructed. Under red illumination only, the white and red surfaces are captured and reconstructed. Moreover, under green illumination, only the white and green surfaces are captured and reconstructed.

Accordingly, an example implementation of the present spectral based clutter rejection technique could include the automatic identification or removal of specifically colored tools, gloves, drapes, etc., within the surgical field of view. Alternatively, white light illumination could be used, where band pass filters 40 within the field of view of the cameras could be used to image specific spectral bands of interest. It will be apparent to those skilled in the art that there are a wide variety of methods for achieving spectrally selective detection, including employing spectrally narrow emitters, spectrally filtering a broadband emitter, and/or spectrally filtering a broadband imaging detector (e.g. camera).

Figure 23:
FIG. 23 is an example of color based clutter rejection, showing structured light images with and without the use of color for the rejection of muscular tissue.

FIG. 23 demonstrates an example implementation of how colorized mesh data 350, acquired with a structured light scanner, can be employed to reject muscular tissue, while maintaining bony surfaces 351. Monochrome cameras may be employed to reconstruct a 3D surface using structured light imaging. However, the use of color cameras allows for the direct assignment of color values to each point of the reconstructed surface. These color values are stored as tuples of RGB values (i.e. (R,G,B), where R,G,B are elements of {0-255}) stored at each mesh point, 350. The algorithm then traverses the mesh and generates a set of seed points, for example, with a spacing of $\Delta r=1.0$ mm. Next, at each point in the mesh the R/B and R/G ratio values are calculated. Taking the ratio of R, G and B values, instead of directly using raw values, provides a method to help mitigate effects induced by variable illumination.

Alternatively, more complex methods can be applied to better deal with illumination variability, for example, as taught in Lin et al. (C. Lin et al, "Color image segmentation using relative values of RGB in various illumination conditions" International journal of computers Issue 2 Vol 5, 2011). Average R/B and R/G values in a disk, with radius $r=2.0$ mm, surrounding each seed point are then calculated. Finally, these disks are rejected or accepted based on their average ratio values (similarly, green and blue surfaces could be rejected by setting threshold values for G/R, G/B and B/R, B/G respectively). For the specific example in FIG. 23, regions that fulfilled the criteria of $0.9<R/G<1.4$ and $0.9<R/B<1.4$ produced an image 351, where bony surfaces were identified, while muscle was removed from the resultant dataset.

Surface Roughness-Based Clutter Rejection

In another embodiment, clutter rejection is performed using detected variations in surface roughness, where the variations are detected using a surface topology backscattered radiation image acquisition system 1. In an example implementation, mesh data acquired with a structured light scanner can be employed to reject muscle tissue, while keeping bony surfaces in the topology dataset. The basis for this algorithm is the knowledge that most bony surfaces are relatively smooth, while muscle has a striated structure. In addition, the muscles are subject to cutting during spinal surgery by the surgeon, further contributing to their surface unevenness. Combined, this gives rise to large curvatures in the mesh that may be detected. This can be characterized by calculating the maximum principal curvature at each point in the mesh, for example, as shown in Guggenheimer et al. (Guggenheimer, Heinrich "Chapter 10. Surfaces". *Differential Geometry*. (1977) Dover), which in turn can be used to reject the muscle tissue when compared to a bony surface. The clutter rejection process begins by acquiring an optical topology scan, after which a surface roughness-based clutter algorithm, optionally executed by surgical guidance controller 3, calculates the maximum principal curvature at each point in the mesh. The algorithm then traverses the mesh and generates a set of seed points, for example, with a spacing of $\Delta r=1.0$ mm. The maximum principal curvatures are then averaged in a disk, for example, with radius $r=2.0$ mm, surrounding each seed point. Finally, the disks are accepted or rejected based on the average curvature values.

Figure 24:
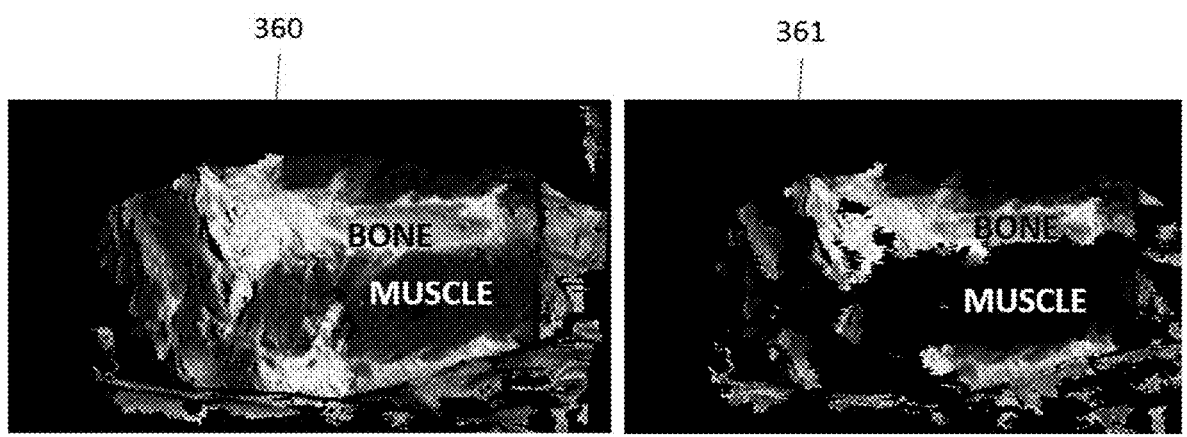
FIG. 24 is an example demonstration of surface roughness based clutter rejection, showing structured light reconstruction of bone and muscle tissue with and without roughness-based clutter rejection.

The resulting clutter-based rejection is illustrated in FIG. 24, where 360 shows structured light reconstruction of bone and muscle tissue under white illumination, and where 361 shows structured light reconstruction of bone and muscle tissue under white illumination with roughness based clutter rejection. For example only regions that fulfilled the criteria of a curvature less than 0.7 were kept to produce image 361 from image 360 in FIG. 24.

With the surface type identified and clutter removed, each of the segmented orthopaedic structures can be registered to the backscattered radiation topology scan, potentially with greater accuracy.

Continuous System Operation

In one embodiment, system 100 may act autonomously for intermittent periods of time, such as performing regular updates of the image registration and/or surgical plan without user input. In one example, the system may provide an external request for user action to enable the system perform semi-autonomously under circumstances where insufficient image data is available in the field of view. For example, the system may provide the user with continuously updated surgical guidance feedback in the form of an image of the current orientation of the surgical structure of interest outputted on the display, and updated surgical guidance plan for the accurate placement of the surgical interventional device. However, in the event that the surface to be imaged is obscured or blocked, for example, by a surgeon's arm, the system may alert the user and temporarily suspend image registration processing and displaying of results.

Continuous updating of surgical guidance feedback may occur autonomously, such that upon completion of one update, another update automatically commences. In such an embodiment, the user is not required to manually input a request for an update from the system 100. Accordingly, the use of system 100 may be advantageous in reducing surgical procedure time, due to real time updates of the surgical structure of interest, compared to other systems currently in use.

In one example, the rate of data updating may be contingent or dependent on a temporal margin for error at any given time point during a surgical procedure. The temporal margin for error may be dependent on the time required to achieve a potential negative outcome, for example, the situation where the surgeon is not operating at an ideal target implantation site. The time required for the system to achieve the potential negative outcome may be a factor of the accuracy of the system, the spatial margin for error at a given time in a given procedure, and the speed at which the procedure is being performed.

For example, if a clinician has 5 mm of spatial margin and the system is accurate to within 2 mm of the ideal interventional device implantation location, then the spatial error margin is 3 mm. If the clinician is moving at 1 mm per second or less, then the clinician has 3 seconds of temporal margin for error. Updates could occur continuously in this scenario once every 3 seconds to avoid an error. Any error in the calculation of an implantation trajectory at a given time may not lead definitively to a negative outcome, however, such an error can reduce the margin for error for future points along the principle axis. Accordingly, more frequent updates will lead to improved feedback and accuracy. Depending on the execution speed of the surgeon (typically slow for precise procedures), multiple updates per given unit time (i.e., one or a few seconds) may provide the appearance of continuous motion without stutter for image-based guidance feedback. For text-based surgical guidance feedback, updates may need to be slower to allow one update to be read before the next occurs.

In one embodiment, one or more fiducial markers may be attached to, or worn by, the surgeon in order to dynamically determine the rate of change of motion of the surgeon. The rate of change of motion may be measured by the cameras of the backscattered radiation surface topology imaging device, or may be detected using a global position sensing system (described further below). The rate of system updating may then be dynamically adjusted according to the measured rate of the surgeon's movement. In another example, the rate may be determined by dynamically measuring the rate of change of the position of a tool, probe or other surgical instrument to which fiducial markers are attached.

Tool Tracking

In selected embodiments, a tool, such as a surgical tool, probe, surgical instrument, or other freely movable item, having fiducial markers adhered thereto, may also be integrated with and tracked by system 100, in order to co-register the position of the tool with 3D pre-operative image data. Tool tracking can be performed via several techniques, such as passive infrared reflectance triangulation or active emitting triangulation. The surgical tool can be tracked to provide a surgeon with a feedback mechanism (i.e. visual or audio or both) to identify the planned trajectory (x, y, z, roll, yaw, pitch) of the surgical tool. Such guidance feedback can assist in accurate device placement. The system 100 can, for example, also track the position of the implantation device until it reaches a planned location or depth to further assist in accurate device placement.

Figure 25:
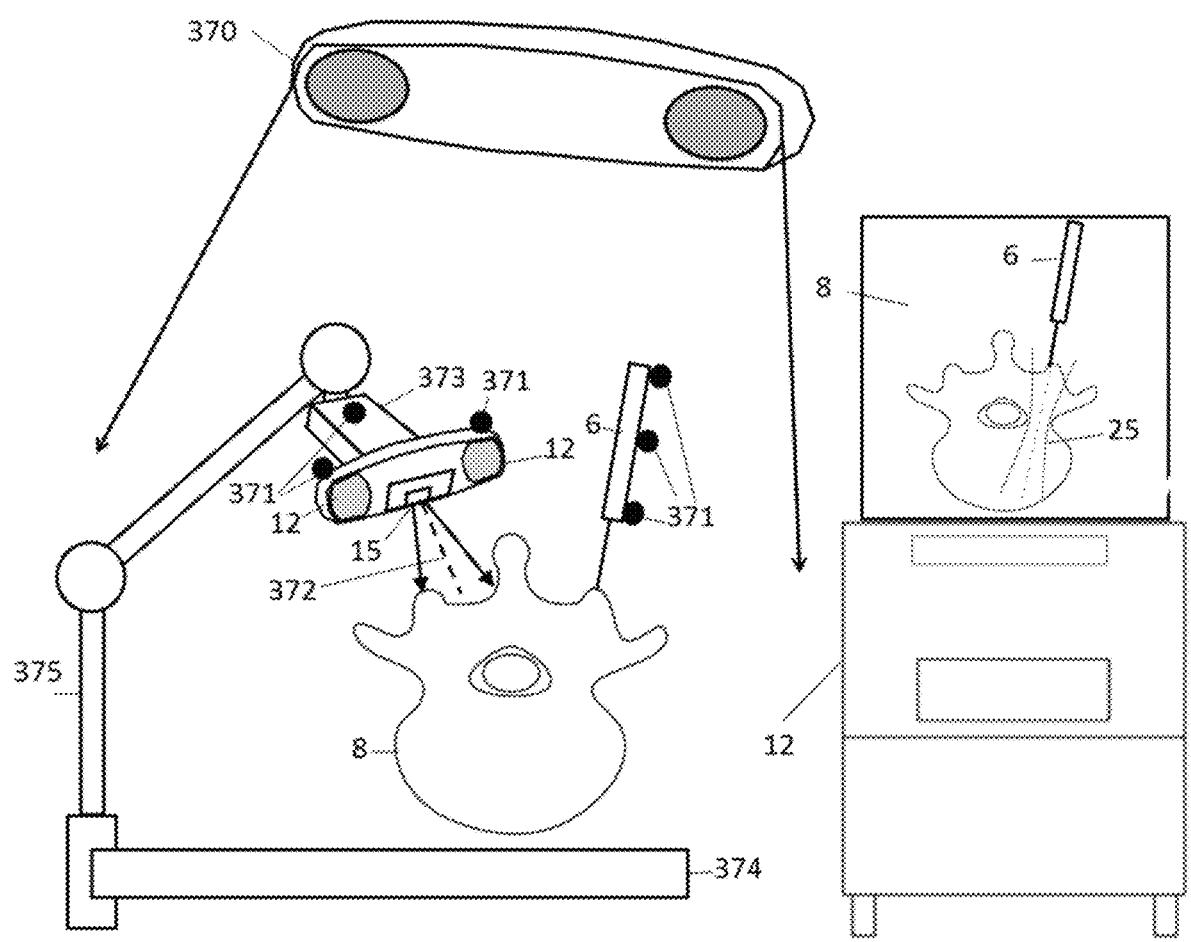
FIG. 25 is the integration of tool tracking and surface topology imaging system to enable surgical navigation.

FIG. 25 demonstrates an embodiment showing the integration of tool tracking with a surface topology imaging system, which includes projector 15 and camera 12 to yield a complete surgical navigation system. The spatial locations of the projector 15 and cameras 12, along with the surgical tool 6, can be computed via triangulation of fiducial markers 371 as detected by optical position measurement system 370. The identification of these fiducial markers can occur using various techniques, where common methods include passive IR ball tracking or active emitting technologies.

Figure 26:
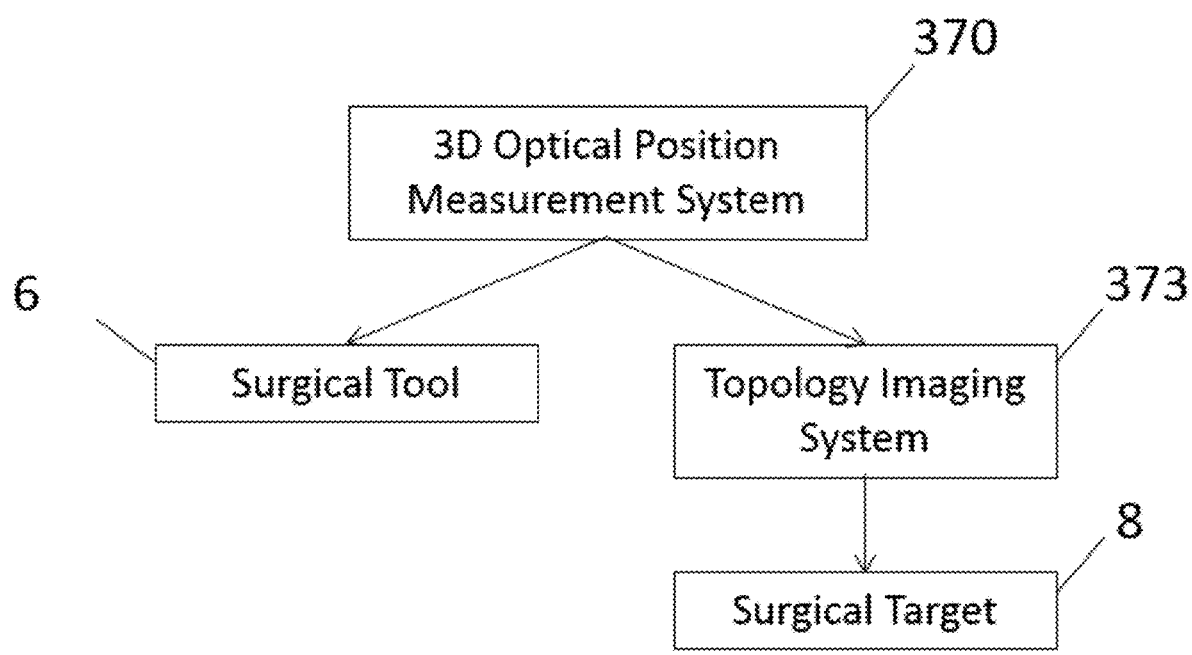
FIG. 26 is a schematic of how the coordinates of the different components of the surgical navigation system are related. The tip of the arrow indicates the components whose position is tracked.

FIG. 26 summarizes the relation between the coordinate systems relevant to FIG. 25. The location and orientation of surgical target 8 (for example, a vertebra of interest) relative to the surface topology imaging system 373 is known based on the optical topology measurements. The location and orientation of the surface topology imaging system 373 relative to an optical position measurement system 370 (such as one for the purpose of tool tracking) is known via the detection of the fiducial markers on imaging system 373 as detected by optical position measurement system 370. The combination of these two pieces of information, allow the topology data to be registered into the coordinate system of the position measurement system 370. Finally, the location of the surgical tool 6 relative to the optical position measurement system 370 is known, similarly via the detection of the fiducial markers on tool 6 as detected by optical position measurement system 370. Therefore, the location of the surgical tool 6 relative to the surgical target of interest 8 is now defined as both the surgical target and tool are tracked in the coordinate system of position measurement system 370.

With the positional information of the tool 6 relative to the vertebrae known, the cone of acceptance 25 and current surgical tool spatial location 6 are displayed 8 to the surgeon, via a portable workstation 7 to provide real-time feedback to aid in the placement of interventional devices (i.e. pedicle screw, rod, etc). As an example, the topology projector system 373 can be attached to the surgical table 374 and positioned into an appropriate imaging position via a reticulating arm 375. The topology projector system 373 can also be positioned on either side of the surgical table 374 to provide an optimal imaging field of view. Alternatively, the topology projector system could also be attached to a portable cart, be ceiling mounted or attached to the surgical room lighting system to achieve an optimal surgical field of view.

Figure 27:
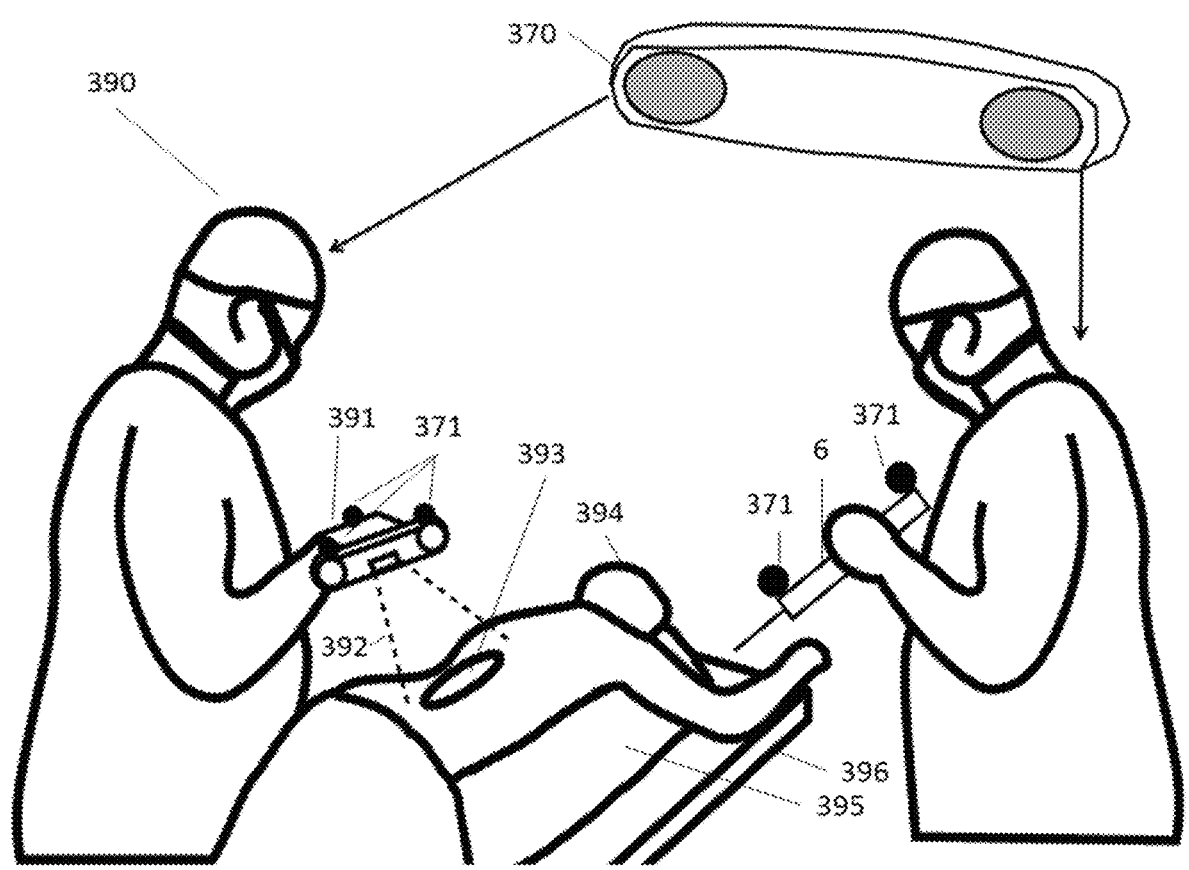
FIG. 27 is an example implementation used in the operating room, where the surface topology imaging is a handheld device.

Another example implementation of the surgical navigation used in the operating room by surgeons 390 is shown in FIG. 27. The topology imaging system is a handheld device 391 with field of view 392 overlooking an incision 393 made on the patient 394 to expose the spine. The patient rests on top of a positioning couch 395 on a surgical table 396. Unlike the example system illustrated in FIG. 25, where topology projector system 373 was mounted to surgical table 374 and reticulating arm 375, in the present example, topology projector system 373 may be freely moved intraoperatively. The ability to decouple topology projector system 373 from a rigid frame arises from the placement of the fiducial markers 371 on topology projector system 373, thereby enabling the spatial tracking of both topology projector system 373 and tool 6 in a common, global reference frame, by optical position measurement system 370. In order to compensate for the motion of both topology projector system 373 and tool 6, system updates may be performed periodically on a suitable timescale (as described above).

Accordingly, in the present example, as illustrated in FIG. 25, a surgical guidance system is provided, in which a fiducially marked surface topology backscattered radiation image acquisition system and a fiducially marked tool are freely movable relative to each other, and relative to the patient, by virtue of the their positional detection and reference frame registration using optical position measurement system 370. The present system thus provides a surgical guidance system whereby all fiducial marking have been effectively transferred from the patient to the system. Moreover, the present system does not require intraoperative recalibration. This embodiment avoids requiring a calibration step to register topology projector system 373 to tool 6, thereby saving time and positively impacting clinical workflow.

Figure 28A:
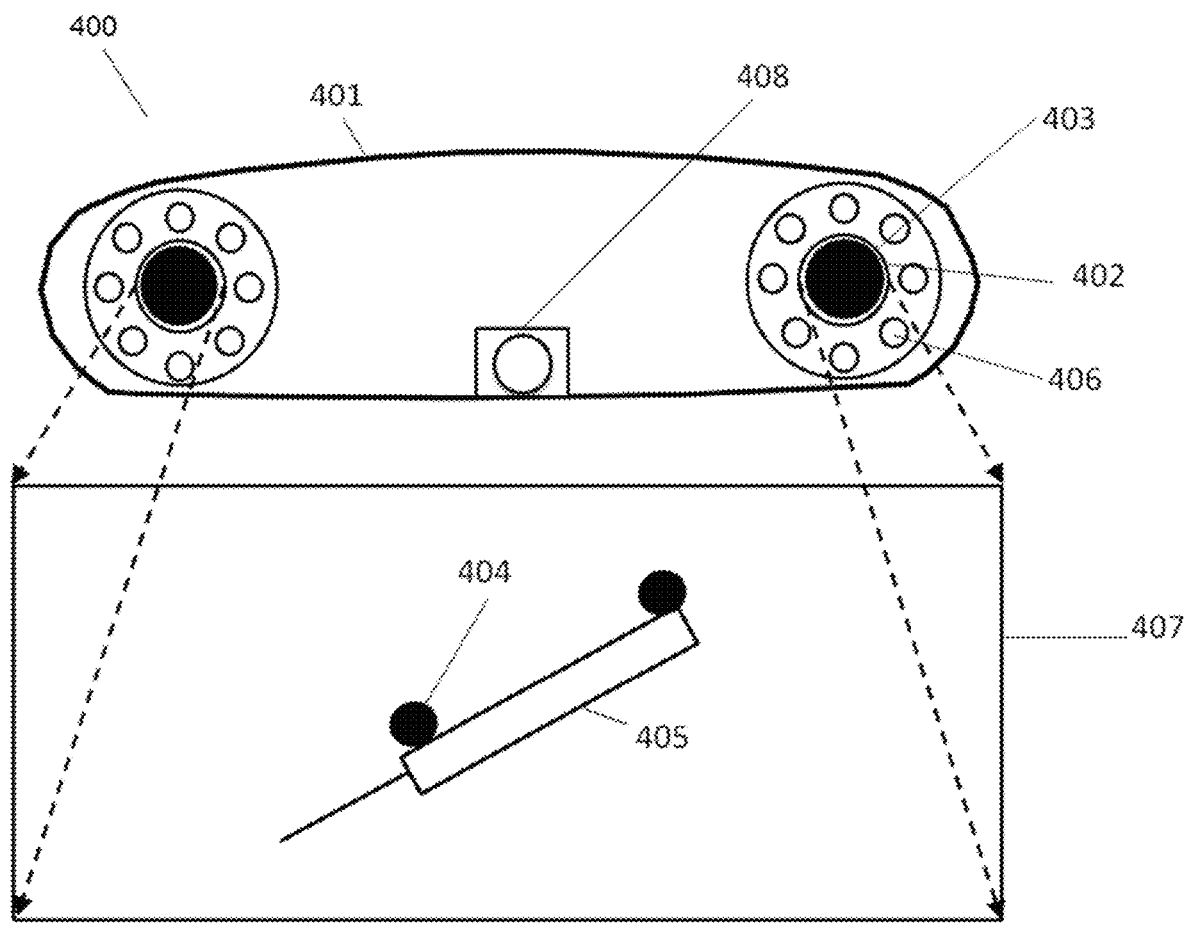
FIG. 28(a) is an illustration of an example system for surface topology detection and tool tracking using two cameras, where the cameras have a dual role of acquiring surface topology and tool tracking data. The cameras and projectors are rigidly attached to a frame so that a fixed spatial relationship exists between the components.

Another example system is provided in FIG. 28(a). Unlike the example provided in FIG. 27, the present example implementation utilizes topology projector system 373 for measuring both the surface of interest on the patient and for triangulation-based tool tracking. By employing topology projector system 373 for both functions, the system is operable without the need for optical position measurement system 370.

Referring to FIG. 28(a), the example system 400 includes a frame 401 supporting two cameras 402 equipped with optical filters 403. Cameras 402 detect fiducial markers 404 adhered to tool 405. Fiducial markers 404 may be passive reflective markers, or active emitters, provided that light emitted or reflected by fiducial markers 404 is detectable by camera 402 after passing through filters 403.

Fiducial markers 404 are illuminated by source 406, which may be any of a wide range of optical sources. If fiducial markers 404 are passively reflecting markers, then source 406 has a spectral profile that is chosen to be transmitted through filter 403. Alternatively, if markers 404 are fluorescent markers, then source 406 is selected to have a spectral profile suitable for generating fluorescence from markers 404, and filter 403 includes a spectral passband for transmitting the emitted fluorescence.

In one example, fiducial markers 404 are passive infrared (IR) balls. IR light for illuminating passive IR balls 404 attached to the tracked tool 405 is provided by source 406. Source 406 is shown in the example figure as light emitting diodes.

System 400 is characterized by field of view 407, which is determined at least in part by the angular emission bandwidth of light source 403 and the angular acceptance bandwidth of cameras 402. During operation, frame 401 is oriented such that field of view 407 envelops the surface of interest on the surgical target.

Topology information is obtained by topology projector system 373, which may be a structured light source including, for example, projector 408 for illuminating the target for topology imaging. Projector 408 may be a miniature projector. In order to utilize cameras 402 for both topology detection and tool tracking, the emission spectrum of topology projector system 373 is selected to support detection of backscattered radiation by cameras 402. This is achieved by selecting a spectrum of filter 403 and/or an emission wavelength of topology projector system 373 such that the backscattered radiation passes through filter 403. In one example, the bandwidth of filter 403 is chosen to transmit both the backscattered radiation and the optical signal provided (for example, reflected or emitted) by fiducial markers 404. In another example, filter 403 may be characterized by multiple optical passbands for transmitting both the backscattered radiation and the optical signal provided by fiducial markers 404. In another example, two filters may be provided and periodically translated or rotated into the optical path of camera 402, where each filter is provided for a separate imaging modality (topological detection and fiducial marker detection).

It will be understood that cameras 402 and projector 408 each have an associated focal region extending over their respective depths of field. In one embodiment, cameras 402 and projector 408 are configured such that their respective focal regions overlap at or near a given region of interest. The overlapping of the two focal regions (such that both systems overlap over at least a portion of their respective depths of field) enables accuracy in terms of both the resolving of the fine spatial features by cameras 402, and in terms of projecting the finest/clearest patterns by projector 408. This overlap can be obtained, for example, by appropriate selection of focusing or beam conditioning optics, by the relative positioning of the two subsystems, and/or the relative orientation of the two subsystems, such that the respective focal regions overlap at or near the desired region of interest.

In some embodiments, the focal regions may be overlapped such that the region of overlap is of sufficient distance away from system 400 so as to not obstruct or otherwise impair the surgeons during a medical procedure. For example, in some example implementations, this distance may be in the range of approximately 1.5 to 3 meters. Therefore, in one example implementation, system 400 may be positioned so that it is approximately 1.5 to 3 meters away from the operating region of interest, and such that the overlapping focal regions of cameras 402 and projector 408 are at the operating region of interest. It is to be understood that the field of view of illumination sources 406 should also overlap this region of interest, in order to provide suitable and sufficient illumination of fiducial markers 404.

For simultaneous real-time triangulation-based tool tracking and topology imaging, the system 400 may be controlled such that image acquisition is configured for supporting both imaging modalities. In one example, in which cameras 402 are employed for both imaging modalities, the detection of surface topology via backscattered radiation and the detection of the position and orientation of tool 405 may be performed serially. For example, the two modalities may be interleaved such the cameras 402 acquire a first set of images when only topology projector system 373 is active (i.e. emitting light), and subsequently a second set of images is acquired when only the tool tracking light source 406 is turned on, where the process is thereafter repeated (for example, on a continuous basis).

Figure 29:
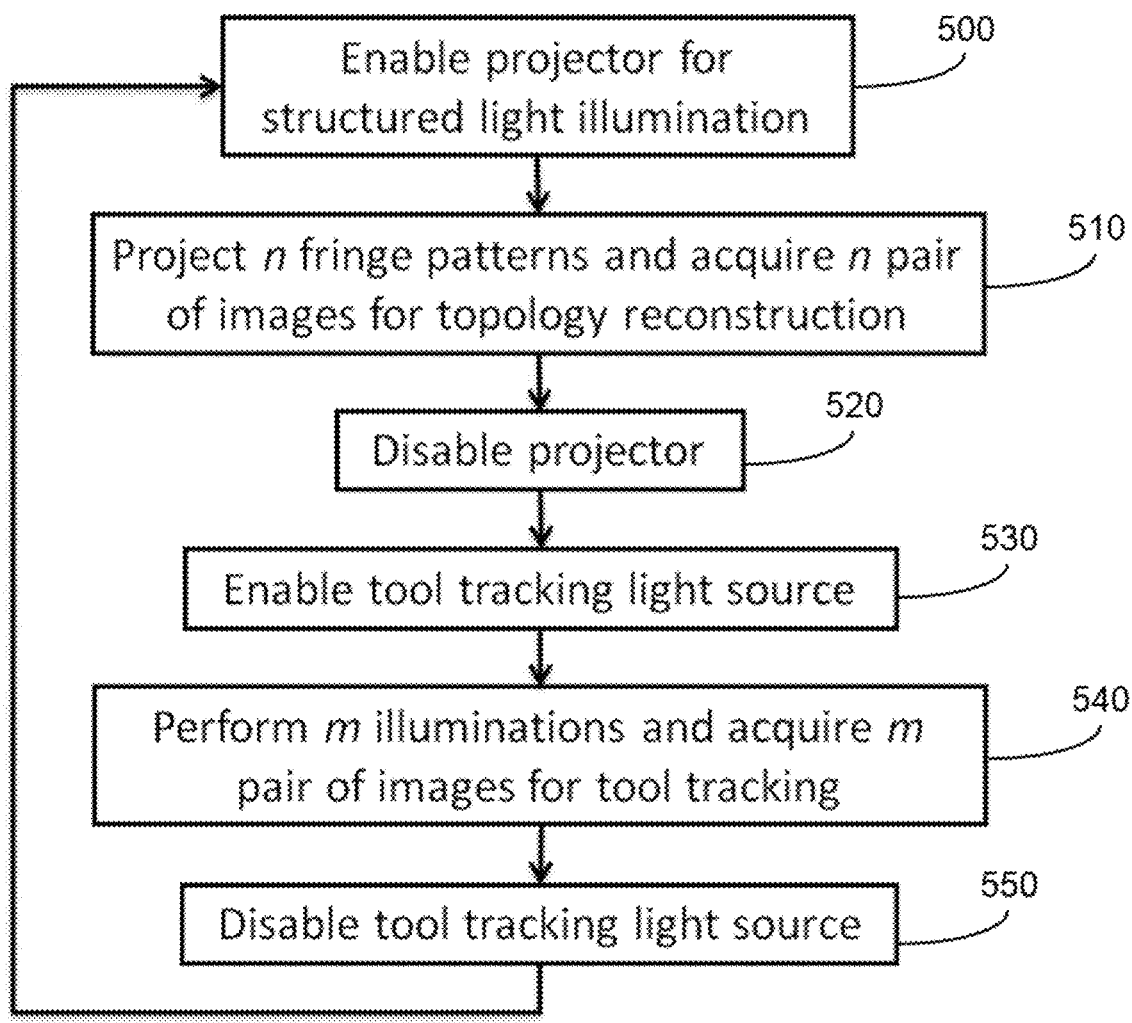
FIG. 29 is a flow chart illustrating an example method of performing serial measurements of surface topology and tool tracking with an integrated system.

This serial acquisition method is illustrated in the flowchart provided in FIG. 29 for the example case of a structured light system. In step 500, the structured light projector is activated. The surface of interest is illuminated with optical fringe patterns in step 510, and the topology image is detected and processed. Subsequently, in step 520, the projector is deactivated and the optical fringe pattern is no longer projected onto the surface of interest. In step 530, the tool tracking light source is activated, and the signals from the fiducial markers are detected and processed in step 540. Finally, in step 550, the tool tracking light source is deactivated, and the process may be repeated. The number of acquisitions n and m can be varied, depending on the temporal and signal-to-noise requirements of tool tracking vs. topology imaging.

In order to display the tool position and orientation with pre-operative image data co-registered to the surface topology images, the reference frame of the tool tracking system is registered to the reference frame of topology projector system 373. Since the system frame 401 houses both the topology imaging and triangulation-based tool tracking hardware, the location of the surgical tool 405 relative to the imaged vertebral body of interest can be established through a calibration procedure. This procedure only needs to be performed once, provided the position of the cameras and projector are not altered in the system fixture.

Figure 28B:
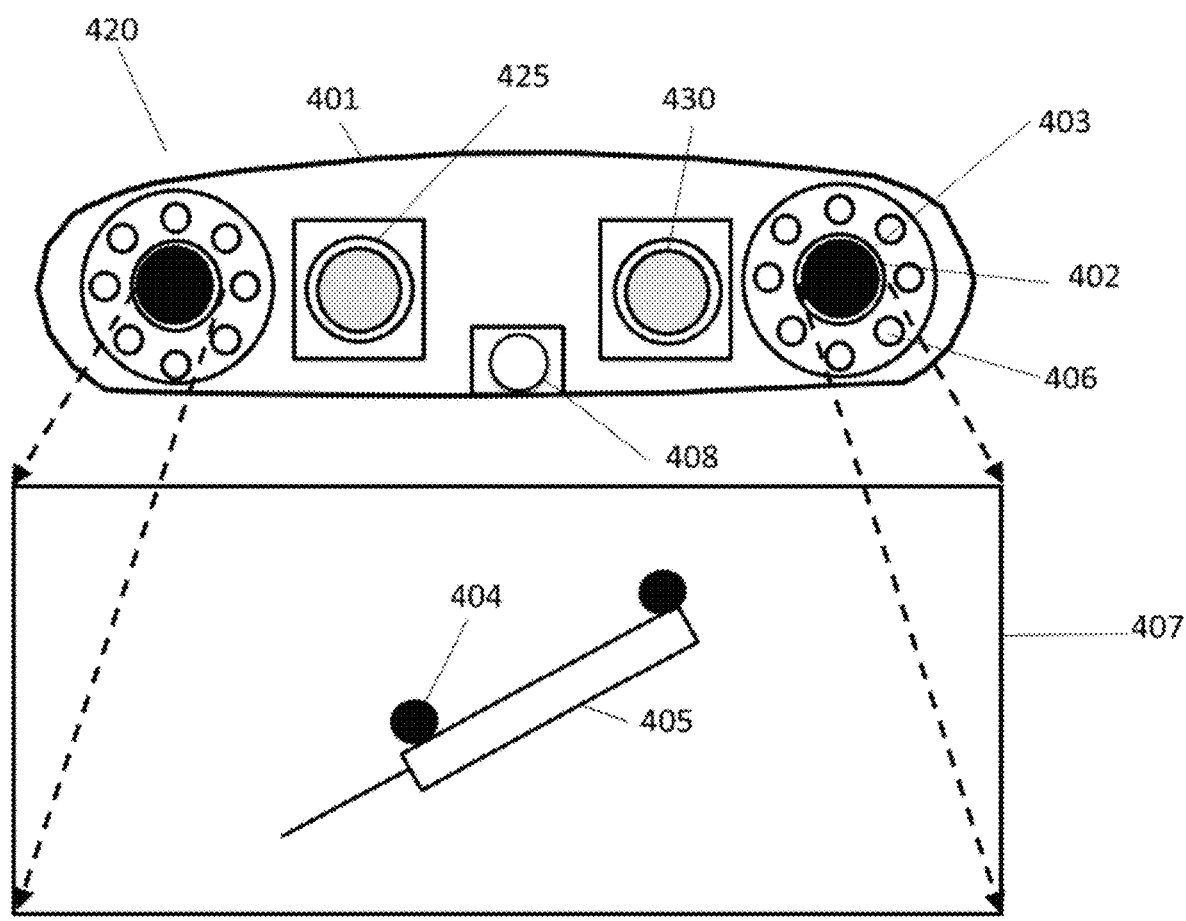
FIG. 28(b) is an illustration of an example system for surface topology detection and tool tracking using four cameras, where two of the cameras are used for surface topology imaging, and another two cameras are used for tool tracking. The cameras and projectors are rigidly attached to a frame so that a fixed spatial relationship exists between the components.

In the above example, an integrated, interframe system is described in which cameras 402 are employed for the dual role of detecting topology surface signals from the topology projector system 373 and detecting positioning signals from fiducial markers residing on the tool. In another embodiment, a second set of cameras may be provided, such that a dedicated set of cameras are provided for each imaging modality. This example implementation relaxes the optical system requirements and may be useful in enabling the use of dedicated cameras for each imaging modality that are suited to the needs of each modality, and also may provide a system with a faster response rate by avoiding the need to serially operate the cameras. Such embodiment is shown schematically in FIG. 28(b). System 420 is similar to that of the system 400, with the addition of two cameras 429. As before, cameras 402 detect fiducial markers 404 adhered to tool 405, where the fiducial markers 404 are illuminated by source 406. To acquire surface topology information, projector 408 is used to illuminate the target. The backscattered radiation from the projector is then detected by cameras 425. Optical filters 430, placed in front of cameras 425, are selected that has a passband in the range of wavelengths from projector 408, but that does not overlap significantly with the passband of filters 403.

Similarly, in some embodiments, cameras 402, 425, and projector 408 may be configured such that their respective focal regions (corresponding to their respective depths of focus) overlap at or near the region of interest, as described above with regard to FIG. 28(b). As described above, the field of view of illumination sources 406 should also overlap this region of interest, in order to provide suitable and sufficient illumination of fiducial markers 404.

In system 400 and 421, the cameras and projection systems are housed in a rigid frame 401, therefore a fixed relationship exists between each of the components. Similarly, a fixed relationship exists between the coordinate system used by the surface topology imaging system and the coordinate system of the tool tracking system. This relationship exists in the form of a calibration bringing one of the two coordinate systems into the other.

In one embodiment, the calibration between the surface topology imaging device and the position measurement device can be determined by imaging a set of targets visible by both devices, for example, reflective IR spherical markers. Using the acquired surfaces from the surface topology imaging datasets and the centroid positions of spheres from the position measurement device, a set of common points and/or features can be extracted. In the case of position measurement device, the centroid of each sphere is directly available. In the case of the surface topology imaging device, the center of each sphere can be extracted using the method disclosed below using back projection of surface normals. A transform between the two datasets can then be calculated using a registration routine such as a landmark transformation which calculates the best fit mapping of one point set onto the other, in a least squares sense. A minimum of three data points in each point set are required.

Figure 30:
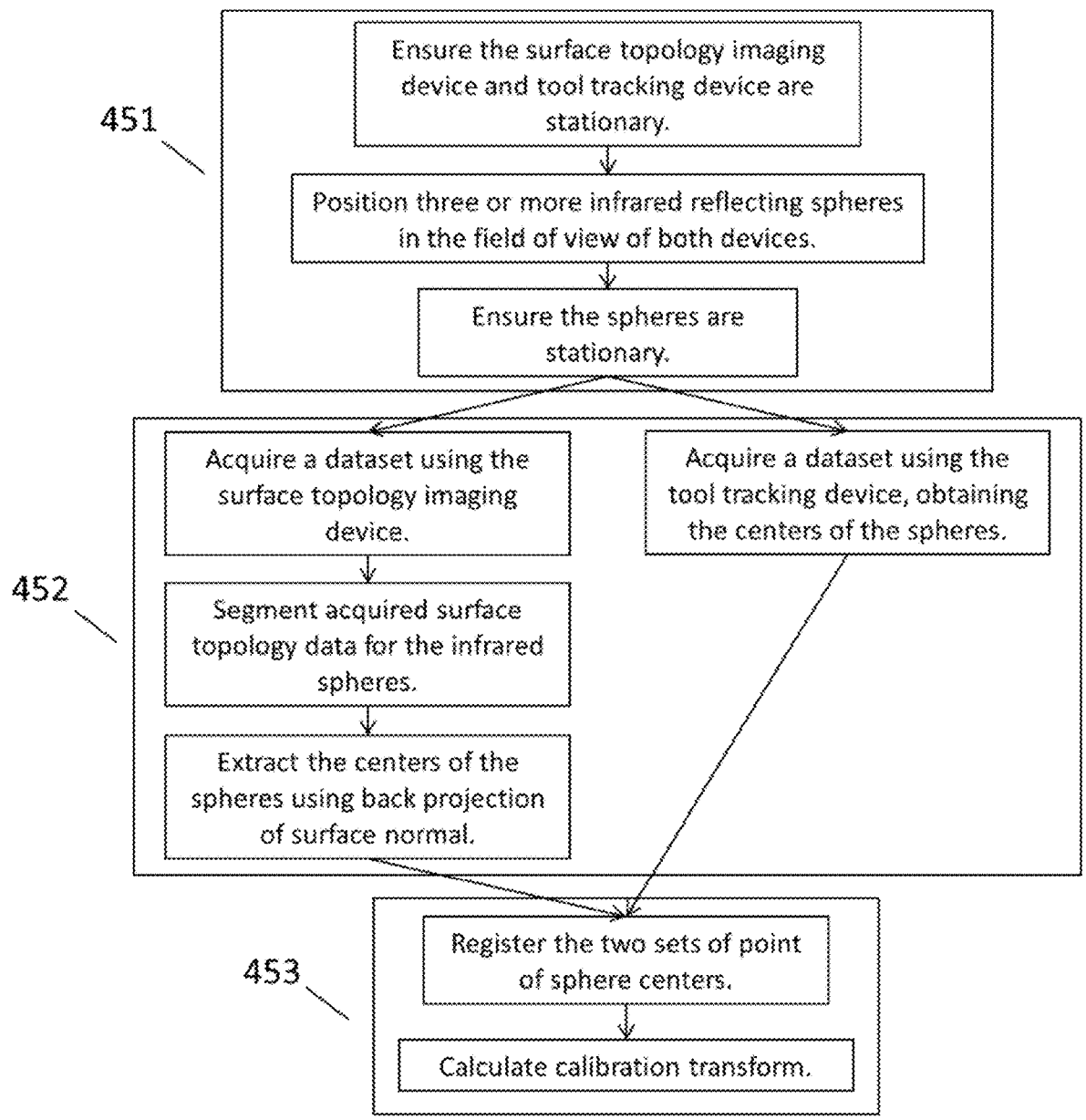
FIG. 30 is a flow chart illustrating an example method of performing a calibration to relate the coordinate system of the surface topology imaging system and the tool tracking system.

FIG. 30 is a flowchart illustrating an example method of performing the calibration with IR balls. The first steps 451 consist of positioning the topology imaging device, tool tracking device, and the IR spheres such that they are stationary relative to each other. The second steps 452 involve obtaining the centers of the IR spheres from the two systems. For the segmentation step, this can be done manually. The third steps 453 performs a registration on the two point sets to calculate the calibration transform that brings one of the two coordinate systems into the other.

Surface Identification and Tool Tracking

In another example embodiment, tool tracking may be directly integrated with the topology projector system such that the position and orientation of a tool is detected using the same topological imaging modality that is employed to optically interrogate the surface of interest. For example, surface identification may be employed to track the location and orientation (e.g. the pitch) of a surgical tool. Accordingly, the ability to provide surgical guidance feedback for orthopaedic structures as described previously can be enhanced with topological-based guidance feedback relating to the surgical tool in 3D space, for example, by depicting where the surgical tool is and where it is planned to be with respect to the 7 degrees of freedom (x, y, z, roll, yaw, pitch, time) and may additionally be used for the placement of surgical tools or other items of interest.

Figure 17:
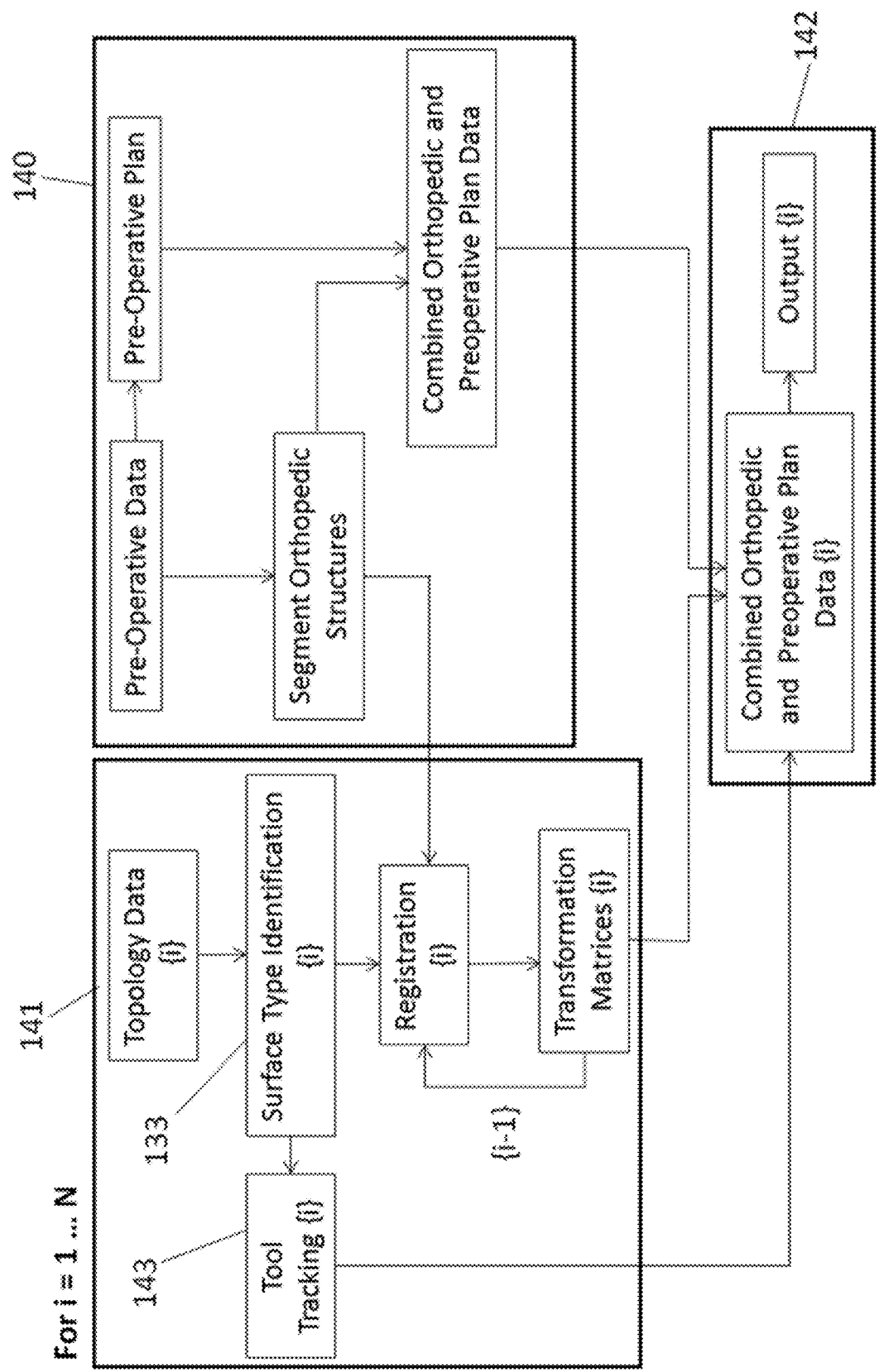
FIG. 17 is a flow diagram of an example implementation of a method of intraoperative surgical guidance feedback including surface identification and tool tracking.

Referring to FIG. 17, an example embodiment of surgical guidance with surface identification 133 and tool tracking 143 is illustrated. Block 140, 141, and 142 are otherwise similar to Block 130, 131, and 132 of FIG. 16. This embodiment is further illustrated in the example below, with reference to FIGS. 30 to 32.

Figures 31A, 31B:
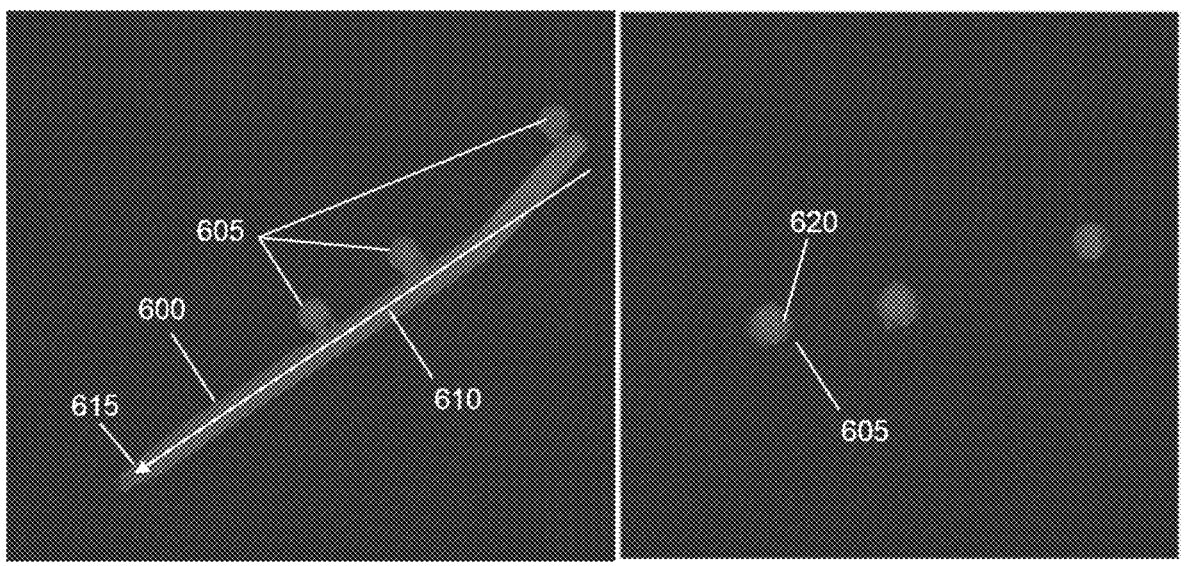
FIGS. 31(a) and 31(b) show (a) a full surface model of the tool to be tracked with center line and tip specified, and (b) marker balls from tool segmented and centers calculated/specified.

In the present non-limiting example, the tracking of a surgical tool is illustrated using surface identification via a structured light system. FIG. 31(a) shows an image of a tool 600 to be tracked. In a first step, fiducial markers are attached or adhered to the tool. The fiducial markers are passive, surface identification based, markers that are selected to be identifiable by the structured light system at multiple positions and orientations. Accordingly, in one example, the markers may be spherical balls 605, which present a common surface profile independent of orientation.

In one example implementation, the balls may have a diameter of 0.5-1 cm. Smaller ball diameters may also be employed using a camera of sufficient resolution and an appropriate fringe projection. Increasing the resolution of the system generally requires more computation power to process the data. It is to be understood that alternative non-spherical surface profile markers may alternatively be employed, such as planar polygon shapes (for example, triangles and squares), where the corners of the polygon can be used to determine the center of the shape.

In general, any landmark on a tool can be specified as a fiducial marker, provided that a suitable surface can be identified over a wide range of positions and angular orientations. Also, these landmarks should be sufficiently spaced spread out across the tool of interest to increase the tracking accuracy. In practice, these landmarks should not be positioned so that they can be blocked from the field of view when the tool is held. As will be shown below, a sphere is an effective marker since the center of a sphere can be easily extracted even if it is partially blocked.

The marker balls may be attached or adhered to the tool at three or more locations to support 3D position and orientation sensing. In one example, the marker balls may be screwed onto the tool at 3 locations. Other techniques of attaching the balls include snap-on methods or permanent attachment via adhesives, depending on the required use of the tool.

After having attached the markers to the tool, a 3D surface model of the tool is obtained. An orientation axis 610 and tip position 615 of the tool is then determined and recorded. The 3D model can be imported from computer aided design (CAD) drawings, in which case the tool's tip, orientation axis, and the position of the marker balls can be specified. Alternatively, for a tool without a CAD drawing, the tool can be profiled with the structured light scanner to obtain its 3D geometry. From the acquired point cloud, the tool tip and orientation axis can be extracted. The center of the marker balls can then be estimated mathematically based on the shape of the marker balls or specified manually.

For simple cylindrically symmetric shapes (e.g. a cylinder), the orientation axis and tip position may be calculated automatically based on the dimensions of the tool, using either the CAD drawings or from the point cloud acquired from a structured light scanner. In another example method, the orientation axis and tip may be defined manually via CAD drawings.

In the case where the tool does not have a tip or is not cylindrically symmetric, different measures can be used to specify the position and orientation of the tool. For example, in the case of an ultrasound transducer which is being tracked, the center of the transducer can be specified and an orientation axis can be defined by first defining a plane tangential to the transducer face. Then a normal to this plane, which passes through the center of the transducer, can be used to specify an orientation axis. For surgical navigation, the orientation axis is generally centerline of the tool, as it generally aligns with the axis of an interventional device to be inserted, such as a screw.

The orientation axis 610 and tip position 615 can be stored as 3D vector and a point relative to the coordinate system of the CAD drawing or point cloud. This can be saved into a calibration file that can be loaded into the navigation system. Multiple calibration files may be generated and loaded such that multiple tools can be tracked individually or at the same time during navigation.

The center of the marker balls to be tracked is then determined and recorded in a relative coordinate system. These centers are denoted in the present example by {P1, P2, P3}, and the center of one of the balls is shown in FIG. 31(b) at 620. This specifies a unique geometry that will be isolated and tracked intraoperatively, as shown below. These three points uniquely determine the orientation and location of the full tool in 3D space and hence the orientation axis and tip position.

Figures 32A, 32B:
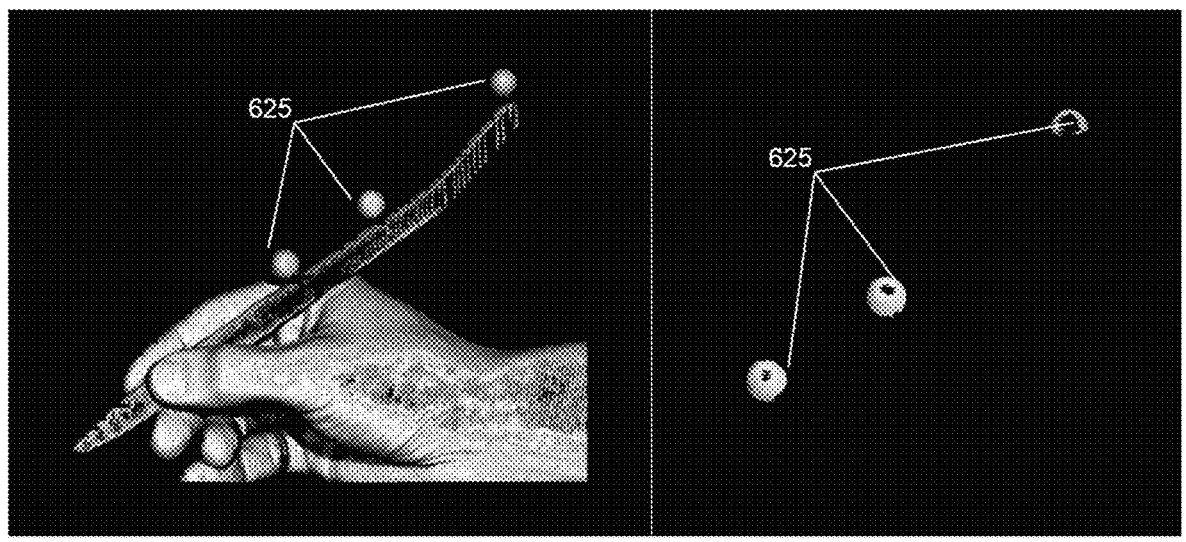
FIGS. 32(a) and 32(b) show (a) a surface topology scan acquired during a procedure, and (b) the automatic segmentation of marker balls based on color.

The topology of the tool is then intraoperative scanned using the structured light projection system. In order to detect the position and orientation of the tool, three marker balls should be partially visible in the scan. FIG. 32(a) illustrates an acquired surface topology scan of the tool and the three marker balls. As can be seen, the full tool does not need to be in the field of view and there can be additional surfaces in the field, such as the surgeon's hands. If, during tracking, shadowing occurs such that two or less balls are detected, the tracking is stopped. Such an event can be limited through the positioning of multiple cameras such that the markers are consistently in the field of view. Alternatively, there can be more than 3 markers on the surgical instruments, to increase the probability of any 3 markers being visible at any given time.

After obtaining the topological surface scan, the surfaces of the balls are identified. In one example, the surfaces are identified using spectral filtering to isolate the ball surfaces from the remainder of the image. This may be performed by acquiring a full color (white light) surface profile of the tool using a standard projector and a colour camera. By using ratios of the R, G and B channels, the marker balls surfaces 625 can be identified as seen in FIG. 32(b). In the present example, ball surfaces were identified by G/R and G/B values greater than 1.1 and less than 255. No filters were used in this implementation and all points outside of this range were removed. In an alternative embodiment, band-pass filters could be used to accomplish similar results.

Figure 33A:
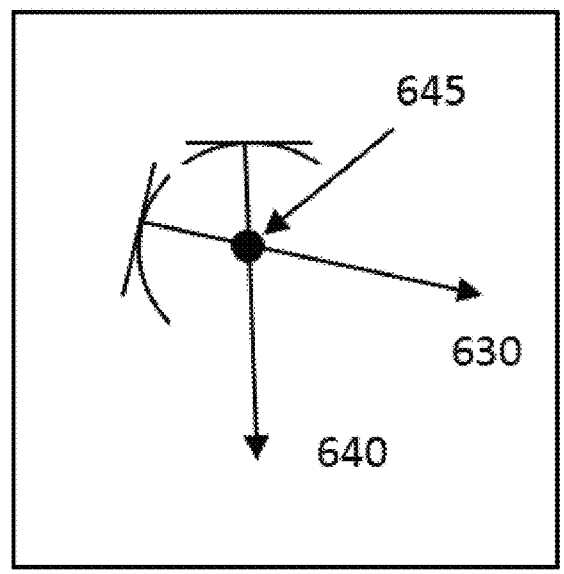
FIGS. 33(a) and 33(b) provide (a) an illustration of the geometrical relationships employed to determine the center of a detected ball, and (b) a plot that demonstrates the decrease in the standard deviation of the determined marker position with the number of surface normals employed in the calculation.
Figure 33B:
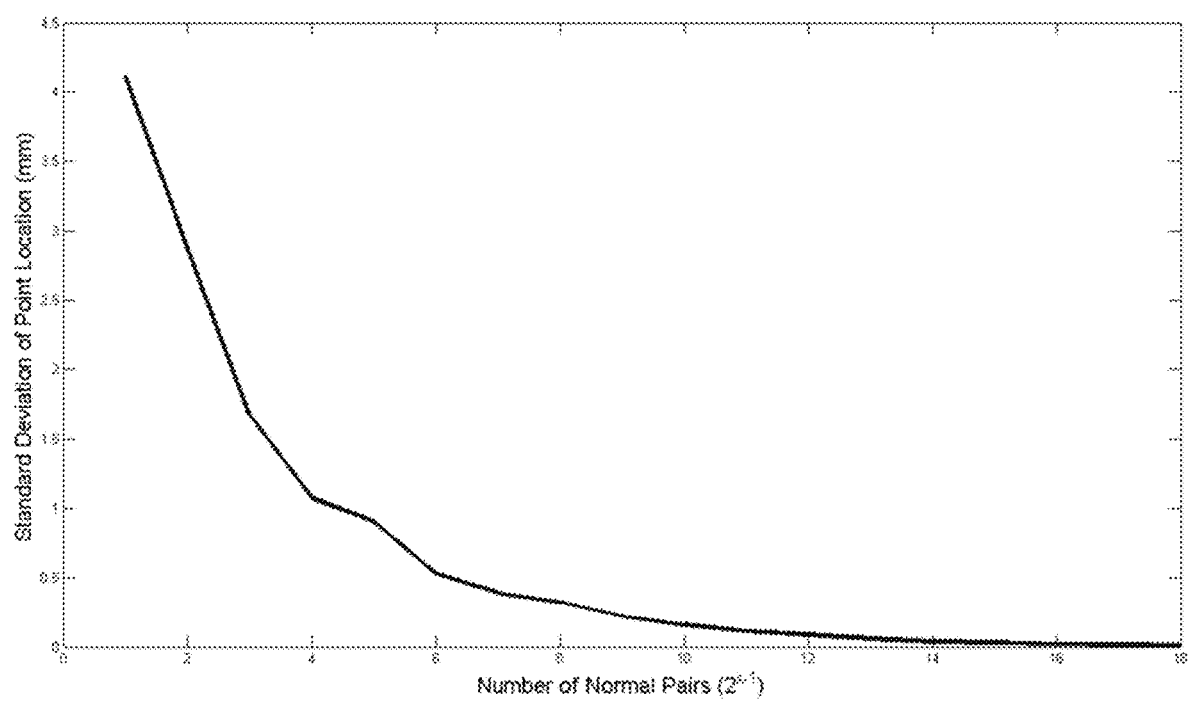

Having identified the ball surfaces, the ball center locations {Q1, Q2, Q3} are then determined. This can be accomplished by back projection of surface normals and determining the closest point of approach for each pair of normals. The mean of all closest points of approach for each marker ball is the approximated center. This method is illustrated in FIG. 33(a), where normals 630 and 640 are employed to determine center location 645 of a ball. In principle, only two normals are needed to specify an approximate center of the marker ball. However, FIG. 33(b) demonstrates how the standard deviation of the point location decreases as the number of normal pairs used increases. A smaller standard deviation results in a smaller variability in locating the center of the marker ball.

Figure 34:
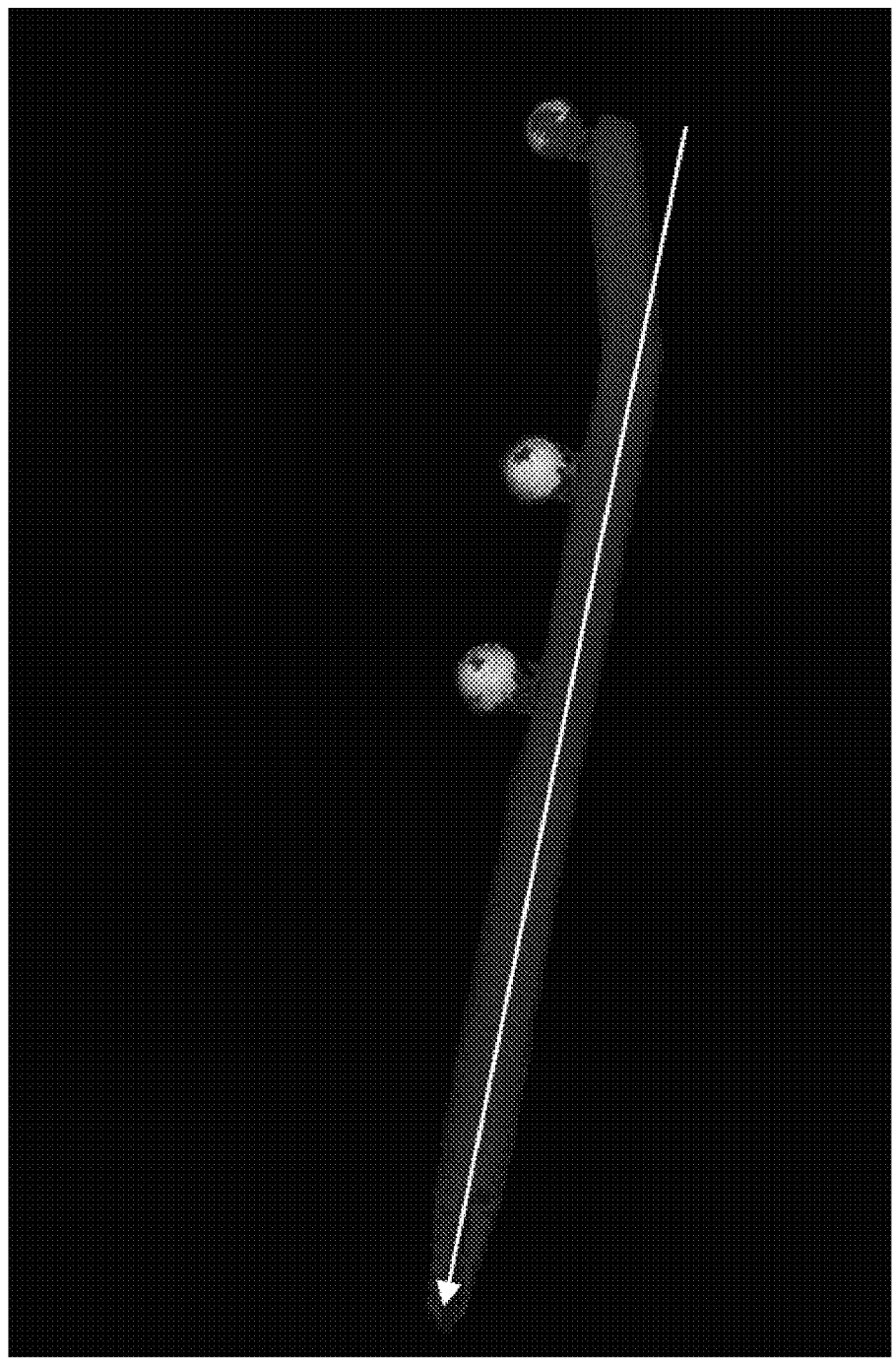
FIG. 34 shows the redisplay of the full tool with centerline and tip specified after performing landmark registration.

Finally, landmark registration of the ordered sets {P1,P2, P3} to {Q1,Q2,Q3} may be performed to obtain a transform M that maps the full tool to the partial surface scan of tool. Methods for landmark registration of ordered sets are known to those skilled in the art, for example, as described in Berthold K. P. Horn (1987), "Closed-form solution of absolute orientation using unit quaternions". Having determined the transform M, the full tool model is then transformed to the current tool position. As shown in FIG. 34, the full tool may be subsequently shown in display, including known 3D surface based on initial measurement, and the system can track the spatial position and orientation of surgical tool using surface-based registration. The resulting tracked tool may be displayed with co-registered 3D pre-operative image data and/or a surgical plan, as described in the preceding examples.

The present spectral identification method may be extended to enable the simultaneous tracking of multiple tools, provided that the balls on each different tool have different colors. This can be achieved by selecting materials that can be identified throughout the any suitable portion of the electromagnetic spectrum, such as UV, visible, IR, etc. Preferably, ball marker colors are selected that would not typically be found in the surgical field of view.

The preceding description has been made with respect to the provision of guidance feedback to surgeons, however, it is recognized that such guidance feedback can also be provided to, and utilized by, other persons or systems, such as autonomous or semi-autonomous surgical robotic systems for the automated guidance of such surgical robotic systems. Furthermore, although many of the preceding examples include the co-registration of a surgical plan, it is to be understood that embodiments may be practiced without the incorporation of a surgical plan.

Furthermore, while the preceding disclosure has been provided in the context of surgical navigation, it is to be understood that the scope of the embodiments provided herein not intended to be limited to surgical practice. Examples of implementation embodiments as described above are provided for illustration purposes rather than to limit the scope of possible embodiments. Accordingly, systems and methods disclosed herein may be adapted to a wide variety of uses and applications in which it is useful or desirable to employ the registration of surface image data to three-dimensional volume image data.

For example, the embodiments provided herein may be useful in fields such as test and measurement, manufacturing, non-destructive testing, geo-prospecting, training, education, mixed reality applications and the video game industry. In a manufacturing example, made products could be dimensionally compared and quantified to their original computer aided design (CAD) to verify a proper design and manufacturing processes via the system described herein. An additional manufacturing application includes use in an assembly line, where components are added to a base structure. Topology imaging of the base structure can be used to identify its position and orientation. Similarly, the robotic arm's position and orientation can be tracked. Using the present method, this would allow precise placement of components onto the base structure via the robotic arm. Another application is the identification of inefficient machining tools in a computer numerical control (CNC) system. The individual machine bits of a CNC machine are routinely changed when they become dull or broken. The system described herein could create 3D profiles of all the machine bits, prior to or during system use, for comparison with pre-loaded ideal bit profiles. The system could then register the 3D bit profiles, to the pre-loaded model to identify bits that have become dull, have been installed improperly or have broken in an effort to reduce machining errors. The methods disclosed can also be used to identify or sort through items in an assembly line, where the topology of the item under inspection can be compared to a known model of the item.

An additional example includes the use of the system described herein to track multiple targets using surface type identification to merge virtual models of human actors, animals, vehicles, etc. for the video game or computer generated imagery industry. The present embodiments can also be of use in mixed reality applications for surgical training. For example, the position and orientation of a patient phantom can be determined using its 3D topology. Through augmented reality using head mounted displays, or other forms of displays, that are tracked in space, different clinical scenarios can be overlaid onto the patient phantom. Physical tools held by the trainee would be tracked relative to the patient phantom, to allow interventions to be performed virtually. In certain scenarios of the above examples, portability of the system may be necessary for field use. Simultaneous real-time triangulation-based tool tracking and topology imaging (system 400) may be advantageous. Such portability may be suitable to be fitted onto a mobile robot, to perform object identification to navigate a terrain, and perform object manipulation through a tracked robotic arm.

Although some of the drawings illustrate a number of operations in a particular order, operations which are not order-dependent can be reordered and other operations can be combined or broken out. While some reordering or other groupings are specifically mentioned, others will be apparent to those of ordinary skill in the art and so do not present an exhaustive list of alternatives. Moreover, it should be recognized that the stages could be implemented in hardware, firmware, software or any combination thereof.

In various embodiments, hardwired circuitry can be used in combination with software instructions to implement the embodiments. Thus, the techniques are neither limited to any specific combination of hardware circuitry and software nor to any particular source for the instructions executed by the data processing system. In this description, various functions and operations are described as being performed by or caused by software code to simplify description. However, those skilled in the art will recognize what is meant by such expressions is that the functions result from execution of the code by a processor, such as a microprocessor.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of determining a calibration transform between a first frame of reference associated with a surface topology imaging device and a second frame of reference associated with an optical tracking system, the method comprising the steps of:
   positioning three or more fiducial markers such that they reside within respective fields of view of both the surface topology imaging device and the optical tracking system, and such that the fiducial markers are stationary with respect to one another;
   employing the surface topology imaging device to scan the fiducial markers and acquire surface data;
   processing the surface data to locate each fiducial marker in the first frame of reference;
   employing the optical tracking system to track the fiducial markers and locate each fiducial marker in the second frame of reference; and
   registering the locations of the fiducial markers in the first frame of reference with the locations of the fiducial markers in the second frame of reference, thereby obtaining the calibration transform between the first frame of reference and the second frame of reference.

2. The method according to claim 1 wherein the step of processing the surface data to locate a given optical tracking fiducial marker in the first frame of reference comprises:
   segmenting the surface data to obtain segmented surface data associated with the given optical tracking fiducial marker; and
   processing the segmented surface data to locate the given optical tracking fiducial marker in the first frame of reference.

3. The method according to claim 2 wherein the segmented surface data associated with the given optical tracking fiducial marker is processed to determine a center location of the given optical tracking fiducial marker in the first frame of reference.

4. The method according to claim 3 wherein the given optical tracking fiducial marker is spherical in shape, and wherein the center location of the given optical tracking fiducial marker is determined by:
   processing the segmented surface data to identify a plurality of surface normals associated with a surface of the given optical tracking fiducial marker;
   backprojecting the surface normals beneath the surface of the given optical tracking fiducial marker; and
   processing the backprojected surface normals to identify the center location.

5. The method according to claim 4 wherein processing the backprojected surface normals comprises identifying the center location based on average point of closest approach between the backprojected surface normals.

6. The method according to claim 2 wherein spectral filtering is employed to segment the surface data.

7. The method according to claim 2 wherein the surface data is manually segmented.

8. The method according to claim 1 wherein the calibration transform is generated by computing a landmark transformation.

9. The method according to claim 1 wherein the surface topology imaging device is movable relative to the optical tracking system.

10. The method according to claim 1 wherein the surface topology imaging device is rigidly fixed relative to the optical tracking system.

11. The method according to claim 1 wherein the fiducial markers reside on a surgical tool.

12. The method according to claim 1 wherein the fiducial markers are passive.

13. A surgical guidance system comprising:
an optical tracking system;
a surface topology imaging device; and
a surgical guidance controller operatively connected to the surface topology imaging device and the optical tracking system, wherein the surgical guidance controller includes a processor configured to generate a calibration transform between a first frame of reference associated with the surface topology imaging device and a second frame of reference associated with the optical tracking system by:
controlling the surface topology imaging device to scan fiducial markers residing within respective fields of view of both the surface topology imaging device and the optical tracking system, thereby obtaining surface data;
processing the surface data to locate each fiducial marker in the first frame of reference;
employing the optical tracking system to track the fiducial markers and locate each fiducial marker in the second frame of reference; and
registering the locations of the fiducial markers in the first frame of reference with the locations of the fiducial markers in the second frame of reference, thereby obtaining the calibration transform between the first frame of reference and the second frame of reference.

14. The surgical guidance system according to claim 13 wherein surgical guidance controller is configured such that processing the surface data to locate a given optical tracking fiducial marker in the first frame of reference comprises:
segmenting the surface data to obtain segmented surface data associated with the given optical tracking fiducial marker; and
processing the segmented surface data to locate the given optical tracking fiducial marker in the first frame of reference.

15. The surgical guidance system according to claim 14 wherein the surgical guidance controller is configured such that the segmented surface data associated with the given optical tracking fiducial marker is processed to determine a center location of the given optical tracking fiducial marker in the first frame of reference.

16. The surgical guidance system according to claim 15 wherein the surgical guidance controller is configured such that the center location of the given optical tracking fiducial marker is determined by:
processing the segmented surface data to identify a plurality of surface normals associated with a surface of the given optical tracking fiducial marker, modelling the given optical tracking fiducial marker as being spherical in shape;
backprojecting the surface normals beneath the surface of the given optical tracking fiducial marker; and
processing the backprojected surface normals to identify the center location.

17. The surgical guidance system according to claim 16 wherein the surgical guidance controller is configured such that processing the backprojected surface normals comprises identifying the center location based on average point of closest approach between the backprojected surface normals.

18. The surgical guidance system according to claim 14 wherein the surface topology imaging device and the surgical guidance controller are configured such that spectral filtering is employed to segment the surface data.

19. The surgical guidance system according to claim 13 wherein the surgical guidance controller is configured such that the calibration transform is generated by computing a landmark transformation.

20. The surgical guidance system according to claim 13 wherein the surface topology imaging device is movable relative to the optical tracking system.

21. The surgical guidance system according to claim 13 wherein the surface topology imaging device is rigidly fixed relative to the optical tracking system.

* * * * *